United States Patent [19]
Imakawa

[11] Patent Number: 5,738,845
[45] Date of Patent: Apr. 14, 1998

[54] HUMAN INTERFERON τ PROTEINS AND METHODS OF USE

[75] Inventor: Kazuhiko Imakawa, Derby, Kans.

[73] Assignee: The Women's Research Institute, Wichita, Kans.

[21] Appl. No.: 443,883

[22] Filed: May 31, 1995

Related U.S. Application Data

[63] Continuation of Ser. No. 438,753, May 10, 1995, which is a continuation-in-part of Ser. No. 139,891, Oct. 19, 1993, abandoned, which is a continuation-in-part of Ser. No. 847,741, Mar. 9, 1992, abandoned, which is a continuation-in-part of Ser. No. 318,050, Mar. 2, 1989, abandoned, said Ser. No. 139,891, Oct. 19, 1993, is a continuation-in-part of Ser. No. 969,890, Oct. 30, 1992, abandoned.

[51] Int. Cl.$^6$ .................. C07K 14/555; A61K 38/21; C12N 15/20
[52] U.S. Cl. .................. 424/85.4; 530/351; 435/69.52
[58] Field of Search .................. 530/351; 435/69.52; 424/85.4

[56] References Cited

U.S. PATENT DOCUMENTS

| | | |
|---|---|---|
| 4,997,646 | 3/1991 | Hansen et al. . |
| 5,540,923 | 7/1996 | Ebbesen et al. ............ 424/85.5 |

FOREIGN PATENT DOCUMENTS

| | | |
|---|---|---|
| 0 367 063 | 5/1990 | European Pat. Off. . |
| WO 90/09806 | 9/1990 | WIPO . |
| WO 93/12146 | 12/1992 | WIPO . |
| WO 94/10113 | 5/1994 | WIPO . |

OTHER PUBLICATIONS

Bazer, F.W., and Johnson, H.M., "Type I Conceptus Interferons: Maternal Recognition of Pregnancy Signal and Potential Therapeutic Agents", *American J. of Reproductive Immun.* 26:19–22 (1991).

Brazer, F.W., et al., "Roles of Ovine Trophoblast Protein–1 and Oestradiol/Prolactin in the Establishment of Pregnancy in Sheep and Pigs", *Reprod. Fertil. Dev.* 4:335–340 (1992).

Farin, C.E., et al., "Expression of Trophoblastic Interferon Genes in Sheep and Cattle", *Biol. of Reprod.* 43:210–218 (1990).

Hansen, T.R., et al., "Complex Binding of the Embryonic Interferon, Ovine Trophoblast Protein–1, to Endometrial Receptors", *J. Interferon Res.* 9:215–225 (1989).

Hansen, T.R., et al., "The Genes for the Trophoblast Interferons and the Related Interferon–$\alpha_{II}$ Possess Distinct 5'–Promoter and 3'–Flanking Sequence", *J. Biol. Chem.* 266(5):3060–3067 (1991).

Imakawa, K., et al., "Interferon–like sequence of ovine trophoblast protein secreted by embryonic trophectoderm", *Nature* 330:377–379 (1987).

Imakawa, K., et al., "Molecular Cloning and Characterization of Complementary Deoxyribonucleic Acids Corresponding to Bovine Trophoblast Protein 1: A Comparison with Ovine Trophoblast Protein–1 and Bovine Interferon–$\alpha_{II}$", *Mol. Endocrin.* 3(1):127–139 (1989).

Leaman, D.W., et al., "Genes for the Trophoblast Interferons and their Distribution among Mammals", *Reprod. Fertil. Dev.* 4:349–353 (1992).

Leaman, D.W., and Roberts, R.M., "Genes for the Trophoblast Interferons in Sheep, Goat, and Musk Ox and Distribution of Related Genes Among Mammals", *J. Interferon Res.* 12:1–11 (1992).

Newton, G.R., et al., "Inhibition of Lymphocyte Proliferation by Ovine Trophoblast Protein–1 and a High Molecular Weight glycoprotein Produced by the Peri–Implantation Sheep Conceptus", *Am. J. Reprod. Immunol.* 19:99–107 (1989).

Ott, T.L., et al., "Cloning and Expression in *Saccharomyces cerevisiae* of a Synthetic Gene for the Type–I Trophoblast Interferon Ovine Trophoblast Protein–1: Purification and Antiviral Activity", *J. Interferon Res.* 11:357–364 (1991).

Pontzer, C.H., et al., "Antiviral Activity of the Pregnancy Recognition Hormone Ovine Trophoblast Protein–1", *Biochem. and Biophys. Res. Commun.* 152(2):801–807 (1988).

Pontzer, C.H., et al., "Localization of an antiviral site on the pregnancy recognition hormone, ovine trophoblast protein–1", *Proc. Natl. Acad. Sci. USA* 87:5945–5949 (1990).

Pontzer, C.H., et al., "Antiproliferative Activity of a Pregnancy Recognition Hormone, Ovine Trophoblast Protein–1", *Cancer Res.* 51:5304–5307 (1991).

Roberts, R.M., et al., "Interferons at the placenta interface", *J. Reprod. Fert., Suppl.* 41:63–74 (1990).

Roberts, R.M., et al., "Unique Features of the Trophoblast Interferons", *Pharmac. Ther.* 51:329–345 (1991a).

Roberts, R.M., et al., "The polypeptides and genes for ovine and bovine trophoblast protein–1", *J. Reprod. Fert., Suppl.* 43:–3–12 (1991b).

Roberts, R.M., et al., "Interferons as Hormones of Pregnancy", *Endocrine Rev.* 13(3):432–452 (1992).

(List continued on next page.)

*Primary Examiner*—David L. Fitzgerald
*Attorney, Agent, or Firm*—Charles K. Sholtz; Gary R. Fabian; Peter J. Dehlinger

[57] ABSTRACT

The present invention describes the production of interferon-τ proteins and polypeptides derived therefrom. The antiviral and anticellular proliferation properties of these proteins and polypeptides are disclosed. One advantage of the proteins of the present invention is that they do not have cytotoxic side-effects when used to treat cells. Structure/function relationships for the interferon-τ protein are also described. In one aspect, the invention includes ovine interferon-τ. In another aspect the invention includes multiple forms of human interferon-τ.

18 Claims, 21 Drawing Sheets

OTHER PUBLICATIONS

Tuo, W., et al., "Natural Killer Cell Activity of Lymphocytes Exposed to Ovine, Type I, Trophoblast Interferon", *AJRI* 29:26–34 (1993).

Vallet, J.L., et al., "The Effect of Ovine Trophoblast Protein–One on Endometrial Protein Secretion and Cyclic Nucleotides", *Biol. Reprod.* 37:1307–1316 (1987).

Vallet, J.L., et al., "Effect of ovine conceptus secretory proteins and purified ovine trophoblast protein–1 on interoestrous interval and plasma concentrations of prostaglandins F–2α and E and 13,14–dihydro–15–keto–prostaglandin F–2α in cyclic ewes", *J. Reprod. Fert.* 84:493–504 (1988).

Whaley, A.E., et al., "Molecular Cloning of Unique Interferons from Human Placenta," in *Society of Reproduction, 24th Annual Meeting*, pp. 186 (1991).

Yong, K., et al., "Insulin–Like Growth Factors in Sheep Uterine Fluids: Concentrations and Relationship to Ovine Trophoblast Protein–1 Production during Early Pregnancy", *Biol. Reprod.* 45:135–142 (1991).

Fig. 1A

METOTP-1.SEQ4 -> Restriction Map

DNA sequence    540 b.p.    ATGTGGTACCAG ... CCGTAAGGTACC    linear

```
                                                                                                     Sau96 I    Cla I
                                                          Taq I                                      Ava II     Hinf I
                                                          Xho I                            Mse I
       Stu I                         BstU I      Hga I    Pae37 I                           Dra I
       Hae I                         Nru I       SfaN I   Ava I
       ScrF I
       EcoR II
       BstN I
  Rsa I
  Nla IV
  Kpn I
  Ban I Hae III
  Asp718
  || |·||                            ||          ||       ||                                ||       |·|        ||
  5                                  25          36       47                                57       69         78
  5    12                            26                   43 47                             58       69         80
  5                                                          48                                                 80
  5
  6
ATGTGGTACCAGGCCTGCTACCTGCTGTCGGAGAAAACTGATGCTGCTCGAGAAAATTTAAAACTGCTGGACCGTATGAA  80
TACACCATGGTCCGGACGATGGACGAGCAGCGCTTTTGACTACGACGAGCTCTTTTAAATTTTGACGACCTGGCATAGTT
  9
  9
  9
  11
  11
```

Fig. 1B

```
                  Fnu4H I
                  Bbv I
                  Alu I                                                                      Mae III
         BsmA I   Pyu II          Xmn I                                                      Hph I
Taq I            NsoB II  Msp I                   Fnu4H I                                    BstE II
 |       |       |||      |       |                |                                         |||
TCGATTGTCTCCGCACAGCTGCCTGCAAGAGACTTCGGTCTGCCGGCAGGAAATGGTTGAAGGTGACCAACTGC 160
AGCTAACAGAGGCGTGTCGACGGACGTTCTCTGAAGCCAGACGGCGTCCTTTACCAACTTCCACTGGTTGACG
 |       |       |||      |       |                |                         |||
 81              96       111                      129                        148
                 96       111                                                 148
                 97                                                           149
                 98        114
                 98
                 Msp I
                 ScrF I                 Fnu4H I
                 Nci I                  Bbv I
                 Bcn I                  Pst I
         Alu I   Hpa II                 Fnu4H I                                 Fnu4H I
         HinD III        Rsa I          Bbv I                                   Hae III
                                                                                Gdi II
                                                                  Mbo II        Eag I
                                                                                Eae I
          |||    ||   |  |      |       |||                        |            ||||
AAAAAGACCAAGCTTCCCCGGTACTGTATGAAATGCTGCAGCAGTCTTTCAACCTGTTCTACACTGAACATTCTTCGGCC 240
TTTTTCTGGTTCGAAGGGCCATGACATACTTTACGACGTCGTCAGAAAGTTGGACAAGATGTGACTTGTAAGAAGCCGG
          |||    ||   |  |      |       |||                        |            ||||
          170    178     181             195                        232          236
          171    177                     195                                     236
                 177                     196                                     236
                 177                     198                                     237
                 178                     198                                     238
```

Fig. 1C

```
                                                                                    Scrf I
                                                                                    PflM I
                                                                                    EcoR II
                                                                                    BstN I
                                                                                   Hae III
                                                                                    Hae I
                                                                                    Eae I
                                                               Bsr I      Sau96 I   Bal I
         Mae I                                                            Sec I
         Xba I     HgiA I                                                 Dsa I
         Mbo II    Bspl1286 I                  AlwN I  Ava II             ——
Bar I    ——        ApaL I                      ——      ——        ——   ——       320
——       ——        ——            270           286     291  294  312    315 316 318
GCTTGGGACACTACTCTTCTAGAACAACTGTGCACTGGTCTGCAACAGCAACTGGACCATCTGGACACTTGCCGTGCCA
CGAACCCTGTGATGAGAAGATCTTGTTGACACGTGACCAGACGTTGTCGTTGACCTGGTAGACCTGTGAACGGCACCGGT
——       ——        ——            ——            ——      ——   ——   ——     ——  ——  ——
254      258       270           274           286     291  294  312    315 316 318
255      259       270                                                  315     318
                   270                                                          318
```

```
              -23                                                                      -9
              met ala phe val leu ser leu leu met ala leu val leu val ser
oIFNt   cccc  ATG GCC TTC GTG CTC TCT CTA CTG ATG GCC CTG GTG CTG GTC AGC
huIFNt1 cccc  ATG GCC TTC GTG CTC TCT CTA CTC ATG GCC CTG GTG CTG GTC AGC -8                                      -1 +1                                          11
 tyr gly pro gly gly ser leu gly cys tyr leu ser arg lys leu met leu asp ala
 TAT GGC CCA GGA GGA TCT CTG GGT TGT TAC CTA TCT CGG AAA CTC ATG CTG GAT GCC
 TAC GGC CCA GGA GGA TCC CTG GGT TGT GAC CTG TCT CAG AAC CAC GTG CTG GTT GGC
                                     asp         gln asn his val     val gly 12                                                                                     30
 arg glu asn leu lys leu leu asp arg met asn arg leu ser pro his ser cys leu
 AGG GAG AAC CTC AAG CTC CTG GAC CGA ATG AAC AGA CTC TCC CCT CAT TCC TGT CTG
 AGG AAG AAC CTC AGG CTC CTG GAC GAA ATG AGG AGA CTC TCC CCT CGC TTT TGT CTG
     lys             arg             glu     arg                 arg phe 31                                                                                     49
 gln asp arg lys asp phe gly leu pro gln glu met val glu gly arg gln leu gln
 CAG GAC AGA AAA GAC TTT GGT CTT CCC CAG GAG ATG GTG GAG GGC GAC CAG CTC CAG
 CAG GAC AGA AAA GAC TTC GCT TTA CCC CAG GAA ATG GTG GAG GGC GGC CAG CTC CAG
                             ala                                 gly 50                                                                                     68
 lys asp gln ala phe pro val leu tyr glu met leu gln gln ser phe asn leu phe
 AAG GAC CAG GCC TTC CCT GTG CTC TAC GAG ATG CTC CAG CAG AGC TTC AAC CTC TTC
 GAG GCC CAG GCC ATC TCT GTG CTC CAT GAG ATG CTC CAG CAG AGC TTC AAC CTC TTC
 glu ala         ile ser         his 69                                                                                     87
 tyr thr glu his ser ser ala ala trp asp thr thr leu leu glu gln leu cys thr
 TAC ACA GAG CAC TCC TCT GCT GCC TGG GAC ACC ACC CTC CTG GAG CAG CTC TGC ACT
 CAC ACA GAG CAC TCC TCT GCT GCC TGG GAC ACC ACC CTC CTG GAG CAG CTC CGC ACT
 his                                                                         arg 88                                                                                    106
 gly leu gln gln gln leu asp his leu asp thr cys arg gly gln val met gly glu
 GGA CTC CAA CAG CAG CTG GAC CAC CTG GAC ACC TGC AGG GGT CAA GTG ATG GGA GAG
 GGA CTC CAT CAG CAG CTG GAC AAC CTG GAT GCC TGC CTG GGG CAG GTG ATG GGA GAG
         his                         asn         ala     leu 107                                                                                    125
 glu asp ser glu leu gly asn met asp pro ile val thr val lys lys tyr phe gln
 GAA GAC TCT GAA CTG GGT AAC ATG GAC CCC ATT GTG ACC GTG AAG AAG TAC TTC CAG
 GAA GAC TCT GCC CTG GGA AGG ACG GGC CCC ACC CTG GCT CTG AAG AGG TAC TTC CAG
             ala         arg thr gly     thr leu ala leu     arg 126                                                                                    144
 gly ile tyr asp tyr leu gln glu lys gly tyr ser asp cys ala trp glu ile val
 GGC ATC TAT GAC TAC CTG CAA GAG AAG GGA TAC AGC GAC TGC GCC TGG GAA ATC GTC
 GGC ATC CAT GTC TAC CTG AAA GAG AAG GGA TAC AGC GAC TGC GCC TGG GAA ACC GTC
         his val         lys                                         thr 145                                                                                    163
 arg val glu met met arg ala leu thr val ser thr thr leu gln lys arg leu thr
 AGA GTC GAG ATG ATG AGA GCC CTC ACT GTA TCA ACC ACC TTG CAA AAA AGG TTA ACA
 AGA CTG GAA ATC ATG AGA TCC TTC TCT TCA TTA ATC AGC TTG CAA GAA AGG TTA AGA
     leu     ile         ser phe ser ser leu ile ser     glu         arg 164                       172
 lys met gly gly asp leu asn ser pro end
 AAG ATG GGT GGA GAT CTG AAC TCA CCT TGA
 ATG ATG GAT GGA GAC CTG AGC TCA CCT TGA
 met     asp             ser
```

Fig. 3

| Peptides | MW | HI* | Sequence |
|---|---|---|---|
| IFNt(1-37) (SEQ ID NO:5) | 4465 | -0.78 | CYSLRKLMLDARENLKLLDRMNRLSPHSCLQDRKDFG |
| IFNt(34-64) (SEQ ID NO:6) | 3610 | -0.72 | KDFGLPQEMVEGDQLQKDQAFPVLYEMLQQS |
| IFNt(62-92) (SEQ ID NO:7) | 3586 | -0.53 | QQSFNLFYTEHSSAAWDTTLLEQLCTGLQQQ |
| IFNt(90-122) (SEQ ID NO:8) | 3712 | -0.86 | QQQLDHLDTCRGQVMGEEDSELGNMDPIVTVKK |
| IFNt(119-150) (SEQ ID NO:9) | 3948 | -0.56 | TVKKYFQGIYDYLQEKGYSDCAWEIVRVEMMR |
| IFNt(139-172) (SEQ ID NO:10) | 3818 | -0.11 | CAWEIVRVEMMRALTVSTTLQKRLTKMGGDLNSP |

*Hydropathic Index

Fig. 6

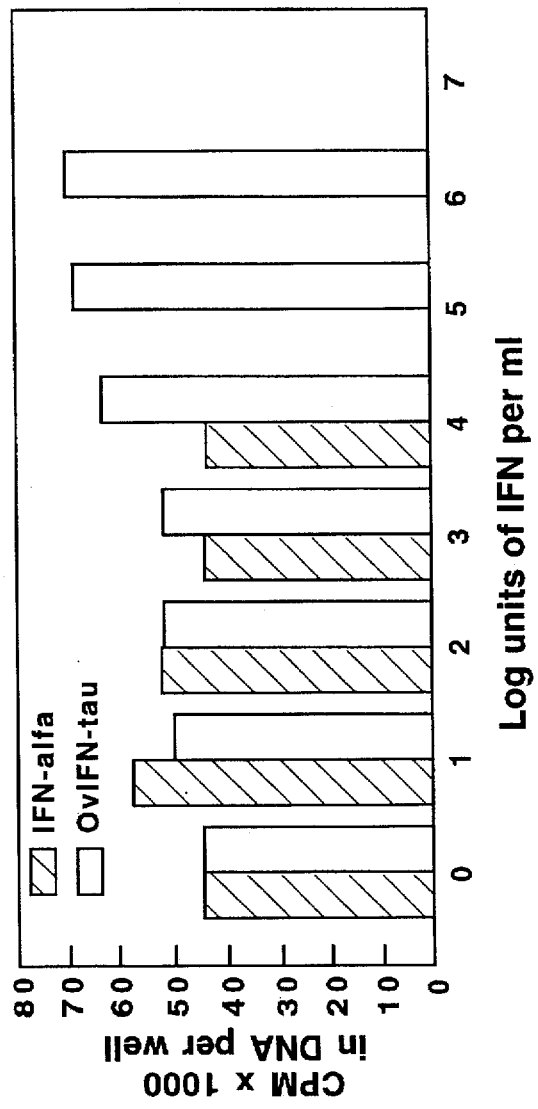

Fig. 8

```
  1                                                                            80
  CTGAGATGGGATCAGAGAACCTACCTGAAGGTTCCCCCTGACCCCATCTCAGCCAGCCCAGCAGCAGCCGCATCTTCCCC 81                                                                           140
  ATG GCC TTC GTG CTC TCT CTA CTG ATG GCC CTG GTG CTG GTC AGC TAT GGC CCA GGA GGA
  S1                                                                          S20
  Met Ala Phe Val Leu Ser Leu Leu Met Ala Leu Val Leu Val Ser Tyr Gly Pro Gly Gly
141                                                                           200
  TCT CTG GGT TGT TAC CTA TCT CGG AAA CTC ATG CTG GAT GCC AGG GAG AAC CTC AAG CTC
  S21  1                                                                       17
  Ser Leu Gly Cys Tyr Leu Ser Arg Lys Leu Met Leu Asp Ala Arg Glu Asn Leu Lys Leu
201                                                                           260
  CTG GAC CGA ATG AAC AGA CTC TCC CCT CAT TCC TGT CTG CAG GAC AGA AAA GAC TTT GGT
   18                                                                          37
  Leu Asp Arg Met Asn Arg Leu Ser Pro His Ser Cys Leu Gln Asp Arg Lys Asp Phe Gly
261                                                                           320
  CTT CCC CAG GAG ATG GTG GAG GGC GAC CAG CTC CAG AAG GAC CAG GCC TTC CCT GTG CTC
   38                                                                          57
  Leu Pro Gln Glu Met Val Glu Gly Asp Gln Leu Gln Lys Asp Gln Ala Phe Pro Val Leu
321                                                                           380
  TAC GAG ATG CTC CAG CAG AGC TTC AAC CTC TTC TAC ACA GAG CAC TCC TCT GCT GCC TGG
   58                                                                          77
  Tyr Glu Met Leu Gln Gln Ser Phe Asn Leu Phe Tyr Thr Glu His Ser Ser Ala Ala Trp
381                                                                           440
  GAC ACC ACC CTC CTG GAG CAG CTC TGC ACT GGA CTC CAA CAG CAG CTG GAC CAC CTG GAC
   78                                                                          97
  Asp Thr Thr Leu Leu Glu Gln Leu Cys Thr Gly Leu Gln Gln Gln Leu Asp His Leu Asp
441                                                                           500
  ACC TGC AGG GGT CAA GTG ATG GGA GAG GAA GAC TCT GAA CTG GGT AAC ATG GAC CCC ATT
   98                                                                         117
  Thr Cys Arg Gly Gln Val Met Gly Glu Glu Asp Ser Glu Leu Gly Asn Met Asp Pro Ile
501                                                                           560
  GTG ACC GTG AAG AAG TAC TTC CAG GGC ATC TAT GAC TAC CTG CAA GAG AAG GGA TAC AGC
  118                                                                         137
  Val Thr Val Lys Lys Tyr Phe Gln Gly Ile Tyr Asp Tyr Leu Gln Glu Lys Gly Tyr Ser
561                                                                           620
  GAC TGC GCC TGG GAA ATC GTC AGA GTC GAG ATG ATG AGA GCC CTC ACT GTA TCA ACC ACC
  138                                                                         157
  Asp Cys Ala Trp Glu Ile Val Arg Val Glu Met Met Arg Ala Leu Thr Val Ser Thr Thr
621                                                          666
  TTG CAA AAA AGG TTA ACA AAG ATG GGT GGA GAT CTG AAC TCA CCT TGATGACTCTTGCCGACTA
  158                                                172
  Leu Gln Lys Arg Leu Thr Lys Met Gly Gly Asp Leu Asn Ser Pro

764
  AGATGCCACATCAGCCTCCTACACCCGCCTGTGTTCATTTCAGAAGACTCTGATTTCTGCTCCAGCCACCAAATTCATTG

844
  AATTACTTTAGCTGATACTTTGTCAGTAGTAAAAAGCAAGTAGATATAAAAGTATTCAGCTGTAGGGGCATGAGTCCTGA

924
  AATGATGCCTTCCCTGATGTTATCTGTTGCTGATTTATTTATACCTTCTAGCATTTAACATACTTAAAATATTAGGAAAT
                                        972
  TTGTTAAGTTACATTTACATCTGTACATCATATTAAAATTTCTAAAACAAAAAAAAAA
```

Fig. 7

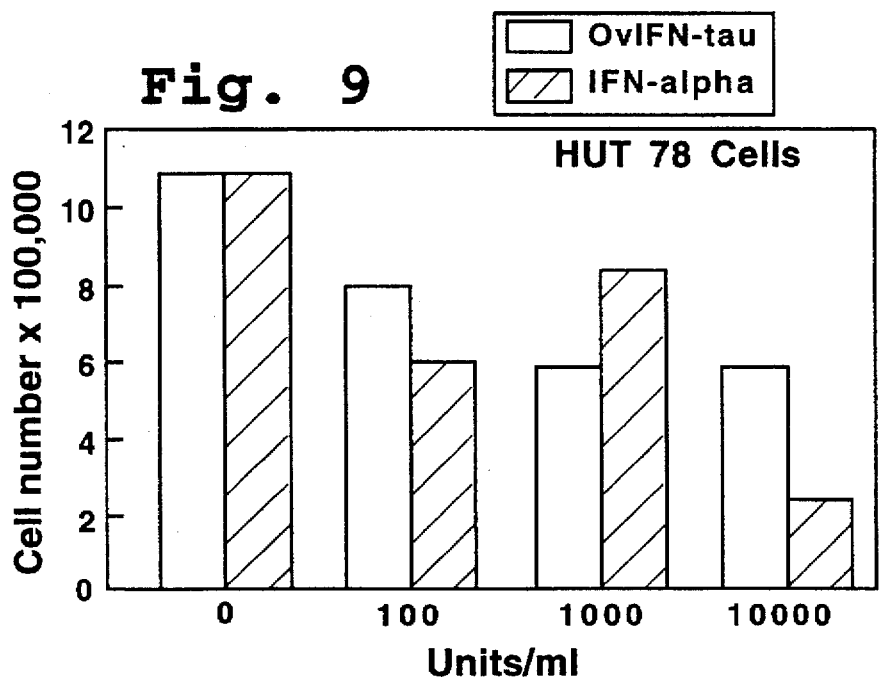
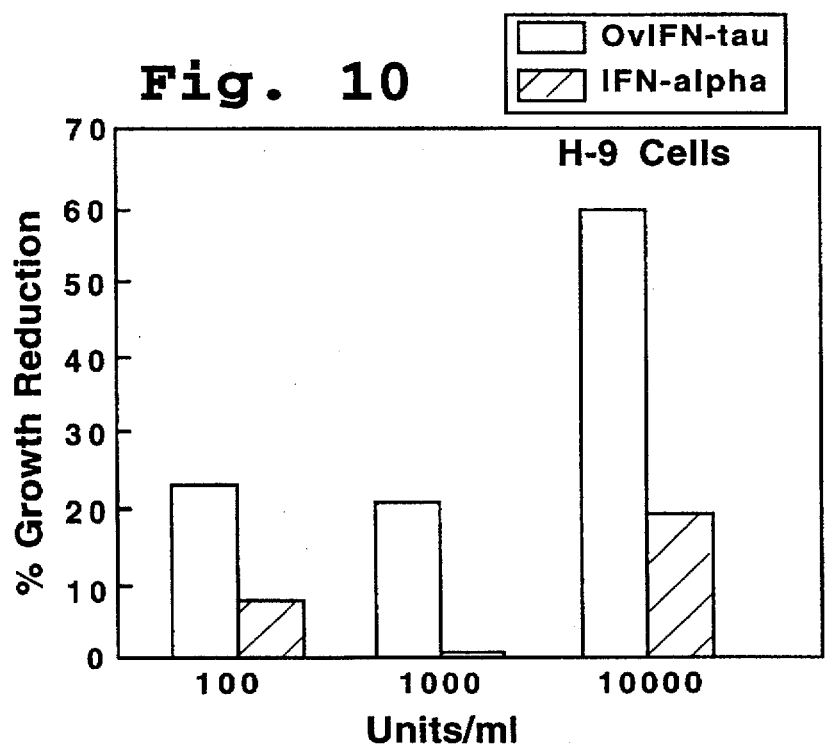

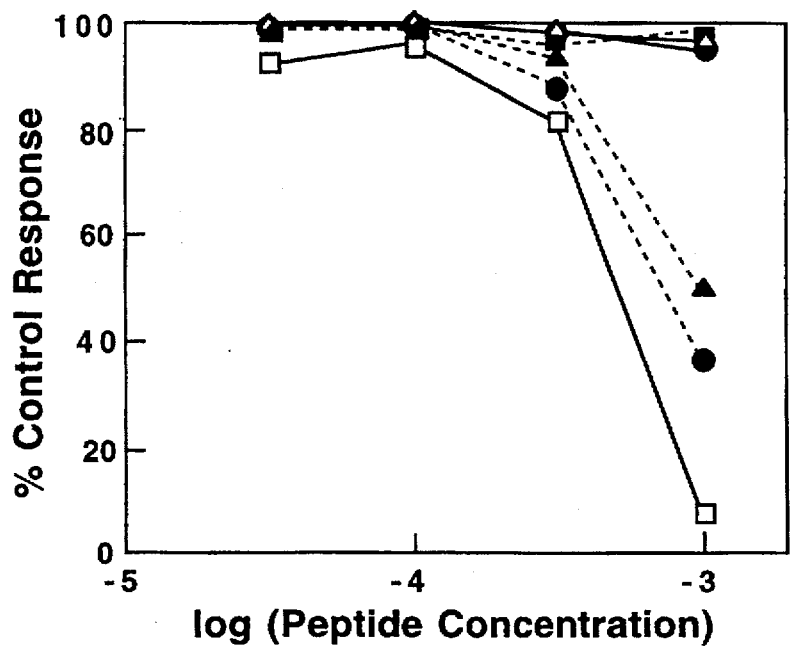
Fig. 14
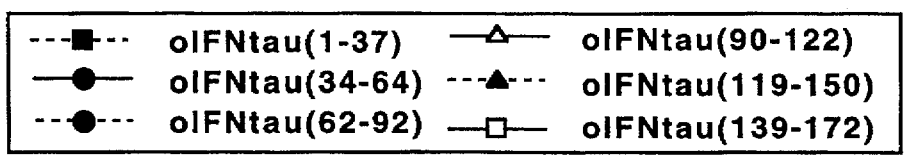
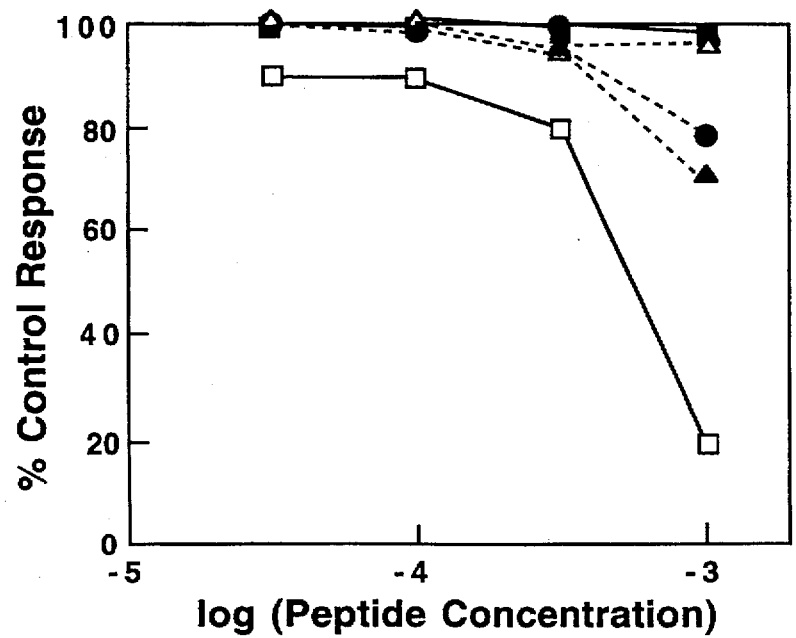
Fig. 15

```
                -23                                                                          -9
                Met ala phe val leu ser leu leu met ala leu val leu val ser
oINFt           ATG GCC TTC GTG CTC TCT CTA CTG ATG GCC CTG GTG CTG GTC AGC
HuIFNt1                                 c
HuIFNt2                                 c
HuIFNt3                                 c -8                                  -1  +1                                                   11
tyr gly pro gly gly ser leu gly cys tyr leu ser arg lys leu met leu asp ala
TAT GGC CCA GGA GGA TCT CTG GGT TGT TAC CTA TCT CGG AAA CTC ATG CTG GAT GCC
 c                   c           G        g          A   C   A   G       T   G
 c                   c       (---)G       g          A   C   A   G       T   G
 c       g           c       C G  G       g          A   C   A   G       T   G 12                                      20                                                   30
arg glu asn leu lys leu leu asp arg met asn arg leu ser pro his ser cys leu
AGG GAG AAC CTC AAG CTC CTG GAC CGA ATG AAC AGA CTC TCC CCT CAT TCC TGT CTG
     A               G           GA      GG                  GC  TT
     A               G           A       GG                  GC  TT
 C C                 G               G A GG              T   GC  T 31                                      40                                                   49
gln asp arg lys asp phe gly leu pro gln glu met val glu gly asp gln leu gln
CAG GAC AGA AAA GAC TTT GGT CTT CCC CAG GAG ATG GTG GAG GGC GAC CAG CTC CAG
                         c   C   t a         a                   G
                         c   C   t a     TAG a                   G
                         c   C   t C                         t   G
HuIFNt4                          !                           t   G
HuIFNt5                          !                           t   G
HuIFNt6                          !                               G
HuIFNt7                          !                       T   AG      T 50                                      60                                                   68
lys asp gln ala phe pro val leu tyr glu met leu gln gln ser phe asn leu phe
AAG GAC CAG GCC TTC CCT GTG CTC TAC GAG ATG CTC CAG CAG AGC TTC AAC CTC TTC
 G   C           A   T           C T
 G   C           A   T           C T
 G   C           A   T           C
 G   C           A   T           C
 G   C           A   T           C
 G   C           A   T           C   A
 G   C           A T T           C T 69                                      80                                                   87
tyr thr glu his ser ser ala ala try asp thr thr leu leu glu gln leu cys thr
TAC ACA GAG CAC TCC TCT GCT GCC TGG GAC ACC ACC CTC CTG GAG CAG CTC TGC ACT
 C                                                                       C
 C                                                                       C
 C                                                                       C
 C                                                                       C
 C                                                                       C
 C       G                                                               C
 C   A   G                                              t                CT
```

Fig. 19A

```
 88             90                                              100                     106
 gly leu gln gln gln leu asp his leu asp thr cys arg gly gln val met gly glu
 GGA CTC CAA CAG CAG CTG GAC CAC CTG GAC ACC TGC AGG GGT CAA GTG ATG GGA GAG
         T                   A         t G         CT  g       g
         T                   A         t G         CT  g       g
         T                 t G         t G         CT  g       g       C
         T                 t G         t G         CT  g       g       C
         T                 t G         t G         CT  g       g       C
         T                 t G           G         CT  g       g       C
         T                 t G         t G       t CT  g       g T     CT 107         110                                        120                     125
 glu asp ser glu leu gly asn met asp pro ile val thr val lys lys tyr phe gln
 GAA GAC TCT GAA CTG GGT AAC ATG GAC CCC ATT GTG ACC GTG AAG AAG TAC TTC CAG
         CC      a   GG  C   G           CC  C   G T C     G
         CC      a   GG  C   G           CC  C   G T C     G
         CC      a   GA  C   G           CC  C   G   A     G       t
         CC      a   GG  C   G           CC  C   G   A     C       t
         CC      a   GG  C   G           CC  C   G   A     C       t
         CC      a   GG  C   G           CC  C   G         GC
         CC      a   GG  C   G           CC  C   G         GC 126             130                                            140             144
 gly ile tyr asp tyr leu gln glu lys gly tyr ser asp cys ala trp glu ile val
 GGC ATC TAT GAC TAC CTG CAA GAG AAG GGA TAC AGC GAC TGC GCC TGG GAA ATC GTC
         C       T       A                                                  C
         C       T       A                                                  C
         C       T       A               t   t                              t
         C       T       A               t   t                      !
         C       T       A               t   !
         C       AT                                      !
         C       T                               !

145                 150                                        160         163
 arg val glu met met arg ala leu thr val ser thr thr leu gln lys arg leu thr
 AGA GTC GAG ATG ATG AGA GCC CTC ACT GTA TCA ACC ACC TTG CAA AAA AGG TTA ACA
     C G     a   C       T   T   T   TC  T   T   G         G               G
         g   a   C       T   T   T   TC  T   T   G         G               G
     C G     a   C       T   t g T   TC              G         C           G 164                     172
 lys met gly gly asp leu asn ser pro
 AAG ATG GGT GGA GAT CTG AAC TCA CCT TGA
 T       A           c       G
 T       A           c       G
 T       A           c       G
```

Fig. 19B

```
                  -23                                                              -9
oTP-1        Met ala phe val leu ser leu leu met ala leu val leu val ser
HuIFNt1
HuIFNt2
HuIFNt3

-8                           -1  +1                                               11
tyr gly pro gly gly ser leu gly cys tyr leu ser arg lys leu met leu asp ala
                                      asp         gln asn his val     val gly
                                 (---)asp         gln asn his val     val gly
                                  arg asp         gln asn his val     val gly 12                                    20                                          30
arg glu asn leu lys leu leu asp arg met asn arg leu ser pro his ser cys leu
    lys         arg              glu         arg             arg phe
    lys         arg              gln         arg             arg phe
ser gln         arg          gly gln         arg         leu arg phe 31                                    40                                          49
gln asp arg lys asp phe gly leu pro gln glu met val glu gly asp gln leu gln
                        ala                                 gly
                        ala         (Stop)                  gly
                        ala phe                             gly
HuIFNt4                         !                           gly
HuIFNt5                         !                           gly
HuIFNt6                         !                           gly
HuIFNt7                         !                                   val ser             phe 50                                    60                                          68
lys asp gln ala phe pro val leu tyr glu met leu gln gln ser phe asn leu phe
glu ala         ile ser         his
glu ala         ile ser         his
glu ala         ile ser         his
glu ala         ile ser         his
glu ala         ile ser         his
glu ala         ile ser         his lys
glu ala         ile ser         his 69                                    80                                          87
tyr thr glu his ser ser ala ala trp asp thr thr leu leu glu gln leu cys thr
his                                                                     arg
his                                                                     arg
his                                                                     arg
his                                                                     arg
his                                                                     arg
his             arg                                                     arg
his lys         arg                                                     leu
```

Fig. 20A

```
88          90                                              100                   106
gly leu gln gln gln leu asp his leu asp thr cys arg gly gln val met gly glu
                his         asn     ala     leu
                his         asn     ala     leu
                his         asp     ala     leu             thr
                his         asp     ala     leu             thr
                his         asp     ala     leu             thr
                his         asp.    ala     leu             thr
                his         asp     ala     leu         leu thr 107         110                                             120               125
glu asp ser glu leu gly asn met asp pro ile val thr val lys lys tyr phe gln
            ala         arg thr gly     thr leu ala leu     arg
            ala         arg thr gly     thr leu ala leu     arg
            ala         arg thr gly     thr leu ala met     arg
            ala         arg thr gly     thr leu ala met     thr
            ala         arg thr gly     thr leu ala met     thr
            ala         arg thr gly     thr leu ala         ser
            ala         arg thr gly     thr leu ala         ser 126         130                                             140             144
gly ile tyr asp tyr leu gln glu lys gly tyr ser asp cys ala trp glu ile val
        his val         lys                                         thr
        his val         lys                                         thr
        his val         lys
        his val         lys                             !
        his val         lys             !
        his ile                                   !
        his val                     !

145             150                                         160         163
arg val glu met met arg ala leu thr val ser thr thr leu gln lys arg leu thr
    leu     ile         ser phe ser ser leu ile ser         glu         arg
            ile         ser phe ser ser leu ile ser         glu         arg
    leu     ile         ser     ser ser         ser     his             arg 164                 172
lys met gly gly asp leu asn ser pro stop
    met     asp         ser         stop
    met     asp         ser         stop
    met     asp         ser         stop
```

Fig. 20B

HUMAN INTERFERON τ PROTEINS AND METHODS OF USE

This application is a continuation of allowed patent application Ser. No. 08/438,753, filed May 10, 1995, herein incorporated by reference, which is a continuation-in-part of patent application Ser. No. 08/139,891, filed Oct. 19, 1993, now abandoned, incorporated herein by reference, which is a continuation-in-part of patent application Ser. No. 07/847,741, filed Mar. 09, 1992, now abandoned, which is a continuation-in-part of application Ser. No. 07/318,050, filed Mar. 2, 1989, now abandoned. Application Ser. No. 08/139,891 is also a continuation-in-part of patent application Ser. No. 07/969,890, filed Oct. 30, 1992, now abandoned.

This invention was made with government support under National Institutes of Health grants HD 10436, HD 26006, CA 38587, and CA 57084. Accordingly, the United States government has certain rights in this invention.

FIELD OF THE INVENTION

The present invention relates to interferon-τ compositions and methods of use.

References

Abraham, G., et al., *Clin. Immunol. Immunopathol.* 56:1–8 (1990).
Ausubel, F. M., et al., CURRENT PROTOCOLS IN MOLECULAR BIOLOGY, John Wiley & Sons, Inc., Media, Pa.
Bayne, M. L., et al., *Gene* 66:235 (1988).
Bazer, F. W., et al., *J. Animal Sci.* 57(Supp. 2):425 (1983).
Bazer, F. W., et al., *J. Reproduction and Fertility* 76:841 (1986).
Bazer, F. W., et al., *Biology of Reproduction*, vol. 40; (Supplement 1):63, (Abstract) (1989).
Beames, et al., *Biotechniques* 11:378 (1991).
Benoit, P., et al., *J. Immunol.* 150(3):707 (1993).
Bonnem, E. M., et al., *J. Bio. Response Modifiers* 3:580 (1984).
Boyer, S. J., et al., *J. Biol. Regul. Homeost. Agents.* 6(3):99–102 (1992).
Chan, et al., *DNA* 4:165 (1985).
Crea, R., U.S. Pat. No. 4,888,286, issued Dec. 19, 1989.
Crowe, S. M., et al., *AIDS Res. Hum. Retroviruses* 3(2):135 (1987).
Cumber, J. A., et. al., *Methods in Enzymology*, 112:207 (1985).
Dalgleish, et al., *Nature* 312:763 (1984).
Davis, G. L., et al., *N. England J. Med.* 321:1501 (1989).
Davis, G. L., et al., *Theriogenology* 38:867 (1992).
Degre, M., *Int. J. Cancer* 14:699–703 (1974).
DeMaeyer, E., et al., *Interferons and Other Regulatory Cytokines*, John Wiley and Sons, New York (1988).
Dianzani, F., *J. Interferon Res.*, Special Issue, 5/92:109 (1992).
Duncan, R. J. S., et. al., *Anal Biochem*, 182:68 (1983).
Dusheiko, G. M., et al., *J. Hematology* 3(Supl. 2):S199 (1986).
Eaton, M. A. W., et al., U.S. Pat. No. 4,719,180, issued Jan. 12, 1988.
Ecker, D. J., et al., *J. Biol. Chem.* 264:7715–7719 (1989).
Elliot, S., et al., *J. Biol. Chem.* 261:2936 (1986).
Ernst, J. F., *DNA* 5:483 (1986).
Familetti, P. C., et al., *Meth. Enzymol.* 78:387 (1981).
Feher, Z., et al., *Curr. Genet.* 16:461 (1989).
Fent, K., and Zbinden, G., *Trends Pharm. Sci.* 8:100–105 (1987).
Figuero, F., et al., *Immunogenetics* 15:431 (1982).
Finter, N. B., et al., *Drugs* 42(5):749 (1991).
Foa, P., et al., *Cell Tissue Kinet.* 15(4):399–404 (1982).
Francis, M. L., et al., *AIDS Res. and Human Retroviruses* 8(2):199 (1992).
Frangioni, J. V., et al., *Anal. Biochem.* 210(1):179–187 (1993).
Fritz, R. B., et al., *J. Immunol.* 134:2328 (1985).
Godkin, J. D., et al., *J. Reprod. Fert.* 65:141 (1982).
Griggs, N. D., et al., *J. Immunol.* 149:517 (1992).
Guan, K. L., et al., *Anal. Biochem.* 192(2):262–267 (1991).
Haahr, S., et al., *The Lancet* 337:863–864 (1991).
Hakes, D. J., et al., *Anal. Biochem.* 202(2):293–298 (1992).
Hansen, P. J., et al., U.S. Pat. No. 4,997,646, issued 5 Mar. 1991.
Harlow, E., et al., *Antibodies: A Laboratory Manual*, Cold Spring Harbor Press, Cold Spring Harbor, N.Y. (1988).
Helmer, S. D., et al., *J. Reprod. Fert.* 79:83–91 (1987).
Hitzeman, R. A., et al., U.S. Pat. No. 4,775,622, issued Oct. 4, 1988.
Hoffman, A. E., et al., *Virology* 147:326 (1985).
Howatson, et al., *J. Endocrinol.* 119:531 (1988).
Imakawa, K., et al., *Nature* 330:377 (1987).
Imakawa, K., et al., *Mol. Endocrinol.* 3:127–139 (1989).
Innis, M., U.S. Pat. No. 4,975,276, issued Dec. 4, 1990.
Johnson, W. C., Jr., *Methods in Enzymology*, Vol. 210, pp. 426–447, (1992).
Kashima, H., et al., *Laryngoscope* 98:334 (1988).
Klein, J., et al., *Immunogenetics* 17:553 (1983).
Kotzin, B. L., et al., *J. Exp. Med.* 165:1237 (1987).
Krown, S. E., in "Mechanisms of Interferon Actions", (Pfeffer, L. M , ed.), CRC Press Inc., Boca Raton, Vol. II, pp. 143–178, (1987).
Kyte, J., et al., *J. Mol. Biol.* 157:105 (1982).
Langford, M. P., et al., *Meth. Enzymol.* 78:339 (1981).
Lawrence, et al., *Nucl. Acids. Res.* 13:1777 (1985).
Lowry, O. H., et al., *J. Biol. Chem.* 193265–275 (1951).
Ludwig, D. L., et al., *Gene* 132:33 (1993).
Maniatis, T., et al. *Molecular Cloning: A Laboratory Manual*, Cold Spring Harbor Laboratory (1982).
Martin, E. W., "In: Dispensing of medication: a practical manual on the formulation and dispensing of pharmaceutical products", (Hoover, J. E. ed.), 8th edition, Mack Publishing Co., Easton, Pa., (1976).
Meyer, F., et al., U.S. Pat. No. 4,885,166, issued Dec. 5, 1989.
McInnes, B., et al., *J. Interferon Res.* 9(3), pp. 305–314, (1989).
Mullis, K. B., U.S. Pat. No. 4,683,202, issued 28 Jul. 1987.
Mullis, K. B., et al., U.S. Pat. No. 4,683,195, issued 28 Jul. 1987.

Miyoshi, E., et al., *Int. J. Cancer* 52(1):137–140 (1992).

Nagy, et al., *Int. J. Canc.* 32:321 (1983).

Oeda, K., et al., U.S. Pat. No. 4,766,068, issued Aug. 23, 1988.

Oldham, R. K., *Hospital Practice* 20:71 (1985).

Paulesu, et al., *J. Biol. Regul. Homeost. Agents* 5:81 (1991).

Pearson, W. R. and Lipman, D. J., *PNAS* 85:2444–2448 (1988).

Pearson, W. R., *Methods in Enzymology* 183:63–98 (1990).

Pederson, et al., *Science* 235:790 (1987).

Perczel, A., et al., *Protein Engineering*, Vol. 4, (Supp. 6), pp. 669–679, (1991).

Perron, H., et al., *The Lancet* 337:862–863 (1991).

Pontzer, et al., *Biochem. Biophys. Res. Comm.* 152:801 (1988).

Pontzer, C. H., et al., *Cancer Res.* 51:5304 (1991).

Poste, G., et al., *Proc. Nat'l Acad. Sci., USA*, Vol. 78:6226 (1981).

Quesada, J. R., et al., *N. England J. Med.* 310:15 (1984).

Rasmussen, H. B., et al., *Acta. Neurol. Scand.* 88:190–198 (1993).

Reilly, P. R., et al., *Baculovirus Expression Vectors: A Laboratory Manual* (1992).

Roberts, R .M., et al., *Endocrine Reviews* 13:432 (1992).

Rothstein, R., *DNA Cloning: A Practical Approach*, vol. II (Glover, D. M., Ed.) Oxford: IRL Press, pp. 46–66 (1986).

Ruegg, C. L., et al., *J. Interferon Res.*, 10:621–626, (1990).

Rutter, W. J., et al., U.S. Pat. No. 4,769,238, issued Sep. 6, 1988.

Sabin, E., et al., Bio/Technology 7:705–709 (1989).

Sambrook, J., et al., *Molecular Cloning, A Laboratory Manual* (Cold Spring Harbor Laboratory, Cold Spring Harbor, N.Y.) (1989).

Sanger, et al., *Proc. Natl. Acad. Sci. USA* 74:5463 (1977).

Senda, T., et al., *EMBO J.*, Vol. 11, Supp. 9, pp. 3193–3201, (1992).

Shaw, K. J., et al., *DNA* 7:117 (1988).

Shen, L. P., et al., *Sci. Sin.* 29:856 (1986).

Shoulders, C. C., et al., *Nucleic Acids Res.* 10(16):4873–4882 (1982).

Smith, D. B., et al., *Gene* 67:31 (1988).

Smith, P. K., et at., *Anal. Biochem.* 150:76 (1985).

Stewart, H. J., et al., *J. Endocrinol.* 115:R13 (1987).

Talal, N, et al., *Annals of Allergy* 69:221–224 (1992).

Todd, R. F., et al., *Leuk. Res.* 5(6):491–495 (1981).

Vallet, J. L., et al., *Biol. Reprod.* 37:1307 (1987).

Vallet, J. L., et al., *J. Endocrinology* 117:R5–R8 (1988).

Venables, P., et al., *Brit. J. Rheumatology* 31:841–846 (1992).

von Eichborn, J. F., et al., U.S. Pat. No. 5,145,677, issued Sep. 8, 1992.

Wallis, S. C., et al., *EMBO J.* 2(12):2369–2373 (1983).

Whaley, A. E., et al., *J. Biol. Chem.* 269:10846–10868 (1994).

Wang, C. Y., et al., U.S. Pat. No. 4,879,212, issued 7 Nov. 1989.

Wang, C. Y., et al., U.S. Pat. No. 4,735,896, issue 5 Apr. 1988.

Wilson, et al., *Biology of Reproduction* 20(Supp. 1):101A, Abstract (1979).

Wraith, D. C., et al., *Cell* 59:247 (1989).

Wu, D. A., et al., *DNA* 10:201 (1991).

Yoshio, T., et al., U.S. Pat. No. 4,849,350, issued Jul. 18, 1989.

Young, et al., *Proc. Natl. Acad. Sci. USA* 80:1194 (1983).

Zamvil, S. S., et al., *Nature* 317:355 (1985).

BACKGROUND OF THE INVENTION

Conceptus membranes, or trophectoderm, of various mammals produce biochemical signals that allow for the establishment and maintenance of pregnancy (Bazer, et al., 1983). One such protein, ovine trophoblast protein-one (oTP-1), was identified as a low molecular weight protein secreted by sheep conceptuses between days 10 and 21 of pregnancy (Wilson, et al., 1979; Bazer, et al., 1986). The protein oTP-1 was shown to inhibit uterine secretion of prostaglandin $F_2$-alpha, which causes the corpus luteum on the ovary to undergo physiological and endocrinological demise in nonpregnant sheep (Bazer, et al., 1986). Accordingly, oTP-1 has antiluteolytic biological activity. The primary role of oTP-1 was assumed to be associated with the establishment of pregnancy.

oTP-1 was subsequently found to (i) exhibit limited homology (50–70%) with interferon alphas (IFN$\alpha$) of various species (Imakawa, et al., 1987), and (ii) bind to a Type I interferon receptor (Stewart, et al., 1987). Despite some similarities with IFN$\alpha$, oTP-1 has several features that distinguish it from IFN$\alpha$ including the following: oTP-1's role in reproductive biochemistry (other interferons are not known to have any role in the biochemical regulation of reproductive cycles), oTP-1's cellular source—trophoblast cells (IFN$\alpha$ is derived from lymphocyte cells), oTP-1's size—172 amino acids (IFN$\alpha$ is typically about 166 amino acids), and oTP-1 is weakly inducible by viruses (IFN$\alpha$ is highly inducible by viruses). The International Interferon Society recognizes oTP-1 as belonging to an entirely new class of interferons which have been named interferon-tau (IFN$\tau$). The Greek letter $\tau$ stands for trophoblast.

The interferons have been classified into two distinct groups: type I interferons, including IFN$\alpha$, IFN$\beta$, and IFN$\omega$ (also known as IFN$\alpha$II); and type II interferons, represented by IFN$\gamma$ (reviewed by DeMaeyer, et al.). In humans, it is estimated that there are at least 17 IFN$\alpha$ non-allelic genes, at least about 2 or 3 IFN$\beta$ non-allelic genes, and a single IFN$\gamma$ gene.

IFN$\alpha$'s have been shown to inhibit various types of cellular proliferation. IFN$\alpha$'s are especially useful against hematologic malignancies such as hairy-cell leukemia (Quesada, et al., 1984). Further, these proteins have also shown activity against multiple myeloma, chronic lymphocytic leukemia, low-grade lymphoma, Kaposi's sarcoma, chronic myelogenous leukemia, renal-cell carcinoma, urinary bladder tumors and ovarian cancers (Bonnem, et al., 1984; Oldham, 1985). The role of interferons and interferon receptors in the pathogenesis of certain autoimmune and inflammatory diseases has also been investigated (Benoit, et al., 1993).

IFN$\alpha$'s are also useful against various types of viral infections (Finter, et at., 1991). Alpha interferons have shown activity against human papillomavirus infection, Hepatitis B, and Hepatitis C infections (Finter, et al., 1991; Kashima, et al., 1988; Dusheiko, et al., 1986; Davis, et al., 1989).

Significantly, however, the usefulness of IFNα's has been limited by their toxicity: use of interferons in the treatment of cancer and viral disease has resulted in serious side effects, such as fever, chills, anorexia, weight loss, and fatigue (Pontzer, et al., 1991; Oldham, 1985). These side effects often require (i) the interferon dosage to be reduced to levels that limit the effectiveness of treatment, or (ii) the removal of the patient from treatment. Such toxicity has reduced the usefulness of these potent antiviral and antiproliferative proteins in the treatment of debilitating human and animal diseases.

SUMMARY OF THE INVENTION

In a first aspect, the present invention relates to compositions of and methods employing ovine interferon-τ. The invention includes an isolated nucleic acid molecule that encodes an ovine interferon-τ. One embodiment of this nucleic acid molecule is a nucleic acid molecule having the sequence presented as SEQ ID NO:1. In another embodiment, the nucleic acid molecule encodes an ovine interferon-τ polypeptide having a sequence presented as SEQ ID NO:2. The ovine interferon-τ polypeptide may include an amino-terminal extension, such as, a leader sequence.

In another embodiment, the present invention includes an expression vector having a nucleic acid containing an open reading frame (ORF) that encodes an ovine interferon-τ, including the nucleic acid and polypeptide sequences described above. The vector further includes regulatory sequences effective to express the open reading frame in a host cell. Further, the invention includes a method of recombinantly producing ovine interferon-τ using the expression vectors of the present invention. The expression vectors are introduced into suitable host cells. The host cells are then cultured under conditions that result in the expression of the ORF sequence.

In one embodiment, the present invention includes a recombinantly produced ovine interferon-τ protein.

Further, the invention includes a method of inhibiting tumor cell growth. In the method, the tumor cells are contacted with ovine interferon-τ at a concentration effective to inhibit growth of the tumor cells. Target tumor cells include, but are not limited to carcinoma cells, hematopoietic cancer cells, leukemia cells, lymphoma cells and melanoma cells.

The invention also includes a method of inhibiting viral replication. In this method, cells infected with a virus are contacted with ovine interferon-τ at a concentration effective to inhibit viral replication within said cells. Ovine interferon-τ may be used to inhibit the replication of both RNA and DNA viruses. Exemplary RNA viruses include feline leukemia virus, ovine progressive pneumonia virus, ovine lentivirus, equine infectious anemia virus, bovine immunodeficiency virus, visna-maedi virus, and caprine arthritis encephalitis virus.

In a second aspect, the present invention relates to compositions of and methods employing human interferon-τ's. In one embodiment, the invention includes an isolated nucleic acid molecule that encodes a human interferon-τ. Several variants of human interferon-τ (HuIFNτ) are disclosed herein, including HuIFNτ1, HuIFNτ2, HuIFNτ3, HuIFNτ4, HuIFNτ5, HuIFNτ6 and HuIFNτ7. The nucleic acid molecules of the present invention include nucleic acid molecules having the following sequences: SEQ ID NO:43, SEQ ID NO:29, SEQ ID NO:25, SEQ ID NO:33, SEQ ID NO:27, SEQ ID NO:21 and SEQ ID NO:23.

The nucleic acids of the present invention also include nucleic acid molecules encoding the following polypeptide sequences: SEQ ID NO:44, SEQ ID NO:30, SEQ ID NO:34, SEQ ID NO:26, SEQ ID NO:28, SEQ ID NO:22, and SEQ ID NO:24. The nucleic acids may further include sequences encoding leader sequences for the human interferon-T which they encode, for example, SEQ ID NO:41 or SEQ ID NO:42.

The second aspect of the invention further includes an expression vector having a nucleic acid sequence containing an open reading frame that encodes a human interferon-τ, including the nucleic acid and polypeptide sequences described above. The vector further includes regulatory sequences effective to express said open reading frame in a host cell. The regulatory sequence may include sequences useful for targeting or secretion of the human IFNτ polypeptide: such sequences may be endogenous (such as the normally occurring human IFNτ leader sequences, present, for example, in SEQ ID NO:41) or heterologous (such as a secretory signal recognized in yeast, mammalian cell, insect cell, tissue culture or bacterial expression systems). In the expression vector, regulatory sequences may also include, 5' to said nucleic acid sequence, a promoter region and an ATG start codon in-frame with the human interferon-τ coding sequence, and 3' to said coding sequence, a translation termination signal followed by a transcription termination signal.

In a further embodiment, the invention includes a method of recombinantly producing human interferon-τ. In the method, the expression vector, containing sequences encoding a human interferon-τ open reading frame (ORF), is introduced into suitable host cells, where the vector is designed to express the ORF in the host cells. The transformed host cells are then cultured under conditions that result in the expression of the ORF sequence. Numerous vectors and their corresponding hosts are useful in the practice of this method of the invention, including, lambda gt11 phage vector and *E. coli* cells. Other host cells include, yeast, mammalian cell, insect cell, tissue culture, plant cell culture, transgenic plants or bacterial expression systems.

In another embodiment, the invention includes an isolated human interferon-τ protein or polypeptide. The protein may be recombinantly produced. Further, the protein or polypeptide may include any of the following human interferon-τ sequences: SEQ ID NO:44, SEQ ID NO:30, SEQ ID NO:34, SEQ ID NO:26, SEQ ID NO:28, SEQ ID NO:22, and SEQ ID NO:24.

The invention further includes a method of inhibiting tumor cell growth. In the method, the tumor cells are contacted with a human interferon-τ polypeptide at a concentration effective to inhibit growth of the tumor cells. The human interferon-τ may be a part of any acceptable pharmacological formulation. Tumor cells whose growth may be inhibited by human interferon-τ include, but are not limited to, human carcinoma cells, hematopoietic cancer cells, human leukemia cells, human lymphoma cells, and human melanoma cells. In one embodiment, the tumor cells are steroid-sensitive tumor cells, for example, mammary tumor cells.

In yet another embodiment of the present invention, human interferon-τ polypeptides are used in a method of inhibiting viral replication. In this method, cells infected with a virus are contacted with human interferon-τ at a concentration effective to inhibit viral replication within said cells. The human interferon-τ may be a part of any acceptable pharmacological formulation. The replication of both RNA and DNA viruses may be inhibited by human interferon-τ polypeptides. Exemplary RNA viruses include human immunodeficiency virus (HIV) or hepatitis c virus (HCV). An exemplary DNA virus is hepatitis B virus (HBV).

In yet another aspect, the present invention includes a method of enhancing fertility in a female mammal. In this method, an effective mammalian fertility enhancing amount of human interferon-τ is administered to the female mammal in a pharmaceutically acceptable carrier.

The invention also includes isolated human interferon-τ polypeptides. These polypeptides are derived from the interferon-τ amino acid sequence and are typically between about 15 and 172 amino acids in length.

Also included in the invention is a fusion polypeptide that contains a human interferon-τ polypeptide that is between 15 and 172 amino acids long and derived from a human interferon-τ amino acid coding sequence, and a second soluble polypeptide. In one embodiment, human interferon-τ sequences are used in fusion constructs with other types of interferons to reduce the toxicity of the other types of interferons, for example, interferon-α and interferon-β.

The invention also includes a polypeptide composition having (a) a human interferon-τ polypeptide, where said polypeptide is (i) derived from an interferon-τ amino acid coding sequence, and (ii) between 15 and 172 amino acids long, and (b) a second soluble polypeptide. Interferon-α and interferon-β are examples of such second soluble polypeptides. This composition may be used to reduce the toxicity of the other types of interferons when the interferons are used in pharmaceutical formulations or in therapeutic applications.

The invention also includes purified antibodies that are immunoreactive with human interferon-τ. The antibodies may be polyclonal or monoclonal.

These and other objects and features of the invention will be more fully appreciated when the following detailed description of the invention is read in conjunction with the accompanying drawings.

BRIEF DESCRIPTION OF THE FIGURES

Figure 1D:
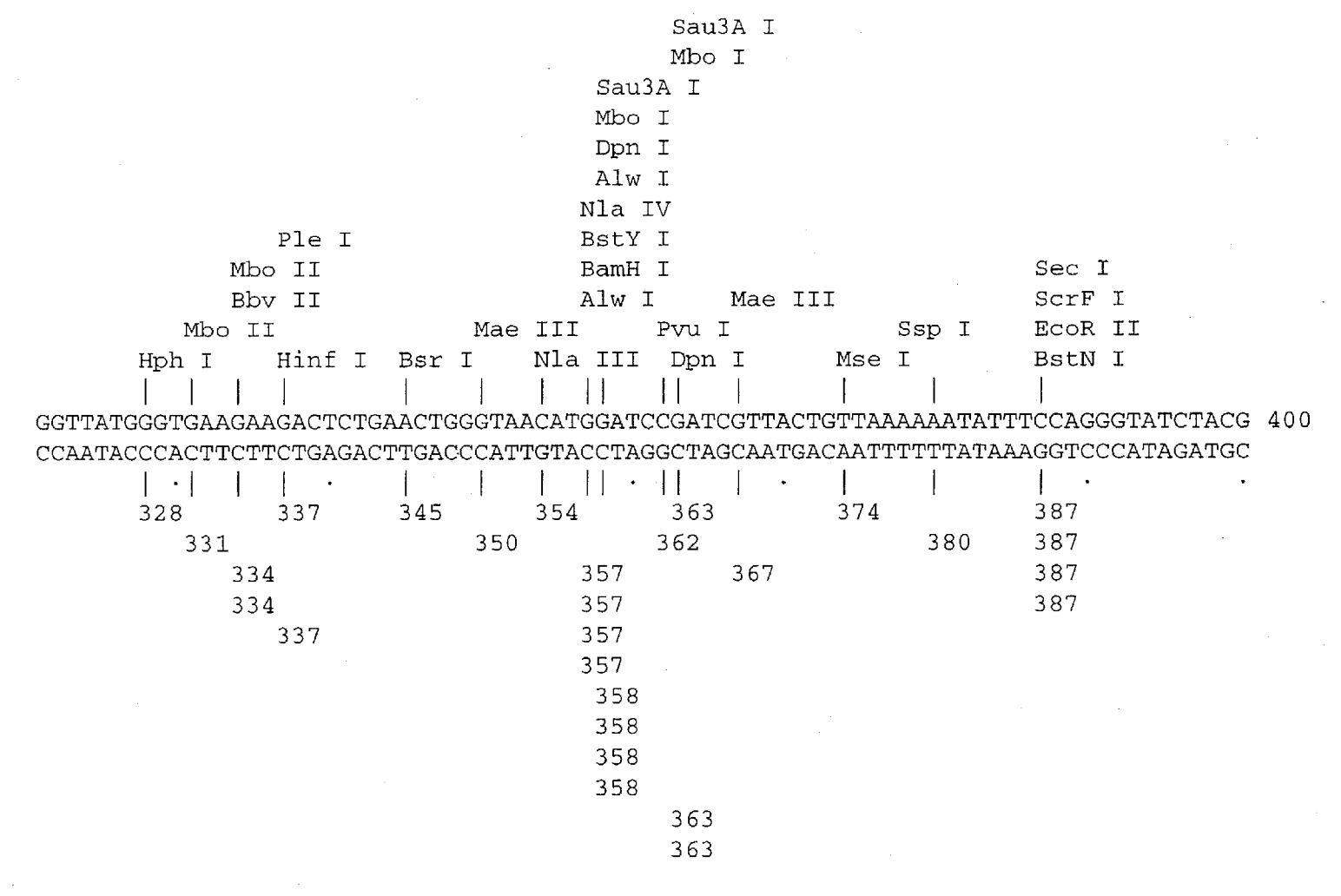
Figure 1E:
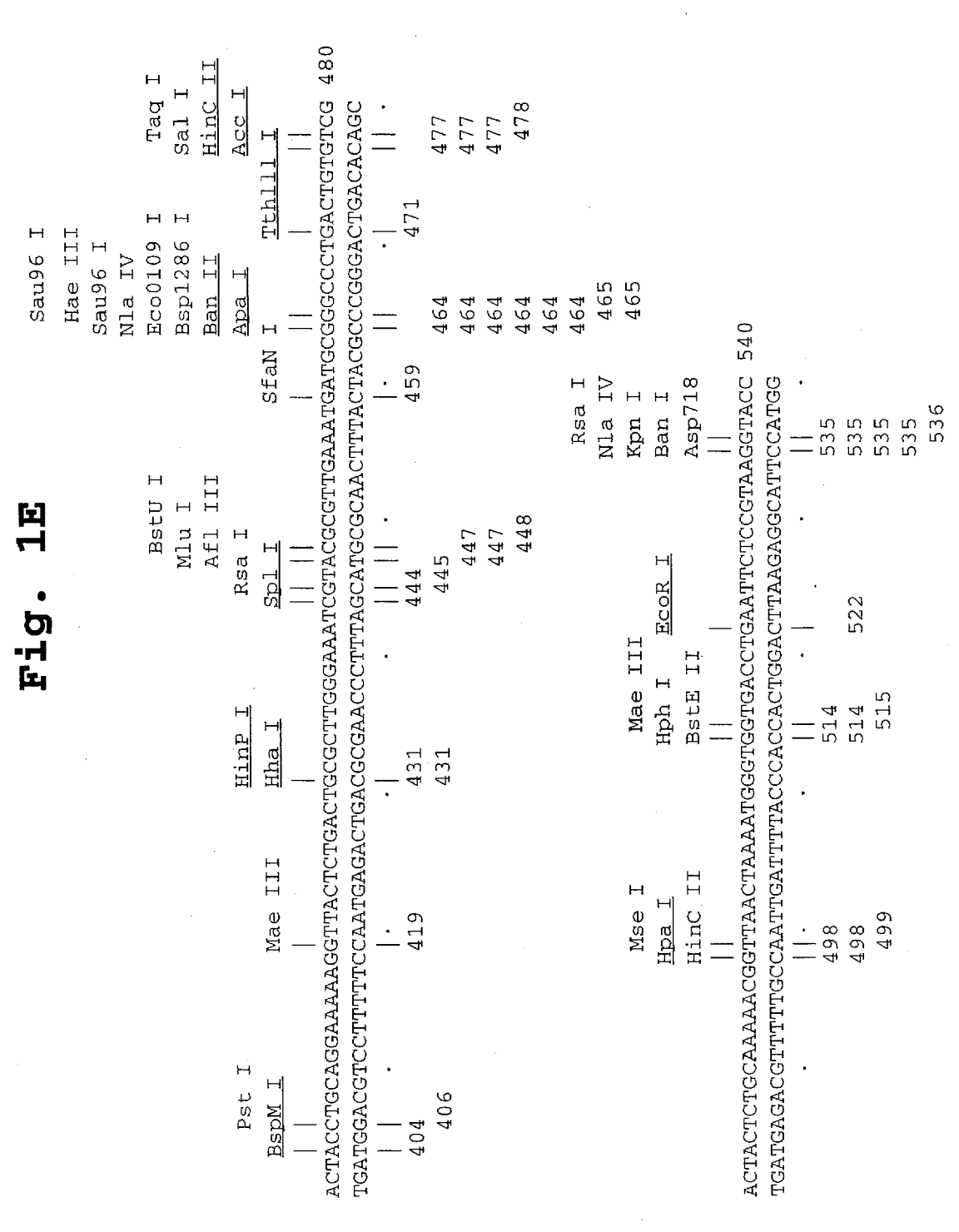

FIGS. 1A–1B present the nucleic acid coding sequence of a synthetic gene of OvIFNτ designed to include 19 unique restriction enzyme sites spaced evenly throughout the coding sequence.

FIG. 3 shows a comparison of the predicted protein sequences of a human interferon-τ gene and an ovine interferon-τ gene. Divergent amino acids are indicated by presentation of the alternative amino acid on the line below the nucleic acid sequences.

FIG. 6 presents the sequences of polypeptides derived from the IFNτ sequence.

FIG. 7 presents the complete nucleic acid and amino acid sequence of an OvIFNτ sequence.

FIG. 8 presents data supporting the lack of cytotoxicity, relative to IFNα, when IFNτ is used to treat peripheral blood mononuclear cells.

FIG. 9 shows the results of treatment of a human cutaneous T cell lymphoma line, HUT 78, with IFNτ.

FIG. 10 shows the results of treatment of a human T cell lymphoma line, H9, with IFNτ.

FIG. 14 presents data demonstrating the inhibition by IFNτ-derived peptides of bovine IFNα antiviral activity.

FIG. 15 presents data demonstrating the inhibition by IFNτ-derived peptides of human IFNα antiviral activity.

FIGS. 19A and 19B present an alignment of nucleic acid sequences encoding IFNτ polypeptides.

FIGS. 20A and 20B present an alignment of amino acid sequences of IFNτ polypeptides.

BRIEF DESCRIPTION OF THE SEQUENCES

Figure 2:
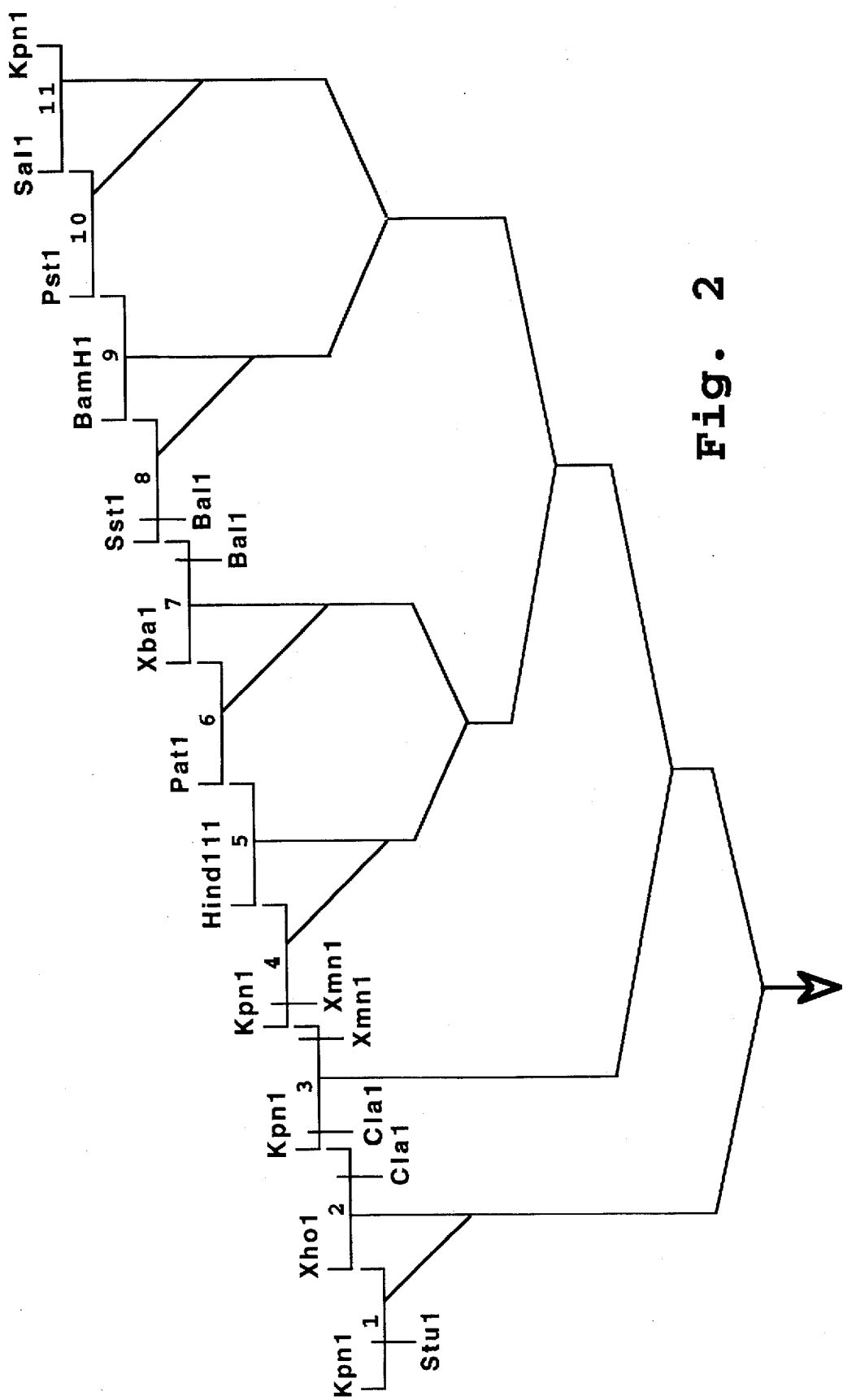
FIG. 2 shows the cloning strategy used for making a synthetic gene encoding OvIFNτ.

SEQ ID NO:1 is the nucleotide sequence of a synthetic gene encoding ovine interferon-τ (OvIFNτ). Also shown is the encoded amino acid sequence.

SEQ ID NO:2 is an amino acid sequence of a mature OvIFNτ protein.

SEQ ID NO:3 is a synthetic nucleotide sequence encoding a mature human interferon-τ (HuIFNτ) protein.

SEQ ID NO:4 is an amino acid sequence for a mature HuIFNτ1 protein.

SEQ ID NO:5 is the amino acid sequence of fragment 1-37 of SEQ ID NO:2.

SEQ ID NO:6 is the amino acid sequence of fragment 34-64 of SEQ ID NO:2.

SEQ ID NO:7 is the amino acid sequence of fragment 62-92 of SEQ ID NO:2.

SEQ ID NO:8 is the amino acid sequence of fragment 90-122 of SEQ ID NO:2.

SEQ ID NO:9 is the amino acid sequence of fragment 119-150 of SEQ ID NO:2.

SEQ ID NO:10 is the amino acid sequence of fragment 139-172 of SEQ ID NO:2.

SEQ ID NO:11 is the nucleotide sequence of a natural HuIFNτ1 gene with a leader sequence.

SEQ ID NO:12 is the predicted amino acid coding sequence of the SEQ ID NO:11.

SEQ ID NO:13 is a 25-mer synthetic oligonucleotide according to the subject invention.

SEQ ID NO:14 is a 25-mer synthetic oligonucleotide according the subject invention.

SEQ ID NO:15 is the amino acid sequence of fragment 1-37 of SEQ ID NO:4.

SEQ ID NO:16 is the amino acid sequence of fragment 34-64 of SEQ ID NO:4.

SEQ ID NO:17 is the amino acid sequence of fragment 62-92 of SEQ ID NO:4.

SEQ ID NO:18 is the amino acid sequence of fragment 90-122 of SEQ ID NO:4.

SEQ ID NO:19 is the amino acid sequence of fragment 119-150 of SEQ ID NO:4.

SEQ ID NO:20 is the amino acid sequence of fragment 139-172 of SEQ ID NO:4.

SEQ ID NO:21 is the nucleotide sequence of cDNA HuIFNτ6.

SEQ ID NO:22 is the predicted amino acid sequence encoded by the sequence represented as SEQ ID NO:21.

SEQ ID NO:23 is the nucleotide sequence of cDNA HuIFNτ7.

SEQ ID NO:24 is the predicted amino acid sequence encoded by the sequence represented as SEQ ID NO:23.

SEQ ID NO:25 is the nucleotide sequence of cDNA HuIFNτ4.

SEQ ID NO:26 is the predicted amino acid sequence encoded by the sequence represented as SEQ ID NO:25.

SEQ ID NO:27 is the nucleotide sequence of cDNA HuIFNτ5.

SEQ ID NO:28 is the predicted amino acid sequence encoded by the sequence represented as SEQ ID NO:27.

SEQ ID NO:29 is the nucleotide sequence of genomic DNA clone HuIFNτ2.

SEQ ID NO:30 is the predicted amino acid sequence encoded by the sequence represented as SEQ ID NO:29.

SEQ ID NO:31 is the nucleotide sequence, including leader sequence, of genomic DNA clone HuIFNτ3, a natural HuIFNτ gene.

SEQ ID NO:32 is the predicted amino acid sequence (including leader sequence) encoded by the sequence represented as SEQ ID NO:31.

SEQ ID NO:33 is the nucleotide sequence, excluding leader sequence, of genomic DNA clone HuIFNτ3, a natural HuIFNτ gene.

SEQ ID NO:34 is the predicted amino acid sequence of a mature human IFNτ protein encoded by HuIFNτ3, encoded by the sequence represented as SEQ ID NO:33.

SEQ ID NO:35 is the amino acid sequence of fragment 1-37 of SEQ ID NO:33.

SEQ ID NO:36 is the amino acid sequence of fragment 34-64 of SEQ ID NO:33.

SEQ ID NO:37 is the amino acid sequence of fragment 62-92 of SEQ ID NO:33.

SEQ ID NO:38 is the amino acid sequence of fragment 90-122 of SEQ ID NO:33.

SEQ ID NO:39 is the amino acid sequence of fragment 119-150 of SEQ ID NO:33.

SEQ ID NO:40 is the amino acid sequence of fragment 139-172 of SEQ ID NO:33.

SEQ ID NO:41 is the amino acid sequence of fragment 1-23 of SEQ ID NO:32.

SEQ ID NO:42 is the amino acid sequence of fragment 1-23 of SEQ ID NO:11.

SEQ ID NO:43 is the nucleotide sequence, excluding leader sequence, of DNA clone HuIFNτ1.

SEQ ID NO:44 is the predicted amino acid sequence of a mature human IFNτ protein encoded by HuIFNτ1, encoded by the sequence represented as SEQ ID NO:43.

DETAILED DESCRIPTION OF THE INVENTION

I. Definitions.

Interferon-τ (IFNτ) refers to any one of a family of interferon proteins having greater than 70%, or preferably greater than about 80%, or more preferably greater than about 90% amino acid homology to either the sequence presented as (a) SEQ ID NO:2 or (b) SEQ ID NO:34. Amino acid homology can be determined using, for example, the LALIGN program with default parameters. This program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.). Typically, IFNτ has at least one characteristic from the following group of characteristics: (a) expressed during embryonic/fetal stages by trophectoderm/placenta, (b) anti-luteolytic properties, (c) anti-vital properties, and (d) anti-cellular proliferation properties. IFNτ can be obtained from a number of sources including cows, sheep, ox, and humans.

An interferon-τ polypeptide is a polypeptide having between about 15 and 172 amino acids derived from an interferon-τ amino acid coding sequence, where said 15 to 172 amino acids are contiguous in native interferon-τ. Such 15–172 amino acid regions can also be assembled into polypeptides where two or more such interferon-τ regions are joined that are normally discontinuous in the native protein.

II. Isolation & Characterization of Interferon-τ.

A. Ovine and Bovine Interferon-τ.

1. Interferon-τ Coding Sequences.

Ovine interferon-τ (OvIFNτ) is a major conceptus secretory protein produced by the embryonic trophectoderm during the critical period of maternal recognition in sheep. One isolate of mature OvIFNτ is 172 amino acids in length (SEQ ID NO:2). The cDNA coding sequence contains an additional 23 amino acids at the amino-terminal end of the mature protein (Imakawa, et al., 1987). The coding sequence of this OvIFNτ isolate is presented as FIG. 7.

Relative to other interferons, oIFNτ shares about 45 to 68% amino acid homology with Interferon-α and the greatest sequence similarity with the interferon-ωs (IFNωs) of about 68%.

For the isolation of OvIFNτ protein, conceptuses were collected from pregnant sheep and cultured in vitro in a modified Minimum Essential Medium as described previously (Godkin, et al., 1982). Conceptuses were collected on various days of pregnancy with the first day of mating being described as Day 0. OvIFNτ was purified from conceptus culture medium essentially as described by Vallet, et al., (1987) and Godkin, et al. (1982).

The homogeneity of OvIFNτ was assessed by sodium dodecyl sulfate polyacrylamide gel electrophoresis (SDS-PAGE; Maniatis, et al.; Ausubel, et al.). Determination of protein concentration in purified OvIFNτ samples was performed using the bicinchoninic (BCA) assay (Pierce Chemical Co., Rockford, Ill.; Smith, et al., 1985).

A homologous protein to OvIFNτ was isolated from cows (BoIFNτ; Helmer, et al., 1987; Imakawa, et al., 1989). OvIFNτ and BoIFNτ (i) have similar functions in maternal recognition of pregnancy, and (ii) share a high degree of amino acid and nucleotide sequence homology between mature proteins. The nucleic acid sequence homology between OvIFNτ and BoIFNτ is 76.3% for the 5' non-coding region, 89.7% for the coding region, and 91.9% for the 3' non-coding region. The amino acid sequence homology is 80.4%.

Example 1 describes the reproductive functions of OvIFNτ. OvIFNτ and recombinant human Interferon-α2 (rHuIFNα) were infused into uterine lumen of ewes at a variety of concentrations. The life span of the corpus luteum was assessed by examination of interestrous intervals, maintenance of progesterone secretion, and inhibition of prostaglandin secretion (Davis, et al., 1992). Comparison of the data resulting from these examinations demonstrated a considerable lengthening of the interestrous interval when OvIFNτ is administered at 100 μg/day and no meaningful effect when rHuIFNα is administered. These data support the conclusion that OvIFNτ significantly influences the biochemical events of the estrous cycle.

The antiviral properties of interferon-τ at various stages of the reproductive cycle were also examined (Example 2). Conceptus cultures were established using conceptus obtained from sheep at days 12 through 16 of the estrus cycle. Antiviral activity of supernatant from each conceptus culture was assessed. Culture supernatants had increasing antiviral activity associated with advancing development of the conceptus up to Day 16 post estrus.

2. Recombinant Production of IFNτ

Recombinant OvIFNτ was produced using bacterial and yeast cells. The amino acid coding sequence for OvIFNτ was used to generate a corresponding DNA coding sequence with codon usage optimized for expression in *E. coli* (Example 3). The DNA coding sequence was synthetically constructed by sequential addition of oligonucleotides. Cloned oligonucleotides were fused into a single polynucleotide using the restriction digestions and ligations outlined in FIG. 2. The polynucleotide coding sequence had the sequence presented as SEQ ID NO:1.

For expression of recombinant OvIFNτ, this synthetic coding sequence can be placed in a number of bacterial expression vectors: for example, lambda gt11 (Promega, Madison Wis.); pGEX (Smith, et al.); pGEMEX (Promega); and pBS (Stratagene, La Jolla Calif.) vectors. Other bacterial expression vectors containing suitable promoters, such as the T7 RNA polymerase promoter or the tac promoter, may also be used. Cloning of the OvIFNτ synthetic polynucleotide into a modified pIN III omp-A expression vector is described in Example 3. Production of the OvIFNτ protein was induced by the addition of IPTG. Soluble recombinant IFNτ was liberated from the cells by sonication or osmotic fractionation.

The protein can be further purified by standard methods, including size fractionation (column chromatography or preoperative gel electrophoresis) or affinity chromatography (using, for example, anti-OvIFNτ antibodies (solid support available from Pharmacia, Piscataway N.J.). Protein preparations can also be concentrated by, for example, filtration (Amicon, Danvers, Mass.).

The synthetic OvIFNτ gene was also cloned into the yeast cloning vector pBS24Ub (Example 4; Sabin, et al.; Ecker, et al.). Synthetic linkers were constructed to permit in-frame fusion of the OvIFNτ coding sequences with the ubiquitin coding sequences in the vector. The resulting junction allowed in vivo cleavage of the ubiquitin sequences from the OvIFNτ sequences.

The recombinant plasmid pBS24Ub-IFNτ was transformed into the yeast *S. cerevisiae*. Transformed yeast cells were cultured, lysed and the recombinant IFNτ (r-IFNτ) protein isolated from the cell lysates.

The amount of r-IFNτ was quantified by radioimmunoassay. Microsequencing of the purified r-IFNτ was carried out. The results demonstrated identity with native OvIFNτ through the first 15 amino acids. The results also confirmed that the ubiquitin/IFNτ fusion protein was correctly processed in vivo.

Recombinant IFNτ obtained by this method exhibited antiviral activity similar to the antiviral activity of IFNτ purified from conceptus-conditioned culture medium.

Other yeast vectors can be used in the practice of the present invention. They include 2 micron plasmid vectors (Ludwig, et al.), yeast integrating plasmids (YIps; e.g., Shaw, et al.), YEP vectors (Shen, et al.), yeast centromere plasmids (YCps; e.g., Ernst), and the like. Preferably, the vectors include an expression cassette containing an effective yeast promoter, such as the MFα1 promoter (Ernst, Bayne, et al.), GADPH promoter (glyceraldehyde-3-phosphate-dehydrogenase; Wu, et al.), the galactose-inducible GAL10 promoter (Ludwig, et al., Feher, et al., Shen, et al.), or the methanol-regulated alcohol oxidase (AOX) promoter (Tschopp, et al.). The AOX promoter is particularly useful in *Pichia pastoris* host cells (for example, the AOX promoter is used in pHIL and pPIC vectors included in the Pichia expression kit, available from invitrogen, San Diego, Calif.).

The expression cassette may include additional elements to facilitate expression and purification of the recombinant protein, and/or to facilitate the insertion of the cassette into a vector or a yeast chromosome. For example, the cassette may include a signal sequence to direct secretion of the protein. An exemplary signal sequence suitable for use in a variety of yeast expression vectors is the MFα1 pre-pro signal sequence (Bayne, et al., Ludwig, et al., Shaw, et al.). Other signal sequences may also be used. For example, the PhoI signal sequence (Elliot, et al.) is particularly effective in *Pichia Pastoris* and *Schizosaccharomyces pombe* host cells.

Exemplary expression cassettes include (i) a cassette containing (5' to 3') the AOX promoter, the PhoI signal sequence, and a DNA sequence encoding OvIFNτ, for expression in *P. pastoris* host cells, and (ii) a cassette containing (5' to 3') the MFα1 promoter, the MFα1 pre-pro signal sequence, and a DNA sequence encoding IFNτ, for expression in *S. cerevisiae* host cells.

Additional yeast vectors suitable for use with the present invention include, but are not limited to, other vectors with regulatable expression (Hitzeman, et al.; Rutter, et al.; Oeda, et al.). The yeast transformation host is typically *Saccharomyces cerevisiae*, however, as illustrated above, other yeast suitable for transformation can be used as well (e.g., *Schizosaccharomyces pombe, Pichia pastoris* and the like).

The DNA encoding the IFNτ polypeptide can be cloned into any number of commercially available vectors to generate expression of the polypeptide in the appropriate host system. These systems include the above described bacterial and yeast expression systems as well as the following: baculovirus expression (Reilly, et al.; Beames, et al.; Clontech, Palo Alto Calif.); plant cell expression, transgenic plant expression (e.g., S. B. Gelvin and R. A. Schilperoot, *Plant Molecular Biology,* 1988), and expression in mammalian cells (Clontech, Palo Alto Calif.; Gibco-BRL, Gaithersburg Md.). These recombinant polypeptides can be expressed as fusion proteins or as native proteins. A number of features can be engineered into the expression vectors, such as leader sequences which promote the secretion of the expressed sequences into culture medium. The recombinantly produced polypeptides are typically isolated from lysed cells or culture media. Purification can be carried out by methods known in the art including salt fractionation, ion exchange chromatography, and affinity chromatography. Immunoaffinity chromatography can be employed, as described above, using antibodies generated based on the INFτ polypeptides.

B. Human Interferon-τ

1. Identification and Cloning of Human Genomic Sequences Encoding an interferon-τ Protein.

Human genomic DNA was screened for sequences homologous to interferon-τ (Example 5). Several sequences that hybridized with the OvIFNτ cDNA probe were identified. Several clones containing partial sequences of human interferon-τ were then isolated (Example 6). Two synthetic 25-mer oligonucleotides, corresponding to sequences from the OvIFNτ cDNA (Imakawa, et al., 1987; Whaley, et al., 1994) were synthesized. These primers were employed in amplification reactions using DNA derived from the following two cDNA libraries: human placenta and human cytotrophoblast cells isolated from term placenta. The resulting amplified DNA fragments were electrophoretically separated and a band containing human IFNτ amplification products was isolated. The amplification products were subcloned and the inserted amplification products sequenced using the dideoxy termination method.

Comparison of sequences from five of these clones revealed a high degree of sequence homology between the isolates, but the sequences were not identical. This result suggests the existence of multiple variants of human interferon-τ genes. Analysis of the nucleotide and protein sequences suggests that human interferon-τ genes may be classified on the basis of sequence homology into at least three groups. The groups are presented below.

Example 7 describes the isolation of several full-length human IFNτ genes. High molecular weight DNA was isolated from human peripheral blood mononuclear cells (PBMCs) and size-fractionated. Fractions were tested for the presence of IFNτ sequences using polymerase chain reaction: DNA molecules from fractions that tested amplification positive were used to generate a subgenomic library in λgt11.

This subgenomic library was plated and hybridized with an OvIFNτ cDNA probe (Example 7A). Approximately 20 clones were identified that hybridized to the probe. Plaques corresponding to the positive clones were passaged, DNA isolated and analyzed by amplification reactions using OvIFNτ primers. Of these twenty plaques, six plaques generated positive PCR signals. The phage from these six clones were purified and the inserts sequenced. One of the inserts from one of these six clones was used as a hybridization probe in the following screening.

Recombinant phage from the λgt11 subgenomic library were screened using the hybridization probe just described (Example 7B). Five clones giving positive hybridization signals were isolated and the inserts sequenced. The sequences from three of the clones overlapped, and the resulting consensus nucleic acid sequence (HuIFNτ1) is presented as SEQ ID NO:11 with the predicted protein coding sequence presented as SEQ ID NO:12. The predicted mature protein coding sequence is presented as SEQ ID NO:4. The sequences from the other two clones are presented as SEQ ID NO:29 (HuIFNτ2) and SEQ ID NO:31 (HuIFNτ3). The predicted mature amino acid sequence from HuIFNτ2 is presented as SEQ ID NO:30. The predicted amino acid sequence from HuIFNτ3 is presented as SEQ ID NO:32, and the mature amino acid sequence as SEQ ID NO:34.

Comparison of the predicted protein sequences (FIG. 3) of one of the human interferon-τ genes (SEQ ID NO:4) and the ovine interferon-τ gene demonstrates the levels of sequence homology and divergence at the amino acid level.

An alignment of the nucleic acid sequences of the seven human interferon-τ nucleic acid sequences, described herein (Examples 6 and 7), with ovine interferon-τ is shown in FIGS. 19A and 19B. Sequences of OvIFNτ (oIFNτ), HuIFNτ1, HuIFNτ2, and HuIFNτ3 start at the upper left corner of FIG. 19A with the initiation ATG codon and continue through the second page of the figure. Sequences of HuIFNτ4, HuIFNτ5, HuIFNτ6 and HuIFNτ7 start approximately half-way down FIG. 19A with the CAG codon at amino acid position 40 (to the right of the exclamation marks) and continue through the second page of the figure. The 5' and 3' ends of each of the clones for HuIFNτ4, HuIFNτ5, HuIFNτ6 and HuIFNτ7 are represented by exclamation marks.

The complete coding sequence of OvIFNτ is presented in the top row of each aligned set. Nucleotides in the other sequences are indicated only at positions where they differ from those of OvIFNτ. Lower case letters represent nucleotide changes that do not result in amino acid changes, while upper case letters represent those changes that result in an amino acid substitution.

An alignment of the seven corresponding amino acid sequences, constructed in essentially the same manner as described above, is presented in FIGS. 20A and 20B. As above, the complete amino acid sequence of OvIFNτ is presented in the top row, and amino acids of other sequences are indicated only at positions where they differ from the ovine sequence.

An examination of the alignments reveals that the seven sequences may be grouped into at least three groups. Group I contains HuIFNτ1 and HuIFNτ2, group II contains HuIFNτ3, HuIFNτ4 and HuIFNτ5, and group III contains HuIFNτ6 and HuIFNτ7. These groups may represent families of interferon-τ genes having distinct cellular functions.

These groupings were established based on the following criteria. In mature proteins, Group I HuIFNτs have an asparagine (ASN) at amino acid position number 95 (numbers in reference to FIGS. 20A to 20B), a methionine (MET) at amino acid position number 104, and a leucine (LEU) at amino acid position number 120; Group II HuIFNτs have an aspartic acid (ASP) at amino acid position number 95, a threonine (THR) at amino acid position number 104, and a methionine (MET) at amino acid position number 120; and Group III HuIFNτs have an arginine (ARG) at amino acid position number 72, a valine (VAL) at amino acid position number 120, and a serine (SER) at amino acid position number 122.

The nucleic acid and polypeptide human IFNτ sequences presented as SEQ ID NO:3, SEQ ID NO:4, SEQ ID NO:11, SEQ ID NO:12, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34 can be used as the source for specific primers and probes to detect isolates of further human IFNτ coding sequences and/or pseudogenes. Further, as described above, there may be more than one isoform of the IFNτ protein and more than one coding sequence per species. The specific nucleic acid probes used in the practice of the present invention and antibodies reactive with the IFNτ polypeptides of the present invention may be useful to isolate unidentified variants of interferon-τ in mammals, according to the methods of the invention disclosed herein.

2. Characterization of the Expression of Interferon-τ in Human Tissues.

Human placental cDNA libraries and an ovine cDNA library were analyzed by hybridization to the OvIFNτ cDNA probe (Example 8). This DNA hybridization analysis suggested that the IFNτ-signals from human cDNA libraries were approximately 1/100 of the signal obtained using the ovine cDNA library. OvIFNτ cDNAs constitute around 0.4% of the ovine cDNA library. Accordingly, the abundance of human cDNAs responding to the OvIFNτ probe appears to be low, at least in the term placenta from which the cDNA libraries were generated.

The presence of HuIFNτ mRNA in human term placenta and amniocytes were also analyzed. The results suggest the presence of HuIFNτ mRNA in the feto-placental annex. The aminocytes also expressed the messages corresponding to OvIFNτ primers and human probe, suggesting that the expression of IFNτ mRNA is not limited to the term placenta.

In addition, a RT-PCR analysis for the presence of HuIFNτ was applied to the total cellular RNA isolated from human adult lymphocytes: the results suggest that IFNτ mRNA exists in lymphocytes.

The expression of interferon-τ in human tissue was also examined using in situ hybridization (Example 9). Sections from four healthy, different term and first trimester human placentas were examined. This analysis employed a cDNA probe derived from the OvIFNτ cDNA sequences (Example 9B). In situ hybridization was performed using an anti-sense RNA probe. In three separate experiments, specific hybridization was observed in all term and first trimester placental tissues.

First trimester placental villi (composed of an outer layer of syncytiotrophoblast, an underlying layer of cytotrophoblast, and a central stromal region with various types of mesenchymal cells) displayed the highest transcript level of IFNτ in the cytotrophoblast cells. Less intense but detectable levels were present in both the syncytiotrophoblast and stromal cells. A similar pattern of transcript expression was demonstrated in the placental villi of term tissue but the level of signal detection was low. First trimester extravillous trophoblasts displayed the highest amount of message and stained positive when present in the maternal blood spaces within the decidua.

Howatson, et al., (1988) noted IFNα production in the syncytiotrophoblast of chorionic villi in both first trimester and term tissues. Also, Paulesu, et al. (1991) observed IFNα in extravillous trophoblast as well as syncytiotrophoblasts, noting more intense and abundant reactivity in first trimester placental tissue when compared to those taken at term. These investigators employed antibodies raised against human IFNα subtypes, and none observed any IFNα in the villous cytotrophoblasts.

The present results demonstrate that the human IFNτ gene is highly expressed in early placental tissues by migrating extravillous trophoblasts, but is also expressed in villous syncytiotrophoblasts, cytotrophoblasts, and various stromal cells. These results demonstrate the detection of IFNτ transcripts in human pregnancy tissues, and IFNτ expression in the villous cytotrophoblasts as well as the extravillous trophoblast of first trimester placenta.

C. Antiviral Properties of Interferon-τ.

The antiviral activity of OvIFNτ has been evaluated against a number of viruses, including both RNA and DNA viruses. The relative specific activity of OvIFNτ, purified to homogeneity, was evaluated in antiviral assays (Example 10). OvIFNτ had a higher specific antiviral activity than either rBoIFNα or rBoIFNγ (Example 10, Table 3).

One advantage of the present invention is that OvIFNτ has potent antiviral activity with limited cytotoxic effects. Highly purified OvINFτ was tested for anti-retroviral and cytotoxic effects on peripheral blood lymphocytes exposed to feline AIDS and human AIDS retroviruses (Bazer, F. W., et al., 1989). The feline AIDS lentivirus produces a chronic AIDS-like syndrome in cats and is a model for human AIDS (Pederson, et al., 1987). Replication of either virus in peripheral blood lymphocytes (PBL) was monitored by reverse transcriptase (RT) activity in culture supernatants over time.

To determine IFNτ antiviral activity against FIV and HIV, RNA-dependent DNA polymerase RT activity was assayed in FIV- and HIV-infected feline and human PBL cultures treated with OvINFτ (Example 11). Replication of FIV was reduced to about one-third of control values when cells were cultured in the presence of OvIFNτ. Addition of OvIFNτ produced a rapid, dose-dependent decrease in reverse transcriptase (RT) activity (Example 11, Table 4). While concentrations as low as 0.62 ng/ml of IFNτ inhibited viral replication, much higher concentrations (40 ng/ml) having greater effects on RT-activity were without toxic effects on the cells. The results suggest that replication of the feline immunodeficiency virus was reduced significantly compared to control values when cells were cultured in the presence of OvIFNτ.

IFNτ appeared to exert no cytotoxic effect on the cells hosting the retrovirus. This was true even when IFNτ was present at 40 ng per ml of culture medium. This concentration of IFNτ is equivalent to about 8,000 antiviral units of alpha interferon—when OvIFNτ and HuIFNα are each assayed for their ability to protect Madin-Darby bovine kidney cells from lysis by vesicular stomatitis virus (lysis assay as described by Pontzer, et al., 1988).

IFNτ was also tested for activity against HIV replication in human cells. Human peripheral lymphocytes, which had been infected with HIV were treated with varying concentrations of IFNτ (Example 12). Replication of HIV in peripheral blood lymphocytes was monitored by reverse transcriptase activity in culture supernatants over time. Over a range of concentrations of IFNτ produced significant anti-HIV effects (Example 12, Table 5). A concentration of only 10 ng/ml resulted in over a 50% reduction in RT activity after only six days. A concentration of 500 ng/ml resulted in a 90% reduction in RT activity within 10 days. Further, there was no evidence of any cytotoxic effects attributable to the administration of IFNτ (Example 12, Table 5).

Further, the antiviral effects of IFNτ against HIV were evaluated by treating human PBMC cells with various amounts of either recombinant IFNτ or recombinant human IFNα at the time of infection with HIV (Example 18). The data from these experiments (Example 18, Table 11) support the conclusion that, at similar concentrations, IFNα and IFNτ are effective in reducing the replication of HIV in human lymphocytes. However, treatment of cells with IFNα resulted in cytotoxicity, whereas no such cytotoxicity was observed with treatment using IFNτ, even when IFNτ was used at much higher concentrations. No cytotoxicity was observed using IFNτ, even when INFτ was used at 200 times the dosage of interferon-alpha II.

Both FIV and HIV reverse transcriptase themselves were unaffected by IFNτ in the absence of PBL. Therefore, the antiviral activity is not due to a direct effect on the viral RT.

Interferon-τ has also been shown to inhibit Hepatitis B Virus DNA replication in hepatocytes (Example 18). A human cell line derived from liver cells transfected with Hepatitis B Virus (HBV) was used to test the antiviral effects of IFNτ. The cells were treated with both the IFNα and IFNτ over a range of concentrations. Both IFNα and IFNτ reduced DNA production by approximately two-fold compared to the no interferon control.

To demonstrate that the effect of the interferons was specific to the infecting virus and not the result of an effect on general cell metabolism, the hepatocytes were examined for the effects of IFNα and IFNτ on hepatospecific mRNA production (Example 18). Two hepatocyte specific proteins, Apo E and Apo A1, were detected by hybridization analysis. There was no apparent reduction of mRNA production for either hepatospecific mRNA at concentrations up to 40,000 units/ml of either IFNα or IFNτ. Further, no evidence for hepatotoxicity with IFNτ was seen in this assay.

The effects of recombinant ovine interferon tau (roIFNτ) on ovine lentivirus replication (OvLV) were also evaluated. In vitro effects were assayed by infecting goat synovial membrane cells with serial dilutions of OvLV. The infected cells were treated daily with roIFNτ (0–2,500 antiviral units/ml [AVU/ml]) for 6 to 12 days, and virus replication and cytopathic effect (CPE; e.g., as in Example 2) were evaluated.

Evaluation methods included vital growth curves, cell proliferation assay (e.g., as in Examples 13, 14 or 15), syncytia formation assay (e.g., as in Nagy, et al., Dalgleish, et al.), and quantitation of proviral DNA by PCR and reverse transcriptase assay (Mullis, Mullis, et al.). A reduction (p<0.001) of OvLV titer and CPE (80–99%) was observed in the roIFNτ-treated cultures.

In vivo effects of roIFNτ were assayed by inoculating twenty-four newborn lambs with $5 \times 10^6$ TCID$_{50}$ of OvLV strain 85/34. Eleven of these lambs were treated with $10^5$–$10^6$ AVU/Kg of roIFNτ once a day for 30 days post-inoculation (PI) and twice a week thereafter. Thirteen lambs were used as controls. Virus titers in blood, as determined by an end point dilution method, peaked at 4–6 weeks PI in both groups. OvLV titers in roIFNτ-treated lambs were reduced relative to control animals. The largest reduction, a 90% decrease in OvLV titer in treated animals relative to control animals (p<0.01), was obtained 4 weeks PI.

The OvLV studies described above indicate that recombinant ovIFNτ can significantly reduce OvLV replication, and suggest that IFNτ may be used to control clinical diseases caused by lentivirus infections. Taken together with the other antiviral data, these results suggest that IFNτ is an effective antiviral agent against a wide variety of viruses, including both RNA and DNA viruses.

Ovine interferon-τ may be useful in veterinary applications including, but not limited to, the treatment of the following viral diseases: feline leukemia virus, ovine progressive pneumonia virus, ovine lentivirus, equine infectious anemia virus, bovine immunodeficiency virus, visna-maedi virus, and capfine arthritis encephalitis.

Human interferon-τ may be used for the treatment of, for example, the following viral diseases: human immunodeficiency virus (HIV), hepatitis c virus (HCV) and hepatitis B virus (HBV).

D. Antiproliferative Properties of IFNτ.

The effects of IFNτ on cellular growth have also been examined. In one analysis, anti-cellular growth activity was examined using a colony inhibition assay (Example 13). Human amnion (WISH) or MDBK cells were plated at low cell densities to form colonies originating from single cells. Dilutions of interferons were added to triplicate wells and the plates were incubated to allow colony formation. IFNτ inhibited both colony size and number in these assays. IFNτ was more effective at inhibiting cell proliferation of the human cell line (WISH) than human IFNα. The antiproliferative activity of IFNτ was dose-dependent. High concentrations of IFNτ stopped proliferation, while cell viability was not impaired.

Based on cell cycle analysis, using flow cytometry, IFNτ appears to inhibit progress of cells through S phase. These results demonstrate the antiproliferative effect of IFNτ, and underscore its low cytotoxicity.

The antiproliferative effects of IFNτ were also studied for rat and bovine cell lines (Example 14). The rate of $^3$H-thymidine incorporation was used to assess the rate of cellular proliferation. The data obtained demonstrate that IFNτ drastically reduced the rate of cellular proliferation (Example 14, Table 7) for each tested cell line.

The antiproliferative activity and lack of toxicity of IFNτ was further examined using a series of human tumor cell lines (Example 15). A variety of human tumor cell lines were selected from the standard lines used in NIH screening procedure for antineoplastic agents (Pontzer, C. H., et al., (1991)). At least one cell line from each major neoplastic category was examined.

The following cell lines were obtained from American Type Culture Collection (12301 Parklawn Dr., Rockville Md. 20852):

| | |
|---|---|
| NCI-H460 | human lung large cell carcinoma; |
| DLD-1 | human colon adenocarcinoma; |
| SK-MEL-28 | human malignant melanoma; |
| ACHN | human renal adenocarcinoma; |
| HL-60 | human promyelocytic leukemia; |
| H9 | human T cell lymphoma; |
| HUT 78 | human cutaneous T cell lymphoma; and |
| MCF7 | human breast adenocarcinoma. |

As above, the antiproliferative activity was evaluated by measuring the rate of $^3$H-thymidine incorporation into cells which have been treated with IFNτ. Significant differences between treatments were assessed by an analysis of variance followed by Scheffe's F-test. Cell cycle analysis was performed by flow cytometry.

Examination of IFNτ inhibition of MCF7 (breast adenocarcinoma) proliferation demonstrated that IFNτ reduced MCF7 proliferation in a dose-dependent manner. A 50% reduction in $^3$H-thymidine was observed with 10,000 units/ml of IFNτ (Example 15, Table 8). This cell line had previously been found to be unresponsive to anti-estrogen treatment.

Figure 4:
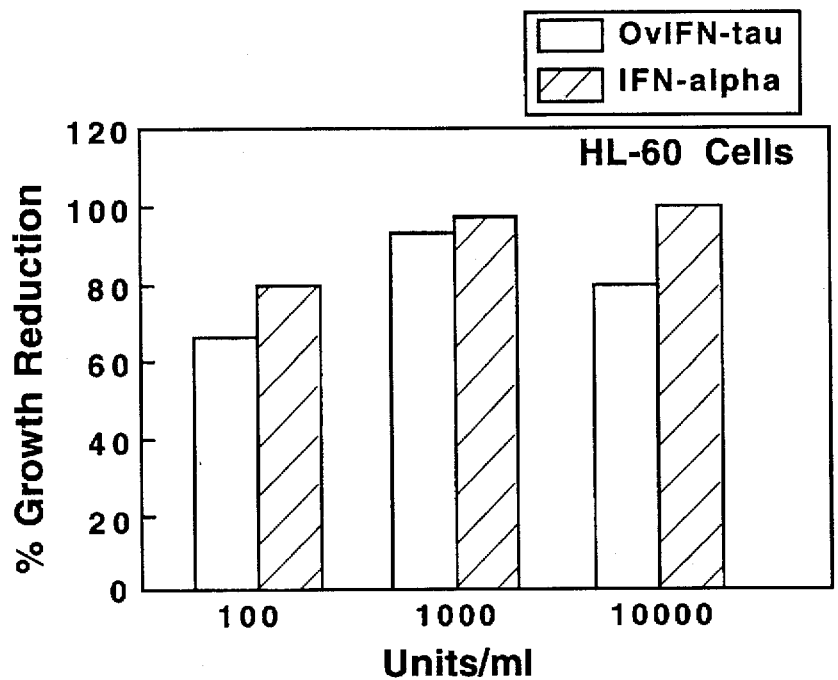
FIG. 4 presents data demonstrating that both OvIFNτ and IFNα were able to drastically reduce growth of HL-60 cells.
Figure 5:
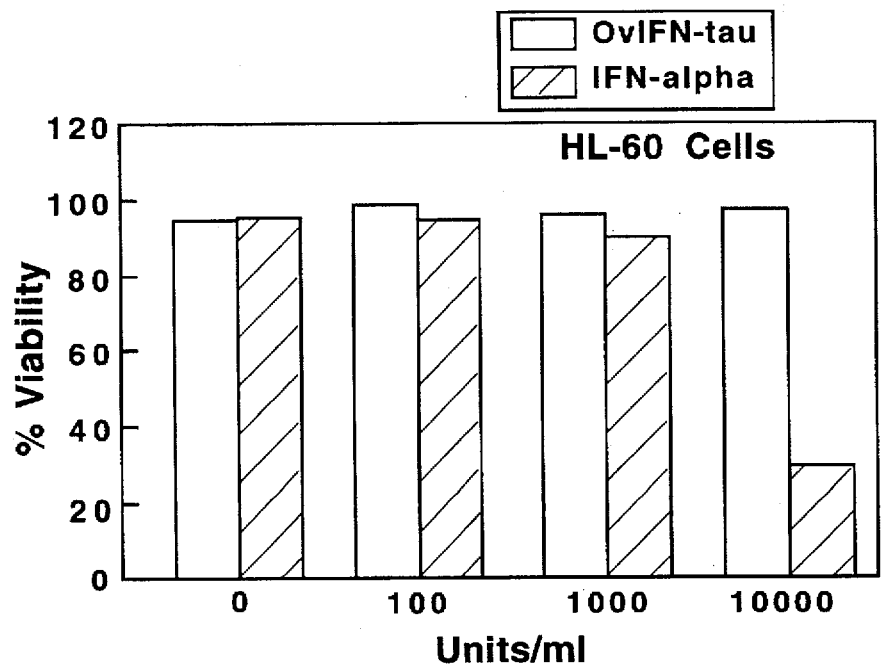
FIG. 5 presents data demonstrating that rHuIFNα is cytotoxic and OvIFNτ is not. In the figure, results of one of three replicate experiments are presented as mean % viability±SD.

A comparison of the antiproliferative effects of IFNτ and IFNα was conducted using HL-60 (human promyelocytic leukemia) cells. Results with the promyelocytic leukemia HL-60 are typical of those obtained comparing IFNτ with human IFNα (Example 15). Concentrations as low as 100 units/ml of both IFNs produced significant (>60%) growth reduction. Increasing amounts of IFNs further decreased tumor cell proliferation (FIG. 4). High doses of HuIFNα, but not OvIFNτ, were cytotoxic (FIG. 5). Cell viability was reduced by approximately 80% by IFNα. By contrast, nearly 100% of the IFNτ-treated cells remained viable when IFNτ was applied at 10,000 units/ml. Thus, while both interferons inhibit proliferation, only IFNτ is without cytotoxicity. This lack of toxicity provides an advantage of IFNτ for use in vivo therapies.

The human cutaneous T cell lymphoma, HUT 78, responded similarly to HL-60 when treated with IFNτ (Example 15, FIG. 9). Both OvIFNτ and rHuIFNα reduce HUT 78 cell growth, but IFNα demonstrated adverse effects on cell viability.

The T cell lymphoma H9 was less sensitive to the antiproliferative effects of IFNα than the tumor cell lines described above. While IFNα was not toxic to the H9 cells, it failed to inhibit cell division significantly at any of the concentrations examined (Example 15, FIG. 10). In contrast, IFNτ was observed to reduce H9 growth by approximately 60%. Thus, only OvIFNτ is an effective growth inhibitor of this T cell lymphoma.

In three additional tumor cell lines (NCI-H460, DLD-1 and SK-MEL-28) IFNτ and IFNα were equally efficacious antitumor agents. In the melanoma, SK-MEL-28, inhibition of proliferation by IFNα was accomplished by a 13% drop in viability, while IFNτ was not cytotoxic. In the majority of tumors examined, IFNτ is equal or preferable to IFNα as an antineoplastic agent against human tumors.

IFNτ exhibits antiproliferative activity against human tumor cells without toxicity and is as potent or more potent than human IFNα. Clinical trials of the IFNα2s have shown them to be effective antitumor agents (Dianzani, F., 1992; Krown, 1987). One advantage of IFNτ as a therapeutic is the elimination of toxic effects seen with high doses IFNαs.

An additional application of the IFNτ is against tumors like Kaposi's sarcoma (associated with HIV infection) where the antineoplastic effects of IFNτ are coupled with IFNτ ability to inhibit retroviral growth.

The in vivo efficacy of interferon-τ treatment was examined in a mouse system (Example 16). B16-F10 is a syngeneic mouse transplantable tumor selected because of its high incidence of pulmonary metastases (Poste, et al., 1981). Interferon treatment was initiated 3 days after the introduction of the tumor cells. The in vivo administration of IFNτ dramatically reduced B16-F10 pulmonary tumors. Thus, IFNτ appears to be an efficacious antineoplastic agent in vivo as well as in vitro.

These results support the usefulness of human IFNτ for use in methods to inhibit or reduced tumor cell growth, including, but are not limited to, the following types of tumor cells: human carcinoma cells, hematopoietic cancer cells, human leukemia cells, human lymphoma cells, human melanoma cells and steroid-sensitive tumor cells (for example, mammary tumor cells).

E. Cytotoxicity of Interferons.

One advantage of IFNτ over other interferons, such as IFNα, is that treatment of a subject with therapeutic doses of INFτ does not appear to be associated with cytotoxicity. In particular, IFN-τ appears to be non-toxic at concentrations at which IFN-β induces toxicity. This is demonstrated by experiments in which L929 cells were treated with various concentrations of either oIFNτ or MuIFN-β (Lee Biomolecular, San Diego, Calif.), ranging from 6000 U/ml to 200,000 U/ml (Example 18E).

oIFNτ, MuIFN-α or medium (control) were added at time zero and the cells were incubated for 72 hours. The results of the experiments are presented in FIG. 21. The percent of live cells (relative to control) is indicated along the y-axis (±standard error). One hundred percent is equal to the viability of L929 cells treated with medium alone. The results indicate that oIFNτ is essentially non-toxic at concentrations up to 100,000 U/ml, and is significantly less toxic than MuIFN-β over the entire therapeutic range of the compounds.

It has been previously demonstrated that in vivo treatment with both of the type I IFNs, IFNβ and IFNα, in humans and animals causes toxicity manifested as a number of side effects including fever, lethargy, tachycardia, weight loss, and leukopenia (Degre, 1974; Fent and Zbinden, 1987). The effect of in vivo treatment with IFNτ, IFNβ and IFNα ($10^5$ U/injection) on total white blood cell (WBC), total lymphocyte counts and weight measurements in NZW mice (Table 13) was examined as described in Example 18F. No significant difference between IFNτ treated and untreated mice was observed for WBC, lymphocyte counts or weight change.

In comparison, IFNβ treated mice exhibited a 31.7% depression in lymphocyte counts 12 hours after injection. Further, depression of lymphocyte counts continued 24 hours after IFNβ injection. IFNα treated mice exhibited a 55.8% lymphocyte depression and significant weight loss 12 hours after injection. Thus, IFNτ appears to lack toxicity in vivo unlike IFNβ and IFNα as evidenced by studies of peripheral blood and weight measurements.

oIFNτ is 172 amino acids long compared to 165 or 166 amino acids for IFNα. The carboxyl-terminal portion of oIFNτ is hydrophilic and thought to be surface accessible. To explore whether this carboxyl "tail" interacts with the binding epitope of oIFNτ to mediate the relative lack of cytotoxicity, a series of deletion mutants were generated.

The carboxyl terminal 2, 6 and 10 amino acids of oIFNτ were removed by cassette mutagenesis of a synthetic oIFNτ gene. The mutant (variant) synthetic genes were cloned into the pHIL-S1 Pichia expression plasmid (Invitrogen, San Diego, Calif.), the plasmid was cut with BglII, and the linearized plasmid was used to transform *Pichia pastoris* (strain GS115; Invitrogen) spheroplasts according to the manufacturer's instructions.

Recombinant variant proteins expressed by transformed His+ Mut− yeast cells were purified and used to determine in vitro antiviral activity and relative cytotoxicity of the variants compared to intact oIFNτ and IFN-α. The cytoxicity of the variants was distributed between the that of oIFNτ and IFN-α. Variants with shorter deletions were more similar in their cytotoxic properties to oIFNτ, while those with longer deletions were more similar to IFN-α.

While not wishing to be bound by any specific molecular mechanisms underlying the properties of IFNτ, the results of the experiments suggest that the C-terminus 10 amino acids of IFNτ may play a role in the decreased cytotoxicity of IFNτ relative to other interferons.

III. Interferon-τ Polypeptide Fragments, Protein Modeling and Protein Modifications.

A. IFNτ Polypeptide Fragments.

The variety of IFNτ activities, its potency and lack of cytotoxicity, as taught by the present specification, suggest the importance of structure/function analysis for this novel interferon. The structural basis for OvIFNτ function has been examined using six overlapping synthetic peptides corresponding to the entire OvIFNτ sequence (FIG. 6). The corresponding polypeptides derived from the ovine IFNτ sequence are presented as SEQ ID NO:5 to SEQ ID NO:10. Three peptides representing amino acids 1-37, 62-92 and 139-172 have been shown to inhibit IFNτ antiviral activity (Example 17). The peptides were effective competitors at concentrations of 300 μM and above.

The synthetic polypeptide representing the C-terminal region of ovIFNτ, OvIFNτ (139-172), and the internal peptide OvIFNτ (62-92), inhibited IFNτ and rBoIFNα$_{II}$ antiviral activity to the same extent, while the N-terminal peptide OvIFNτ (1-37) was more effective in inhibiting OvIFNτ antiviral activity. Dose-response data indicated that IFNτ (62-92) and IFNτ (139-172) inhibited IFNτ antiviral activity to similar extents. The same peptides that blocked IFNτ antiviral activity also blocked the antiviral activity of recombinant bovine IFNα (rBoIFNα); recombinant bovine IFNγ was unaffected by the peptides. These two IFNτ peptides may represent common receptor binding regions for IFNτ and various IFNαs.

Figure 11A:
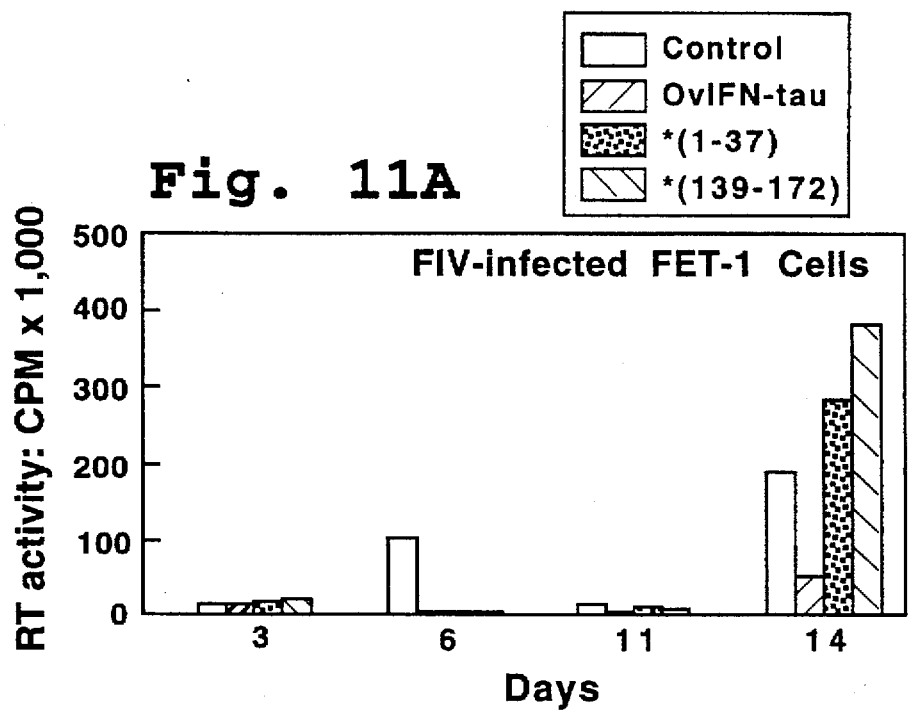
FIG. 11A presents data for the peptide inhibition, relative to FIV (feline immunodeficiency virus) replication, of polypeptides derived from OvIFNτ with whole OvIFNτ.
Figure 11B:
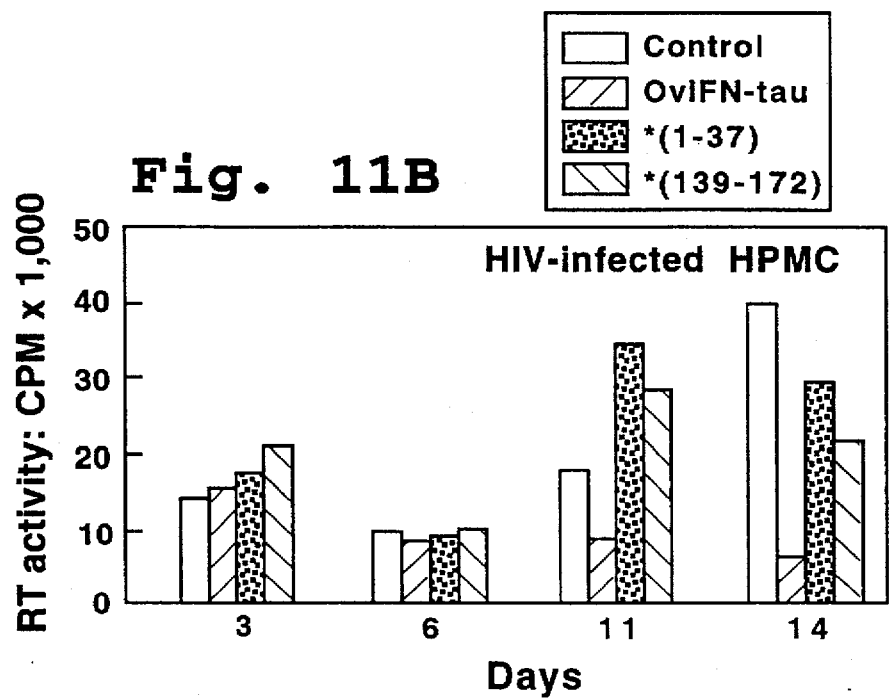
FIG. 11B presents data for the peptide inhibition, relative to HIV (human immunodeficiency virus) replication, of polypeptides derived from OvIFNτ with whole OvIFNτ.

The two synthetic peptides OvIFNτ (1-37) and OvIFNτ (139-172) also blocked OvIFNτ anti-FIV and anti-HIV activity (Example 17; FIGS. 11A and 11B). While both peptides blocked FIV RT activity, only the C-terminal peptide, OvIFNτ (139-172), appeared to be an efficient inhibitor of vesicular stomatitis virus activity on the feline cell line, Fc9.

The above data taken together suggest that the C-terminal regions of type I interferons may bind to common site on the type I interferon receptor, while the N-terminal region may be involved in the elicitation of unique functions. These results suggest that portions of the IFNτ molecule may be used to substitute regions of interferon alpha molecules. For example, the region of an interferon alpha molecule that is responsible for increased cytotoxicity, relative to IFNτ treatment, can be identified by substituting polypeptide regions derived from IFNτ for regions of an interferon alpha molecule. Such substitutions can be carried out by manipulation of synthetic genes (see below) encoding the selected IFNτ and interferon alpha molecules, coupled to the functional assays described herein (such as, antiviral, antiproliferative and cytoxicity assays).

Polyclonal anti-peptide antisera against the IFNτ peptides yielded similar results as the polypeptide inhibition studies, described above. Antibodies directed against the same three regions (OvIFNτ (1-37), IFNτ (62-92) and IFNτ (139-172)) blocked OvIFNτ function, confirming the importance of these three domains in antiviral activity (Example 17). These peptides, although apparently binding to the interferon receptor, did not in and of themselves elicit interferon-like effects in the cells.

The antiproliferative activity of IFNτ (Example 17, Table 11) involved a further region of the molecule, since IFNτ (119-150) was the most effective inhibitor of OvIFNτ-induced reduction of cell proliferation. This results suggests that the region of the molecule primarily responsible for inhibition of cell growth is the IFNτ (119-150) region. This region of the IFNτ molecule may be useful alone or fused to other proteins (such as serum albumin, an antibody or an interferon alpha polypeptide) as an antineoplastic agent. A conjugated protein between an N-terminal peptide derived from human interferon-α and serum albumin was shown to have anticellular proliferation activity (Ruegg, et al., 1990).

Finally, binding of $^{125}$I-OvIFNτ to its receptor on MDBK cells could be blocked by antisera to 4 of the 6 peptides; the 4 polypeptides representing amino acids 1-37, 62-92, 119-150 and 139-172 of OvIFNτ. This reflects the multiple binding domains as well as the functional significance of these regions. Since different regions of IFNτ are involved in elicitation of different functions, modification of selected amino acids could potentially result in IFNτ-like interferons with selective biological activity.

Polypeptide fragments of human IFNτ proteins, having similar properties to the OvIFNτ polypeptides just described, are proposed based on the data presented above for OvIFNτ polypeptide fragments combined with the HuIFNτ sequence information disclosed herein. Such human-sequence derived polypeptides include, but are not limited to, the following: SEQ ID NO:15 to SEQ ID NO:20, and SEQ ID NO:35 to SEQ ID NO:40.

The above data demonstrate the identification of synthetic peptides having four discontinuous sites on the OvIFNτ protein that are involved in receptor interaction and biological activity. In order to elucidate the structural relationship of these regions, modeling of the three dimensional structure of IFNτ was undertaken. A three dimensional model would be useful in interpretation of existing data and the design of future structure/function studies.

B. Molecular Modeling

Combining circular dichroism (CD) data of both the full length recombinant OvIFNτ and IFNβ (a protein of known three dimensional structure (Senda, et al., 1992)), a model of OvIFNτ was constructed. The most striking feature of this model is that IFNτ falls into a class of proteins with a four-helix bundle motif. The CD spectra of IFNτ was taken on an AVIV 60 S spectropolarimeter. Two different methods were employed for secondary structure estimations, the algorithm of Perczel, et al., (1991) and variable selection by W. C. Johnson, Jr. (1992).

Secondary structure estimations of the spectra indicate 70–75% alpha helix (characterized by minima at 222 and 208 nm and maximum at 190 nm). The variable selection algorithm estimates the remainder of the molecule to be 20% beta sheet and 10% turn. The Chang method estimates the remainder to be 30% random coil. Alignment of IFNτ and IFNβ sequences revealed homology between the two molecules, specifically in the regions of known helical structure in IFNβ. Sequence analysis of IFNτ also showed that proposed helical regions possess an apolar periodicity indicative of a four-helix bundle motif.

The final modeling step was to apply the IFNβ x-ray crystallographic coordinates of the IFNβ carbon backbone to the IFNτ sequence. The functionally active domains of IFNτ, identified above, were localized to one side of the molecule and found to be in close spatial proximity. This is consistent with multiple binding sites on IFNτ interacting simultaneously with the type I IFN receptor.

The three dimensional modeling data coupled with the function data described above, provides the information necessary to introduce sequence variations into specific regions of IFNτ to enhance selected functions (e.g., antiviral or anticellular proliferation) or to substitute a region(s) of selected function into other interferon molecules (e.g., antiviral, antineoplastic, or reduced cytotoxicity).

C. Recombinant and Synthetic Manipulations

The construction of a synthetic gene for OvIFNτ is described in Example 3. Briefly, an amino acid sequence of ovIFNτ was back-translated from an ovIFNτ cDNA (Imakawa, et al., 1987) using optimal codon usage for *E. coli*. The sequence was edited to include 20 unique, restriction sites spaced throughout the length of the construct. This 540 base pair synthetic gene sequence was divided into 11 oligonucleotide fragments. individual fragments were synthesized and cloned, either single or double stranded, into either pTZ 19R, pTZ 18R or pBluescript, amplified and fused. The synthetic OvIFNτ construct was then cloned into a modified pIN-III-ompA expression vector for expression in bacteria and also cloned into a yeast expression plasmid. A similarly constructed human IFNτ synthetic gene (SEQ ID NO:3) has been designed, constructed and expressed in yeast cells.

Expression of the OvIFNτ synthetic gene in yeast (Example 4) allowed over production of recombinant IFNτ in *S. cerevisiae*: large quantities (5–20 mg/l) of recombinant IFNτ can be purified from soluble yeast extract using sequential ion exchange and molecular sieve chromatography. Recombinant IFNτ purified in this fashion exhibited potent antiviral activity (2 to 3×10$^8$ units/mg) similar to native OvIFNτ.

The synthetic gene construct facilitates introduction of mutations for possible enhancement of antitumor (anticellular proliferative) and antiviral activities. Further, the disparate regions of the molecule responsible for different functions can be modified independently to generate a molecule with a desired function. For example, two deletion mutants, OvIFNτ (1-162) and OvIFNτ (1-166), have been constructed to examine the role of carboxy terminal sequences in IFNτ molecules.

Additional mutant IFNτ molecules have been constructed to identify residues critical for antiproliferative activity. For example, one particular residue, TYR 123 has been implicated in the anticellular proliferative activity of IFNα (McInnes, et al., 1989). The equivalent of TYR 123 in IFNτ is contained within peptide OvIFNτ (119-150): this polypeptide inhibits OvIFNτ and human IFNα antiproliferative activity. Mutations converting TYR 123 to conservative (TRP) and nonconservative (ASP) substitutions have been generated, as well as mutant sequences having deletion of this residue. The codon for TYR 123 is located within an SspI site; elimination of this site has been used for screening. The antiproliferative activity of these mutant IFNτ is evaluated as described herein.

Synthetic peptides can be generated which correspond to the IFNτ polypeptides of the present invention. Synthetic peptides can be commercially synthesized or prepared using standard methods and apparatus in the art (Applied Biosystems, Foster City Calif.).

Alternatively, oligonucleotide sequences encoding peptides can be either synthesized directly by standard methods of oligonucleotide synthesis, or, in the case of large coding sequences, synthesized by a series of cloning steps involving a tandem array of multiple oligonucleotide fragments corresponding to the coding sequence (Crea; Yoshio et al.; Eaton et al.). Oligonucleotide coding sequences can be expressed by standard recombinant procedures (Maniatis et al.; Ausubel et al.).

The biological activities of the interferon-τ polypeptides described above can be exploited using either the interferon-τ polypeptides alone or conjugated with other proteins (see below).

IV. Production of Fusion Proteins.

In another aspect, the present invention includes interferon-τ or interferon-τ-derived polypeptides covalently attached to a second polypeptide to form a fused, or hybrid, protein. The interferon-τ sequences making up such fused proteins can be recombinantly produced interferon-τ or a bioactive portion thereof, as described above.

For example, where interferon-τ is used to inhibit viral expression, polypeptides derived from IFNτ demonstrating antiviral activity may be advantageously fused with a soluble peptide, such as, serum albumin, an antibody (e.g., specific against an virus-specific cell surface antigen), or an interferon alpha polypeptide. In one embodiment, the IFNτ polypeptides provide a method of reducing the toxicity of other interferon molecules (e.g., IFNβ or IFNα) by replacing toxicity-associated regions of such interferons with, for example, corresponding interferon-τ regions having lower toxicity. In another embodiment, fusion proteins are generated containing interferon-τ regions that have anticellular proliferation properties. Such regions may be obtained from, for example, the human interferon-τ sequences disclosed herein.

The fused proteins of the present invention may be formed by chemical conjugation or by recombinant techniques. In the former method, the interferon-τ and second selected polypeptide are modified by conventional coupling agents for covalent attachment. In one exemplary method for coupling soluble serum albumin to an interferon-τ polypeptide, serum albumin is derivatized with N-succinimidyl-S-acetyl thioacetate (Duncan), yielding thiolated serum albumin. The activated serum albumin polypeptide is then reacted with interferon-τ derivatized with N-succinimidyl 3-(2-pyridyldithio)propionate (Cumber), to produce the fused protein joined through a disulfide linkage.

As an alternative method, recombinant interferon-τ may be prepared with a cysteine residue to allow disulfide coupling of the interferon-τ to an activated ligand, thus simplifying the coupling reaction. An interferon-τ expression vector, used for production of recombinant interferon-τ, can be modified for insertion of an internal or a terminal cysteine codon according to standard methods of site-directed mutagenesis (Ausubel, et al.).

In one method, a fused protein is prepared recombinantly using an expression vector in which the coding sequence of a second selected polypeptide is joined to the interferon-τ coding sequence. For example, human serum albumin coding sequences can be fused in-frame to the coding sequence of an interferon-τ polypeptide, such as, SEQ ID NO:9, SEQ ID NO:19 or SEQ ID NO:39. The fused protein is then expressed using a suitable host cell. The fusion protein may be purified by molecular-sieve and ion-exchange chromatography methods, with additional purification by polyacrylamide gel electrophoretic separation and/or HPLC chromatography, if necessary.

It will be appreciated from the above how interferon-τ-containing fusion proteins may be prepared. One variation on the above fusion is to exchange positions of the interferon-τ and selected second protein molecules in the fusion protein (e.g., carboxy terminal versus amino terminal fusions). Further, internal portions of a native interferon-τ polypeptide (for example, amino acid regions of between 15 and 172 amino acids) can be assembled into polypeptides where two or more such interferon-τ portions are contiguous that are normally discontinuous in the native protein.

In addition to the above-described fusion proteins, the present invention also contemplates polypeptide compositions having (a) a human interferon-τ polypeptide, where said polypeptide is (i) derived from an interferon-τ amino acid coding sequence, and (ii) between 15 and 172 amino acids long, and (b) a second soluble polypeptide. Interferon-α and interferon-β are examples of such second soluble polypeptides. IFNτ polypeptides associated with reduced toxicity may be co-administered with more toxic interferons to reduce the toxicity of the more toxic interferons when used in pharmaceutical formulations or in therapeutic applications. Such IFNτ polypeptides would, for example, reduce the toxicity of IFNα but not interfere with IFNα antiviral properties.

V. Antibodies Reactive with Interferon-τ.

Fusion proteins containing the polypeptide antigens of the present invention fused with the glutathione-S-transferase (Sj26) protein can be expressed using the pGEX-GLI vector system in *E. coli* JM101 cells. The fused Sj26 protein can be isolated readily by gtutathione substrate affinity chromatography (Smith). Expression and partial purification of IFNτ proteins is described in (Example 20), and is applicable to any of the other soluble, induced polypeptides coded by sequences described by the present invention.

Insoluble GST (sj26) fusion proteins can be purified by preparative gel electrophoresis.

Alternatively, IFNτ-β-galactosidase fusion proteins can be isolated as described in Example 19.

Also included in the invention is an expression vector, such as the lambda gt11 pGEX vectors described above, containing IFNτ coding sequences and expression control elements which allow expression of the coding regions in a suitable host. The control elements generally include a promoter, translation initiation codon, and translation and transcription termination sequences, and an insertion site for introducing the insert into the vector.

The DNA encoding the desired polypeptide can be cloned into any number of vectors (discussed above) to generate expression of the polypeptide in the appropriate host system. These recombinant polypeptides can be expressed as fusion proteins or as native proteins. A number of features can be engineered into the expression vectors, such as leader sequences which promote the secretion of the expressed sequences into culture medium. Recombinantly produced IFNτ, and polypeptides derived therefrom, are typically isolated from lysed cells or culture media. Purification can be carried out by methods known in the art including salt fractionation, ion exchange chromatography, and affinity chromatography. Immunoaffinity chromatography can be employed using antibodies generated against selected IFNτ antigens.

In another aspect, the invention includes specific antibodies directed against the polypeptides of the present invention. Typically, to prepare antibodies, a host animal, such as a rabbit, is immunized with the purified antigen or fused protein antigen. Hybrid, or fused, proteins may be generated using a variety of coding sequences derived from other proteins, such as β-galactosidase or glutathione-S-transferase. The host serum or plasma is collected following an appropriate time interval, and this serum is tested for antibodies specific against the antigen. Example 20 describes the production of rabbit serum antibodies which are specific against the IFNτ antigens in a Sj26/IFNτ hybrid protein. These techniques can be applied to the all of the IFNτ molecules and polypeptides derived therefrom.

The gamma globulin fraction or the IgG antibodies of immunized animals can be obtained, for example, by use of saturated ammonium sulfate or DEAE Sephadex, or other techniques known to those skilled in the art for producing polyclonal antibodies.

Alternatively, purified protein or fused protein may be used for producing monoclonal antibodies. Here the spleen or lymphocytes from a animal immunized with the selected polypeptide antigen are removed and immortalized or used to prepare hybridomas by methods known to those skilled in the art (Harlow, et al.). Lymphocytes can be isolated from a peripheral blood sample. Epstein-Barr virus (EBV) can be used to immortalize human lymphocytes or a fusion partner can be used to produce hybridomas.

Antibodies secreted by the immortalized cells are screened to determine the clones that secrete antibodies of the desired specificity, for example, by using the ELISA or Western blot method (Ausubel et al.). Experiments performed in support of the present invention have yielded four hybridomas producing monoclonal antibodies specific for ovine IFNτ have been isolated.

Antigenic regions of polypeptides are generally relatively small, typically 7 to 10 amino acids in length. Smaller fragments have been identified as antigenic regions. Interferon-τ polypeptide antigens are identified as described above. The resulting DNA coding regions can be expressed recombinantly either as fusion proteins or isolated polypeptides.

In addition, some amino acid sequences can be conveniently chemically synthesized (Applied Biosystems, Foster City Calif.). Antigens obtained by any of these methods may be directly used for the generation of antibodies or they may be coupled to appropriate carrier molecules. Many such carriers are known in the art and are commercially available (e.g., Pierce, Rockford Ill.).

Antibodies reactive with IFNτ are useful, for example, in the analysis of structure/function relationships.

VI. Utility

A. Reproductive.

Although IFNτ bears some similarity to the IFNα family based on structure and its potent antiviral properties, the IFNαs do not possess the reproductive properties associated with IFNτ. For example, recombinant human IFNα had no effect on interestrous interval compared to IFNτ, even when administered at twice the dose (Davis, et al., 1992).

Therefore, although IFNτ has some structural similarities to other interferons, it has very distinctive properties of its own: for example, the capability of significantly influencing the biochemical events of the estrous cycle.

The human IFNτ of the present invention can be used in methods of enhancing fertility and prolonging the life span of the corpus luteum in female mammals as generally described in Hansen, et al., herein incorporated by reference. Further, the human interferon-τ of the present invention could be used to regulate growth and development of uterine and/or fetal-placental tissues. The human IFNτ is particularly useful for treatment of humans, since potential antigenic responses are less likely using such a same-species protein.

B. Antiviral Properties.

The antiviral activity of IFNτ has broad therapeutic applications without the toxic effects that are usually associated with IFNαs. Although the presence of IFNτ in culture medium inhibited reverse transcriptase activity of the feline immunodeficiency virus (Example 11), this is not due to a direct effect of IFNτ on the reverse transcriptase. Rather, IFNτ appears to induce the host cell to produce a factor(s) which is inhibitory to the reverse transcriptase of the virus.

IFNτ was found to exert its antiviral activity without adverse effects on the cells: no evidence of cytotoxic effects attributable to the administration of IFNτ was observed. It is the lack of cytotoxicity of IFNτ which makes it extremely valuable as an in vivo therapeutic agent. This lack of cytotoxicity sets IFNτ apart from most other known antiviral agents and all other known interferons.

Formulations comprising the IFNτ compounds of the present invention can be used to inhibit viral replication.

The human IFNτ of the present invention can be employed in methods for affecting the immune relationship between fetus and mother, for example, in preventing transmission of maternal viruses (e.g., HIV) to the developing fetus. The human interferon-τ is particularly useful for treatment of humans, since potential antigenic responses are less likely using a homologous protein.

C. Anticellular Proliferation Properties.

IFNτ exhibits potent anticellular proliferation activity. IFNτ can also be used to inhibit cellular growth without the negative side effects associated with other interferons which are currently known. Formulations comprising the IFNτ compounds of the subject invention can be used to inhibit, prevent, or slow tumor growth.

The development of certain tumors is mediated by estrogen. Experiments performed in support of the present invention indicate that IFNτ can suppress estrogen receptor numbers. Therefore, IFNτ can be used in the treatment or prevention of estrogen-dependent tumors.

D. Interfering with the Binding of Interferons to Receptors.

IFNτ appears to interact with the Type I IFN receptor via several epitopes on the molecule, and these regions either separately or in combination may affect distinct functions of IFNτ differently.

The polypeptides of the present invention are useful for the selective inhibition of binding of interferons to the interferon receptor. Specifically, as described herein, certain of the disclosed peptides selectively inhibit the antiviral activity of IFNτ while others inhibit the antiproliferative activity. Combinations of these peptides could be used to inhibit both activities. Advantageously, despite binding to the interferon receptor and blocking IFNτ activity, these peptides do not, themselves, elicit the antiviral or antiproliferative activity.

Therefore, such polypeptides can be used as immunoregulatory molecules when it is desired to prevent immune responses triggered by interferon molecules. These peptides could be used as immunosuppressants to prevent, for example, interferon-mediated immune responses to tissue transplants. Other types of interferon mediated responses may also be blocked, such as the cytotoxic effects of alpha interferon.

E. Pharmaceutical Compositions.

IFNτ proteins can be formulated according to known methods for preparing pharmaceutically useful compositions. Formulations comprising interferons or interferon-like compounds have been previously described (for example, Martin, 1976). In general, the compositions of the subject invention will be formulated such that an effective amount of the IFNτ is combined with a suitable carrier in order to facilitate effective administration of the composition.

The compositions used in these therapies may also be in a variety of forms. These include, for example, solid, semi-solid, and liquid dosage forms, such as tablets, pills, powders, liquid solutions or suspensions, liposomes, suppositories, injectable, and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

IFNτ, or related polypeptides, may be administered to a patient in any pharmaceutically acceptable dosage form, including oral intake, inhalation, intranasal spray, intraperitoneal, intravenous, intramuscular, intralesional, or subcutaneous injection. Specifically, compositions and methods used for other interferon compounds can be used for the delivery of these compounds.

One primary advantage of the compounds of the subject invention, however, is the extremely low cytotoxicity of the IFNτ proteins. Because of this low cytotoxicity, it is possible to administer the IFNτ in concentrations which are greater than those which can generally be utilized for other interferon (e.g., IFNα) compounds. Thus, IFNτ can be administered at rates from about $5 \times 10^4$ to $20 \times 10^6$ units/day to about $500 \times 10^6$ units/day or more. In a preferred embodiment, the dosage is about $20 \times 10^6$ units/day. High doses are preferred for systemic administration. It should, of course, be understood that the compositions and methods of this invention may be used in combination with other therapies.

Once improvement of a patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

The compositions of the subject invention can be administered through standard procedures to treat a variety of cancers and viral diseases including those for which other interferons have previously shown activity. See, for example, Finter, et al. (1991); Dianzani, et al. (1992); Francis, et al. (1992) and U.S. Pat. Nos. 4,885,166 and 4,975,276. However, as discussed above, the compositions of the subject invention have unique features and advantages, including their ability to treat these conditions without toxicity.

F. Treatment of Skin Disorders.

Disorders of the skin can be treated intralesionally using IFNτ, wherein formulation and dose will depend on the method of administration and on the size and severity of the lesion to be treated. Preferred methods include intradermal and subcutaneous injection. Multiple injections into large lesions may be possible, and several lesions on the skin of a single patient may be treated at one time. The schedule for administration can be determined by a person skilled in the art. Formulations designed for sustained release can reduce the frequency of administration.

G. Systemic Treatment.

Systemic treatment is essentially equivalent for all applications. Multiple intravenous, subcutaneous and/or intramuscular doses are possible, and in the case of implantable methods for treatment, formulations designed for sustained release are particularly useful. Patients may also be treated using implantable subcutaneous portals, reservoirs, or pumps.

H. Regional Treatment.

Regional treatment with the IFNτ polypeptides of the present invention is useful for treatment of cancers in specific organs. Treatment can be accomplished by intraarterial infusion. A catheter can be surgically or angiographically implanted to direct treatment to the affected organ. A subcutaneous portal, connected to the catheter, can be used for chronic treatment, or an implantable, refillable pump may also be employed.

The following examples illustrate, but in no way are intended to limit the present invention.

Materials and Methods

Restriction endonucleases, T4 DNA ligase, T4 polynucleotide kinase, Taq DNA polymerase, and calf intestinal phosphatase were purchased from New England Biolabs (Beverly, Mass.) or Promega Biotech (Madison, Wis.): these reagents were used according to the manufacturer's instruction. For sequencing reactions, a "SEQUENASE DNA II" sequencing kit was used (United States Biochemical Corporation, Cleveland Ohio). Immunoblotting and other reagents were from Sigma Chemical Co. (St. Louis, Mo.) or Fisher Scientific (Needham, Mass.). Nitrocellulose filters are obtained from Schleicher and Schuell (Keene, N.H.).

Synthetic oligonucleotide linkers and primers are prepared using commercially available automated oligonucleotide synthesizers (e.g., an ABI model 380B-02 DNA synthesizer (Applied Biosystems, Foster City, Calif.)). Alternatively, custom designed synthetic oligonucleotides may be purchased, for example, from Synthetic Genetics (San Diego, Calif.). cDNA synthesis kit and random priming labeling kits are obtained from Boehringer-Mannheim Biochemical (BMB, Indianapolis, Ind.).

Oligonucleotide sequences encoding polypeptides can be either synthesized directly by standard methods of oligonucleotide synthesis, or, in the case of large coding sequences, synthesized by a series of cloning steps involving a tandem array of multiple oligonucleotide fragments corresponding to the coding sequence (Crea; Yoshio et al.; Eaton et al.). Oligonucleotide coding sequences can be expressed by standard recombinant procedures (Maniatis et al.; Ausubel et al.).

Alternatively, peptides can be synthesized directly by standard in vitro techniques (Applied Biosystems, Foster City Calif.).

Common manipulations involved in polyclonal and monoclonal antibody work, including antibody purification from sera, are performed by standard procedures (Harlow et al.). Pierce (Rockford, Ill.) is a source of many antibody reagents.

Recombinant human IFNα (rHuIFNα) and rBoIFNγ was obtained from Genentech Inc. (South San Francisco, Calif.). The reference preparation of recombinant human IFNα (rHuIFNα) was obtained from the National Institutes of Health: rHuIFNα is commercially available from Lee Biomolecular (San Diego, Calif.).

All tissue culture media, sera and IFNs used in this study were negative for endotoxin, as determined by assay with Limulus amebocyte lysate (Associates of Cape Cod, Woods Hole, Mass.) at a sensitivity level of 0.07 ng/ml.

General ELISA Protocol for Detection of Antibodies.

Polystyrene 96 well plates Immulon II (PGC) were coated with 5 µg/mL (100 µL per well) antigen in 0.1M carb/bicarbonate buffer, pH 9.5. Plates were sealed with parafilm and stored at 4° C. overnight.

Plates were aspirated and blocked with 300 uL 10% NGS and incubated at 37° C. for 1 hr.

Plates were washed 5 times with PBS 0.5% "TWEEN-20".

Antisera were diluted in 0.1M PBS, pH 7.2. The desired dilution(s) of antisera (0.1 mL) were added to each well and the plate incubated 1 hours at 37° C. The plates was then washed 5 times with PBS 0.5% "TWEEN-20".

Horseradish peroxidase (HRP) conjugated goat anti-human antiserum (Cappel) was diluted 1/5,000 in PBS. 0.1 mL of this solution was added to each well. The plate was incubated 30 min at 37° C., then washed 5 times with PBS.

Sigma ABTS (substrate) was prepared just prior to addition to the plate.

The reagent consists of 50 mL 0.05M citric acid, pH 4.2, 0.078 mL 30% hydrogen peroxide solution and 15 mg ABTS. 0.1 mL of the substrate was added to each well, then incubated for 30 min at room temperature. The reaction was stopped with the addition of 0.050 mL 5% SDS (w/v). The relative absorbance is determined at 410 nm.

EXAMPLE 1

Reproductive Functions of IFNτ

The effect of interferon-τ on the lifespan of the corpus lutem was examined.

IFNτ was infused into uterine lumen of ewes at the concentrations given in Table 1. Recombinant human IFNα (rHuIFNα) was infused at similar concentrations. In addition, control animals, which received control proteins, were also used. The life span of the corpus luteum was assessed by examination of interestrous intervals, maintenance of progesterone secretion, and inhibition of prostaglandin secretion (Davis, et al., 1992).

TABLE 1

Effect of Interferons on Reproductive Physiology

| Interferon | Treatment | Interestrous Interval (days) (Means) |
|---|---|---|
| Control | — | 17.3 |
| rHuIFNα | 100 µg/day | 16.0 |
|  | 200 µg/day | 16.0 |
|  | 2000 µg/day | 19.0 |
| OvIFNτ | 100 µg/day | 27.2 |

Comparison of the interestrous intervals for the control animals and for animals receiving OvIFNτ demonstrate a considerable lengthening of the interval, when IFNτ is administered at 100 µg/day. On the other hand, comparison of the interestrous interval for the control animal and for animals receiving recombinant human IFNα, demonstrated that rHuIFNα had no meaningful effect.

These results demonstrate that interferon-τ has the capability of significantly influencing the biochemical events of the reproductive cycle.

EXAMPLE 2

Antiviral Properties of Interferon-τ at Various Stages of the Reproductive Cycle Conceptus cultures were established using conceptus obtained from sheep at days 12 through 16 of the estrous cycle. Antiviral activity of supernatant from each conceptus culture was assessed using a cytopathic effect assay (Familetti, et al., 1981). Briefly, dilutions of IFNτ or other IFNs were incubated with Madin-Darby bovine kidney (MDBK) cells for 16–18 hours at 37° C. Following incubation, inhibition of viral replication was determined in a cytopathic effect assay using vesicular stomatitis virus (VSV) as the challenge virus.

One antiviral unit caused a 50% reduction in destruction of the monolayer, relative to untreated MDBK cells infected with VSV (control plates). Specific activities were further evaluated using normal ovine fibroblasts (Shnf) in a plaque inhibition assay (Langford, et al., 1981). A minimum of three samples were examined at each time point, and each sample was assayed in triplicate. The results presented in Table 2 are expressed as mean units/ml.

TABLE 2

IFNτ Antiviral Activity of Conceptus Cultures and Allantoic and Amniotic Fluids

|  | Day | Samples | Units/ml |
|---|---|---|---|
| Conceptus Cultures | 10 | 9 | <3 |
|  | 12 | 5 | 34 |
|  | 13 | 6 | $4.5 \times 10^3$ |
|  | 14 | 3 | $7.7 \times 10^3$ |
|  | 16 | 12 | $2.0 \times 10^6$ |
| Allantoic Fluid | 60 | 3 | $1.4 \times 10^3$ |
|  | 100 | 4 | 11 |
|  | 140 | 3 | <3 |
| Amniotic Fluid | 60 | 3 | 22 |
|  | 100 | 4 | <3 |

Culture supernatants had increasing antiviral activity associated with advancing development of the conceptus (Table 2).

EXAMPLE 3

Expression of IFNτ in Bacteria

The amino acid coding sequence for OvIFNτ (Imakawa, et al., 1987) was used to generate a corresponding DNA coding sequence with codon usage optimized for expression in *E. coli*. Linker sequences were added to the 5' and 3' ends to facilitate cloning in bacterial expression vectors. The nucleotide sequence was designed to include 19 unique restriction enzyme sites spaced evenly throughout the coding sequence (FIGS. 1A and 1B).

The nucleotide sequence was divided into eleven oligonucleotide fragments ranging in sizes of 33 to 75 bases. Each of the eleven oligonucleotides were synthesized on a 380-B 2-column DNA synthesizer (Applied Biosystems) and cloned single- or double-stranded into one of the following vectors: "PBLUESCRIPT+ (KS)" (Stratagene, LaJolla, Calif.), pTZ18R (Pharmacia, Piscataway, N.J.), or pTZ19R (Pharmacia, Piscataway, N.J.) cloning vectors.

The vectors were transformed into *E. coli* K. strain "XL1-BLUE" (recA1 endA1 gyrA96 thi hsdR17 ($r_K^-$, $m_K^+$) supE44 relA1 λ—(lac), {F', proAB, lac$^q$ZΔM15, Tn10 (tet$^R$}) which is commercially available from Stratagene (La Jolla, Calif.). Transformed cells were grown in L broth supplemented with ampicillin (50 µg/ml). Oligonucleotide cloning and fusion was performed using standard recombinant DNA techniques.

Cloning vectors were cut with the appropriate restriction enzymes to insert the synthetic oligonucleotides. The vectors were treated with calf intestine alkaline phosphatase (CIP) to remove terminal phosphate groups. Oligonucleotides were phosphorylated and cloned, as either single- or double-stranded molecules, into the appropriate vector using T4 DNA ligase. When single-strands were introduced into cloning vectors, the second strand was completed by the bacterial host following transfection.

For double-stranded cloning, oligonucleotides were first annealed with their synthetic complementary strand then ligated into the cloning vector. *E. coli* K12 strains SB221 or NM522 were then transformed with the ligation. *E. coli* strain GM119 was used for cloning when the methylation-sensitive StuI and ClaI restriction sites were involved. Restriction analyses were performed on isolated DNA at each stage of the cloning procedure.

Cloned oligonucleotides were fused into a single polynucleotide using the restriction digestions and ligations outlined in FIG. 2. Oligonucleotide-containing-DNA fragments were typically isolated after electrophoretic size fractionation on low-melting point agarose gels (Maniatis, et al.; Sambrook, et al.; Ausubel, et al.). The resulting IFNτ polynucleotide coding sequence spans position 16 through 531: a coding sequence of 172 amino acids.

The nucleotide sequence of the final polynucleotide was confirmed by DNA sequencing using the dideoxy chain termination method.

The full length StuI/SstI fragment (540 bp; FIG. 2) was cloned into a modified pIN III omp-A expression vector and transformed into a competent SB221 strain of *E. coli*. For expression of the IFNτ protein, cells carrying the expression vector were grown in L-broth containing ampicillin to an OD (550 nm) of 0.1–1, induced with IPTG for 3 hours and harvested by centrifugation. Soluble recombinant IFNτ was liberated from the cells by sonication or osmotic fractionation.

EXAMPLE 4

Expression of IFNτ in Yeast

The synthetic IFNτ gene, synthesized in Example 3, was flanked at the 5' end by an StuI restriction site and at the 3' end by a SacI restriction site.

A. Isolation of the Synthetic IFNτ Gene.

Two oligonucleotide primers (SEQ ID NO:13 and SEQ ID NO:14) were used to attach linkers to the synthetic INFτ gene using polymerase chain reaction. The linker at the 5' end allowed the placement of the synthetic IFNτ gene in correct reading with the ubiquitin coding sequence present in the yeast cloning vector pBS24Ub (Chiron Corp., Emeryville, Calif.). The linker also constructed a ubiquitin-IFNτ junction region that allowed in vivo cleavage of the ubiquitin sequences from the IFNτ sequences. The 5' oligonucleotide also encoded a SacII restriction endonuclease cleavage site. The 3' oligonucleotide contained a StuI cleavage site.

The vector carrying the synthetic IFNτ gene (Example 3) was isolated from *E. coli* strain "XLI-BLUE" by the alkaline lysis method. Isolated vector was diluted 500-fold in 10 mM Tris, pH 8.0/1 mM EDTA/10 mM NaCl. The PCR reaction was performed in a 100 µl volume using Taq DNA polymerase and primers SEQ ID NO:13/SEQ ID NO:14. The amplified fragments were digested with StuI and SacII. These digested fragments were ligated into the SacII and SmaI sites of "pBLUESCRIPT+(KS)."

The resulting plasmid was named pBSY-IFNτ. The DNA sequence was verified using double stranded DNA as the template.

B. Construction of the Expression Plasmid.

Plasmid pBSY-IFNτ was digested with SacII and EcoRV and the fragment containing the synthetic IFNτ gene was isolated. The yeast expression vector pBS24Ub (Sabin, et al.; Ecker, et al.) was digested with SalI. Blunt ends were generated using T4 DNA polymerase. The vector DNA was extracted with phenol and ethanol precipitated (Sambrook, et al., 1989). The recovered linearized plasmid was digested with SacII, purified by agarose gel electrophoresis, and ligated to the SacII-EcoRV fragment isolated from pBSY-IFNτ. The resulting recombinant plasmid was designated pBS24Ub-IFNτ.

The recombinant plasmid pBS24Ub-IFNτ was transformed into *E. coli*. Recombinant clones containing the IFNτ insert were isolated and identified by restriction enzyme analysis. Plasmid DNA from clones containing IFNτ coding sequences was used for transformation of *S. cerevisiae* (Rothstein, 1986). Transformation mixtures were plated on uracil omission medium and incubated for 3–5 days at 30° C. Colonies were then streaked and maintained on uracil and leucine omission medium (Rothstein, 1986).

C. Expression Experiments.

For small-scale expression, a single colony of *S. cerevisiae* AB116 containing pBS24Ub-IFNτ was picked from a leucine and uracil omission plate and grown at 30° C. in YEP medium (1% yeast extract, 2% peptone) containing 1% glucose for inducing conditions or 8% glucose for noninducing conditions. Cell lysates were recovered and subjected to SDS-PAGE in 15% acrylamide, 0.4% bisacrylamide (Sambrook, et al., 1989). The fractionated proteins were visualized by Coomassie blue staining.

Recombinant IFNτ was visualized specifically by immunoblotting with monoclonal antibody or polyclonal antiserum against ovine IFNτ upon electrotransfer of the fractionated cell extract to "NYTRAN" paper (Rothstein, 1986).

For large-scale expression, pBS24-IFNτ was grown for 24 hours at 30° C. in 5×uracil and leucine omission medium containing 8% glucose. This culture was then diluted 20-fold in YEP medium containing 1% glucose and further incubated for another 24–36 hours.

Cells were harvested by centrifugation, washed in 50 mM Tris, pH 7.6./1 mM EDTA and resuspended in wash buffer containing 1 mM PMSF. The cells were lysed using a Bead-beater apparatus (Biospec Products, Bartlesville, Okla.). The lysate was spun at 43,000×g for 20 minutes. The supernatant fraction was recovered and subjected to the purification protocol described below.

D. Purification of roIFNτ from Yeast Cell Lysate.

The supernatant was loaded on a 1×10 cm DEAE column and washed with 10 mM Tris, pH 8.0. Retained proteins were eluted with a 300 ml, 0 to 0.5M NaCl gradient in 10 mM Tris, pH 8.0. Three-milliliter fractions were collected. Ten-microliter samples of fractions 17-26 containing the recombinant (roIFNτ) were electrophoretically separated on 15% SDS-polyacrylamide gels. The gels were stained with Coomassie blue.

Fractions 18, 19, and 20 contained largest amount of roIFNτ. These fractions were loaded individually on a 1.5×90 cm Sephadex S-200 column and proteins were resolved in two peaks. Aliquots of each protein peak (25 µl) were electrophoretically separated on 15% SDS-polyacrylamide gels and the proteins visualized with Coomassie staining.

Purified roIFNτ-containing fractions were combined and the amount of roIFNτ quantified by radioimmunoassay (Vallet, et al., 1988). Total protein concentration was determined by using the Lowry protein assay (Lowry, et al., 1951).

Microsequencing of purified roIFNτ demonstrated identity with native IFNτ through the first 15 amino acids, confirming that the ubiquitin/roIFNτ fusion protein was correctly processed in vivo.

Purified roIFNτ exhibited 2 to $3\times10^8$ units of antiviral activity per milligram of protein (n=3 replicate plates) which is similar to the antiviral activity of IFNτ purified from conceptus-conditioned culture medium ($2\times10^8$ U/mg).

EXAMPLE 5

Southern Blot Analysis of Human High Molecular Weight DNA

Human venous blood samples from healthy donors were collected in heparinized tubes and peripheral blood lymphocytes were isolated by density-gradient centrifugation using a Ficoll-Isopaque gradient (1.077 g/ml) (Sigma Chemical Co.). High molecular weight (HMW) DNA was isolated from these cells (Sambrook, et al., 1989).

Two 10 µg samples of HMW DNA were digested with the restriction endonucleases HindIII or PstI (Promega) for 2 hours at 37° C., and the DNA fragments electrophoretically separated in a 0.8% agarose gel (Bio-Rad, Richmond, Calif.) at 75 volts for 8 hours. The DNA fragments were transferred onto a nylon membrane (IBI-International Biotechnologies, Inc., New Haven, Conn.). The membrane was baked at 80° C. for 2 hours and incubated at 42° C. for 4 hours in the following prehybridization solution: 5×SSC (1×SSC is 0.15M NaCl and 0.15M sodium citrate), 50% vol/vol formamide, 0.6% (wt/vol) SDS, 0.5% (wt/vol) nonfat dry milk, 20 mM Tris-HCl (pH 7.5), 4 mM EDTA, and 0.5 mg/ml single stranded herring sperm DNA (Promega).

The filter was then incubated in a hybridization solution (5×SSC, 20% vol/vol formamide, 0.6% (wt/vol) SDS, 0.5% (wt/vol) nonfat dry milk, 20 mM Tris-HCl (pH 7.5), 4 mM EDTA, and $2\times10^8$ cpm/ml $^{32}$P-labelled OvIFNτ cDNA (Imakawa, et al., 1987)) for 18 hours at 42° C. The filter was washed at 42° C. for 15 minutes with 2×SSC and 0.1% (wt/vol) SDS and exposed to X-ray film (XAR, Eastman Kodak, Rochester, N.Y.) at −80° C. for 48 hours in the presence of an intensifying screen.

Autoradiography detected a hybridization signal at approximately 3.4 kb in DNA digested with PstI and a slightly smaller (≈3.0 kb) fragment in the HindIII digested DNA. These results indicate the presence of human DNA sequences complementary to the OvIFNτ cDNA probe.

EXAMPLE 6

Isolation of Partial Sequence of Human IFNτ cDNA by PCR

Two synthetic oligonucleotides (each 25-mer), corresponding to the nucleotides in the DNA sequence from 231 to 255 (contained in SEQ ID NO:13) and 566 to 590 (contained in SEQ ID NO:14) of OvIFNτ cDNA (numbering relative to the cap site, Imakawa, et al., 1987) were synthesized. These primers contained, respectively, cleavage sites for the restriction endonucleases PstI and EcoRI. SEQ ID NO:13 was modified to contain the EcoRI site, which begins at position 569.

DNA was isolated from approximately $1\times10^5$ plaque forming units (pfu) of the following two cDNA libraries: human term placenta (Clontech, Inc., Palo Alto, Calif.) and human term cytotrophoblast (Dr. J. F. Strauss, University of Pennsylvania, Philadelphia Pa.). The DNA was employed in polymerase chain reaction (PCR) amplifications (Mullis; Mullis, et al.; Perkin Elmer Cetus Corp. Norwalk Conn.). Amplification reactions were carried out for 30 cycles (45° C., 1 m; 72° C., 2 m; 94° C., 1 m) (thermal cycler and reagents, Perkin Elmer Cetus) using primers SEQ ID NO:13/SEQ ID NO:14.

Amplification products were electrophoretically separated (100 volts in a 1.5% agarose gel (Bio-Rad)) and transferred onto a nylon membrane (IBI). The membrane was baked at 80° C. for 2 hours and prehybridized and hybridized with $^{32}$P-labelled OvIFNτ cDNA as described above. The membrane was washed in 5×SSC/0.1% (wt/vol) SDS for 5 minutes at 42° C. and in 2×SSC/0.1% (wt/vol) SDS for 2 minutes at 42° C. It was then exposed at −80° C. to "XAR" (Eastman Kodak) X-ray film for 24 hours in the presence of an intensifying screen. An amplification product that hybridized with the labelled probe DNA was detected.

PCR was performed again as directed above. Amplified products were digested with the restriction endonucleases EcoRI and PstI (Promega) for 90 minutes at 37° C. The resulting DNA fragments were electrophoretically separated as described above and the band containing the IFNτ amplification product was excised from the gel. DNA fragments were recovered by electroelution, subcloned into EcoRI/PstI digested-dephosphorylated plasmid pUC19 and transformed into E. coli strain JM101 (Promega) by calcium chloride method (Sambrook, et al., 1989). The plasmids were isolated and the inserted amplification product sequenced using the dideoxy termination method (Sanger, et al., 1977; "SEQUENASE" reactions, United States Biochemical, Cleveland, Ohio.). Nucleotide sequences were determined, and comparison of these as well as the deduced amino acid sequences to other IFN sequences were performed using "DNA STAR SOFTWARE" (Madison, Wis.).

Comparison of the sequences of these clones revealed the following four different clones: from the human placental library, HuIFNτ6 (299 bp), HuIFNτ7 (288 bp) and HuIFNτ4 (307 bp), which exhibit 95% identity in their nucleotide sequences; from the cytotrophoblast library clone CTB 35 (HuIFNτ5; 294 basepairs), which shares 95% and 98% identity with HuIFNτ6 and HuIFNτ4, respectively.

EXAMPLE 7

Isolation of Full-Length Human IFNτ Genes

Ten micrograms PBMC HMW DNA was digested with restriction endonuclease EcoRI and subjected to electrophoretic analysis in a 0.8% agarose gel. A series of samples containing ranges of DNA fragments sized 1.5 to 10 kb (e.g., 1.5 to 2.5 kb, 2.5 kb to 3 kb) were excised from the gel. The DNAs were electroeluted and purified. Each DNA sample was amplified as described above using the OvIFNτ primers. The DNA molecules of any sample that yielded a positive PCR signal were cloned into λgt11 (the subgenomic λgt11 library).

A. PCR Identification of Clones Containing Sequences Complementary to OvIFNτ.

The λgt11 phage were then plated for plaques and plaque-lift hybridization performed using the $^{32}$P-labelled OvIFNτ cDNA probe. Approximately 20 clones were identified that hybridized to the probe.

Plaques that hybridized to the probe were further analyzed by PCR using the OvIFNτ primers described above. Six plaques which generated positive PCR signals were purified. The phage DNA from these clones was isolated and digested with EcoRI restriction endonuclease. The DNA inserts were subcloned into pUC19 vectors and their nucleotide sequences determined by dideoxy nucleotide sequencings.

B. Hybridization Identification of Clones Containing Sequences Complementary to PCR-Positive Phage.

Recombinant phage from the λgt11 subgenomic library were propagated in E. coli Y1080 and plated with E. coli Y1090 at a density of about 20,000 plaques/150 mm plate. The plates were overlaid with duplicate nitrocellulose filters, which were hybridized with a $^{32}$P-labelled probe from one of the six human IFNτ cDNA clones isolated above.

Clones giving positive hybridization signals were further screened and purified. The phage DNAs from hybridization-positive clones were isolated, digested with EcoRI, subcloned into pUC19 vector and sequenced. The sequence information was then analyzed.

1. HuIFNτ1

Three clones yielded over-lapping sequence information for over 800 bases relative to the mRNA cap site (clones were sequenced in both orientations). The combined nucleic acid sequence information is presented as SEQ ID NO:11 and the predicted protein coding sequence is presented as SEQ ID NO:12. Comparison of the predicted mature protein sequence (SEQ ID NO:12) of this gene to the predicted protein sequence of OvIFNτ is shown in FIG. 3.

2. HuIFNτ2, HuIFNτ3

Two additional clones giving positive hybridization signals (HuIFNτ2 and HuIFNτ3) were also screened, purified, and phage DNAs subcloned and sequenced as above. The sequences of these two clones are presented in FIGS. 19A and 19B. As can be appreciated in FIGS. 19A and 19B, the nucleotide sequence of both clones (HuIFNτ2 and HuIFNτ3) is homologous to that of HuIFNτ1 and OvIFNτ.

HuIFNτ2 (SEQ ID NO:29), may be a pseudo-gene, as it appears to contain a stop codon at position 115-117. The sequence, SEQ ID NO:29, is presented without the leader sequence. The leader sequence is shown in FIG. 20A. As can be seen from the HuIFNτ2 sequence presented in FIG. 20A, the first amino acid present in mature HuIFNτ1 (a CYS residue) is not present in the HuIFNτ2 sequence. Accordingly, the predicted amino acid sequence presented as SEQ ID NO:29 corresponds to a mature IFNτ protein with the exceptions of the first CYS residue and the internal stop codon.

The internal stop codon in the nucleic acid coding sequence can be modified by standard methods to replace the stop codon with an amino acid codon, for example, encoding GLN. The amino acid GLN is present at this position in the other isolates of human IFNτ (HuIFNτ). Standard recombinant manipulations also allow introduction of the initial CYS residue if so desired.

HuIFNτ3 (SEQ ID NO:31), appears to encode a human IFNτ protein. The translated amino acid sequence of the entire protein, including the leader sequence, is presented as SEQ ID NO:32. The translated amino acid sequence of the mature protein is presented as SEQ ID NO:34.

EXAMPLE 8

Analysis of the Presence of HuIFNτ mRNA by RT-PCR

Human placental cDNA libraries and an ovine cDNA library, constructed from day 15–16 conceptuses, were analyzed by hybridization to the OvIFNτ cDNA probe, described above. cDNAs were size-fractionated on agarose gels and transferred to filters (Manitias, et al.; Sambrook, et al.). Southern blot analysis with OvIFNτ probe showed that the autoradiographic signals from human cDNA libraries were approximately 1/100 of the signal obtained using the OvIFNτ cDNA library.

The presence of HuIFNτ mRNA in human term placenta and amniocytes (26 weeks, 2 million cells) was analyzed by using reverse transcriptase-PCR (RT-PCR) method (Clontech Laboratories, Palo Alto Calif.).

Total cellular RNA (tcRNA) isolated from human placenta, amniocytes and ovine conceptuses were reverse transcribed using the primer SEQ ID NO:14. The primer SEQ ID NO:13 was then added to the reaction and polymerase chain reaction carried out for 40 cycles. The PCR products were size fractionated on agarose gels and transferred to filters. The DNA on the filters was hybridized with $^{32}$P-labelled OvIFNτ and HuIFNτ cDNAs. The results of these analyses demonstrate the presence of human IFNτ mRNA in the feto-placental annex. The aminocytes also expressed the messages corresponding to OvIFNτ primers and human probe.

In addition, a RT-PCR analysis for the presence of HuIFNτ was applied to the tcRNA isolated from human adult lymphocytes. A densitometric analysis revealed that IFNτ mRNA exists in lymphocytes.

EXAMPLE 9

In Situ Hybridization

A. Tissue

Slides of semiserial 5-µ paraffin embedded sections from four healthy, different term and first trimester human placentas were examined.

B. cRNA Probe Preparation

From the cDNA clone isolated from OvIFNτ amplified library a fragment corresponding to the OvIFNτ cDNA bases #77-736 (base #1 is cap site; open reading frame of OvIFNτ cDNA is base #81-665; FIG. 7) was subcloned into the transcription vector, pBS (New England Biolabs). Several pBS clones were isolated, subcloned, and their nucleotides sequenced. From this clone a 3' fragment (bases #425-736) was excised using the restriction endonucleases NlaIV and EcoRI and subcloned into the transcription vector pBS. This vector was designated pBS/OvIFNτ.

After linearization of the pBS/OvIFNτ plasmid, an anti-sense cRNA probe was synthesized by in vitro transcription (Sambrook, et al., 1989) using $T_7$ RNA polymerase (Stratagene). A trace amount of $^3$H-CTP (NEN-DuPont, Cambridge, Mass.) was used in the transcription reaction. dUTP labeled with digoxigenin (Boehringer-Mannheim, Indianapolis, Ind.) was incorporated into the cRNA and yield was estimated through TCA precipitation and scintillation counting.

C. Hybridization

In situ hybridization was performed using the anti-sense RNA probe, as described by Lawrence, st al. (1985) with the following modifications. Deparaffinized and hydrated sections were prehybridized for 10 minutes at room temperature in phosphate buffered saline (PBS) containing 5 mM $MgCl_2$. Nucleic acids in the sections were denatured for 10 minutes at 65° C. in 50% formamide/2×SSC. Sections were incubated overnight at 37° C. with a hybridization cocktail (30 µl/slide) containing 0.3 µg/ml digoxigenin-labelled cRNA probe and then washed for 30 minutes each at 37° C. in 50 formamide/1×SSC. Final washes were performed for 30 minutes each at room temperature in 1×SSC and 0.1×SSC. The sections were blocked for 30 minutes with 0.5% Triton X-100 (Sigma) and 0.5% non-fat dry milk.

Hybridization signal was detected using purified sheep antidioxigenin Fab fragments conjugated to alkaline phosphatase (Boehringer-Mannheim). After unbound antibody was removed, nitroblue tetrazolium/5-bromo-4-chloro-3-indolyl-phosphate substrate (Promega) and levamisole (Bector Laboratories, Burlingame, Calif.) were added for signal detection via colorimetric substrate generation. The tissues were counterstained in methyl green (Sigma), dehydrated, and mounted.

As a control, some tissue sections were pretreated with 100 µg/ml of pancreatic RNaseA (Sigma) for 30 minutes at 37° C. The RNase was inactivated on the slide with 400 units of RNase inhibitor (Promega). The slides were then washed twice in 250 ml of PBS/5 mM $MgCl_2$. In other control experiments, tRNA (Sigma) was substituted for the digoxigenin probes.

Specific hybridization was observed in all term and first trimester placental tissues in three separate experiments with various OvIFNτ cRNA probe concentrations and blocking reagents.

First trimester placental villi composed of an outer layer of syncytiotrophoblast, an underlying layer of cytotrophoblast, and a central stromal region with various types of mesenchymal cells, displayed the highest transcript level of IFNτ in the cytotrophoblast cells. Less intense but detectable levels were present in both the syncytiotrophoblast and stromal cells. A similar pattern of transcript expression was demonstrated in the placental villi of term tissue but the level of signal detection was low. First trimester extravillous trophoblast displayed the highest amount of message and stained positive when present in the maternal blood spaces.

EXAMPLE 10

Antiviral Activity of IFNτ

The relative specific activity of OvIFNτ, purified to homogeneity, was evaluated in antiviral assays. The antiviral assays were performed essentially as described above in Example 2. Specific activities are expressed in antiviral units/mg protein obtained from antiviral assays using either Madin-Darby bovine kidney (MDBK) cells or sheep normal fibroblasts (Shnf). All samples were assayed simultaneously to eliminate interassay variability. The results, presented in Table 3, are the means of four determinations where the standard deviation was less than 10% of the mean.

TABLE 3

Antiviral Activity of IFNτ and Known IFNs

| | Specific Activities | |
|---|---|---|
| | MDBK | Shnf |
| OvIFNτ | $2 \times 10^8$ | $3 \times 10^8$ |
| rBoIFNα | $6 \times 10^7$ | $1 \times 10^7$ |
| rBoIFNγ | $4.5 \times 10^6$ | $3 \times 10^6$ |
| NIH rHuIFNα | $2.2 \times 10^8$ | $2.2 \times 10^8$ |
| rHuIFNα | $2.9 \times 10^5$ | $4.3 \times 10^5$ |

IFNτ had a higher specific activity than either rBoIFNα or rBoIFNγ (Table 3). The NIH standard preparation of rHuIFNα had a similar specific activity, while a commercial preparation of rHuIFNα exhibited low specific antiviral activity. Comparable relative antiviral activity was demonstrated using either bovine or ovine cells.

EXAMPLE 11

Anti-Retroviral Activity and Cytotoxic Effects of IFNτ

Highly purified OvIFNτ was tested for anti-retroviral and cytotoxic effects on feline peripheral blood lymphocytes exposed to the feline immunodeficiency retrovirus. This lentivirus produces a chronic AIDS-like syndrome in cats and is a model for human AIDS (Pederson, et al., 1987). Replication of the virus in peripheral blood lymphocytes is monitored by reverse transcriptase activity in culture supernatants over time. The data from these assays are presented in Table 4.

TABLE 4

Effect of OvIFNτ on FIV Replication

| IFNτ Concentration (ng/ml) | RT Activity (cpm/ml) | | | | |
|---|---|---|---|---|---|
| | Harvest Days | | | | |
| Experiment 1 | Day 2 | Day 5 | Day 8 | Day 12 | Day 15 |
| 0.00 | 93,908 | 363,042 | 289,874 | 171,185 | 125,400 |
| 0.62 | 77,243 | 179,842 | 172,100 | 218,281 | 73,039 |
| 1.25 | 94,587 | 101,873 | 122,216 | 71,916 | 50,038 |
| 2.50 | 63,676 | 72,320 | 140,783 | 75,001 | 36,105 |
| 5.00 | 69,348 | 82,928 | 90,737 | 49,546 | 36,299 |
| | Harvest Days | | | | |
| Experiment 2 | Day 2 | Day 5 | Day 8 | Day 13 | Day 17 |
| 0.0 | 210,569 | 305,048 | 279,556 | 500,634 | 611,542 |
| 2.5 | 121,082 | 106,815 | 108,882 | 201,676 | 195,356 |
| 5.0 | 223,975 | 185,579 | 108,114 | 175,196 | 173,881 |
| 10.0 | 167,425 | 113,631 | 125,131 | 131,649 | 129,364 |
| 20.0 | 204,879 | 80,399 | 59,458 | 78,277 | 72,179 |
| 40.0 | 133,768 | 54,905 | 31,606 | 72,580 | 53,493 |

Addition of OvIFNτ produced a rapid, dose-dependent decrease in reverse transcriptase (RT) activity (Table 4). While concentrations as low as 0.62 ng/ml of IFNτ inhibited viral replication, much higher concentrations (40 ng/ml) having greater effects on RT-activity were without toxic effects on the cells. The results suggest that replication of the feline immunodeficiency virus was reduced significantly compared to control values when cells were cultured in the presence of OvIFNτ.

IFNτ appeared to exert no cytotoxic effect on the cells hosting the retrovirus. This was true even when IFNτ was present at 40 ng per ml of culture medium.

EXAMPLE 12

Effects of INFτ on HIV Infected Human Peripheral Lymphocytes

IFNτ was also tested for activity against HIV infection in human cells. Human peripheral blood lymphocytes, which had been infected with HIV (Crowe, et al.), were treated with varying concentrations of OvIFNτ. Replication of HIV in peripheral blood lymphocytes was monitored by reverse transcriptase activity in culture supernatants over time. Reverse transcriptase activity was measured essentially by the method of Hoffman, et al. The data from these assays are presented in Table 5.

TABLE 5

Effect of OvIFNτ on HIV Replication in Human Peripheral Lymphocytes

| IFNτ Concentration (ng/ml) | RT Activity | | | |
|---|---|---|---|---|
| | Day 6 | | Day 10 | |
| | cpm/ml | % Reduction | cpm/ml | % Reduction |
| 0 | 4,214 | — | 25,994 | — |
| 10 | 2,046 | 51 | 9,883 | 62 |
| 50 | 1,794 | 57 | 4,962 | 81 |
| 100 | 1,770 | 58 | 3,012 | 88 |
| 500 | 1,686 | 60 | 2,670 | 90 |
| 1000 | 1,499 | 64 | 2,971 | 89 |

As shown in Table 5, concentrations of OvIFNτ produced significant antiviral effects. A concentration of only 10 ng/ml resulted in over a 50% reduction in RT activity after only six days. A concentration of 500 ng/ml resulted in a 90% reduction in RT activity within 10 days.

The viability of human peripheral blood lymphocytes after treatment with IFNτ, over a range of concentrations for 3–13 days, was evaluated by trypan blue exclusion. The results of this viability analysis are presented in Table 6.

TABLE 6

Effect of OvIFNτ on Viability of HIV Infected Human Peripheral Lymphocytes

| IFNτ Concentration (ng/ml) | Viable Cells/ml × $10^5$ | | |
|---|---|---|---|
| | Day 3 | Day 6 | Day 13 |
| 0 | 16.0 | 7.5 | 5.3 |
| 10 | 13.0 | 7.5 | 6.0 |
| 50 | 13.0 | 11.5 | 9.0 |
| 100 | 15.0 | 8.5 | 9.5 |
| 500 | 16.5 | 12.0 | 11.0 |
| 1000 | 21.9 | 9.5 | 8.5 |

The data presented in Table 6 show no evidence of cytotoxic effects attributable to the administration of IFNτ.

EXAMPLE 13

Inhibition of Cellular Growth

The effects of IFNτ on cellular growth were also examined. Anti-cellular growth activity was examined using a colony inhibition assay. Human amnion (WISH) or MDBK cells were plated at low cell densities to form colonies originating from single cells. Cells were cultured at 200 or 400 cells/well in 24 well plates in HMEM supplemented with 2% fetal bovine serum (FBS) and essential and non-essential amino acids. Various dilutions of interferons were added to triplicate wells, and the plates were incubated for 8 days to allow colony formation. Colonies were visualized after staining with crystal violet, and counted. Cell cycle analysis was performed with HMEM containing 0.5% "spent" media for an additional 7 days. WISH cells were used without being synchronized.

For examination of IFNτ activity, cells were replated at $2.5 \times 10^5$ cells/well in HMEM with 10% FBS in 6 well plates. Various dilutions of OvIFNτ alone or in combination with peptides were added to achieve a final volume of 1 ml. Plates were incubated at 37° C. in 5% $CO_2$ for 12, 15, 18, 24, or 48 hours. Cells were treated with trypsin, collected by low speed centrifugation and washed. The cell pellet was blotted dry and 250 µl of nuclear staining solution (5 mg propidium iodide, 0.3 ml NP40 and 0.1 gm sodium citrate in 100 ml distilled $H_2O$) was added to each tube. The tubes were incubated at room temperature. After 10 minutes, 250 µl of RNase (500 units/ml in 1.12% sodium citrate) was added per tube and incubated an additional 20 minutes. Nuclei were filtered through 44 µm mesh, and analyzed on a FACStar (Becton Dickinson, Mountain View, Calif.) using the DNA Star 2.0 software.

In the cellular growth assay using colony formation of both the bovine epithelial line, MDBK, and the human amniotic line, WISH, OvIFNτ inhibited both colony size and number. Ovine IFNτ was more effective than human IFNα on the human cell line; thus, it is very potent in cross-species activity. Its activity was dose-dependent, and inhibition of proliferation could be observed at concentrations as low as 1 unit/ml. Concentrations as high as 50,000 units/ml (units of antiviral activity/ml) stopped proliferation, while cell viability was not impaired.

Cell cycle analysis by flow cytometry with propidium iodide-stained WISH cells revealed an increased proportion of cells in G2/M after 48 hours of OvIFNτ treatment. IFNτ, therefore, appears to inhibit progress of cells through S phase. Ovine IFNτ antiproliferative effects can be observed as early as 12 hours after the initiation of culture and are maintained through 6 days.

The results presented above demonstrate both the antiproliferative effect of IFNτ as well as its low cytotoxicity.

EXAMPLE 14

Further Antiproliferative Effects of IFNτ

The antiproliferative effects of OvIFNτ were studied for a rat cell line and a bovine cell line. The rate of $^3$H-thymidine incorporation was used to assess the rate of cellular proliferation.

Rat (MtBr7 .c5) or bovine kidney (MDBK) cells were seeded in phenol red-free DME-F12 medium supplemented with 3% dextran-coated charcoal stripped Controlled Process Serum Replacement 2 (CPSR 2, Sigma) and 5% dextran-coated charcoal stripped fetal bovine serum (FBS). After attaching for approximately 15–18 hours, the cells were washed once with serum-free DME-F12 medium. The medium was replaced with phenol red-free DME-F12 medium supplemented with 3% stripped CPSR2, 1% stripped FBS ("3/1" medium) or 3/1 medium containing OvIFNτ at various units of antiviral activity as determined in the vesicular stomatitis virus challenge assay for interferons (Example 2). Media containing a similar dilution of buffer (undiluted buffer=10 mM Tris, 330 mM NaCl, [TS]), in which the OvIFNτ was dissolved was used for controls.

Cells were pulse labeled with $^3$H-thymidine for 2 hours at approximately 48 hours post-treatment. The trichloroacetic acid (TCA) precipitable incorporated counts were determined by scintillation counting. Three replicates were included per treatment. Mean values for OvIFNτ treatments were compared to samples containing comparable dilutions of carrier TS buffer. Results of these experiments are shown in Table 7.

TABLE 7

| | $^3$H-Thymidine Incorporation |
|---|---|
| Treatment | % Reduction $^3$H-Thymidine Incorporation |
| Experiment 1: MtBr7 .c5 (Rat) | |
| 3/1 | — |
| $10^3$ u OvIFNτ/ml | 0 (+12) |
| 1:5000 TS | — |
| $10^4$ u OvIFNτ/ml | 24 |
| 1:500 TS | — |
| $10^5$ u OvIFNτ/ml | 87 |
| Experiment 2: MDBK | |
| 3/1 | — |
| $10^3$ u OvIFNτ/ml | 74 |
| 1:5000 TS | — |
| $10^4$ u OvIFNτ/ml | 83 |
| 1:500 TS | — |
| $10^5$ u OvIFNτ/ml | 83 |

As can be seen from Table 7, OvIFNτ drastically reduced the rate of cellular proliferation (based on thymidine incorporation) for each of the cell lines tested.

EXAMPLE 15

Antiproliferative Effects of IFNτ on Human Tumor Cell Lines

The antiproliferative activity of OvIFNτ on human tumor cell lines was evaluated by measuring the rate of $^3$H-thymidine incorporation into cells which have been treated with OvIFNτ.

For experiments on tumor lines that grow in suspension, 1 ml of cells were plated at from 2.5–5×$10^5$ cells/well in 24-well plates. Triplicate wells received either the appropriate media, 100, 1,000 or 10,000 units/ml of OvIFNτ or equivalent antiviral concentrations of rHuIFNα2A (Lee Biomolecular). After 48 hours of incubation, cells were counted and viability assessed by trypan blue exclusion.

Adherent tumor lines were plated at 2.5×$10^5$ cells/well in 1 ml in 6-well plates. They received interferon treatments as just described, but were trypsinized prior to counting.

Significant differences between treatments were assessed by an analysis of variance followed by Scheffe's F-test. Cell cycle analysis was performed by flow cytometry using propidium iodide.

A. Breast Adenocarcinoma Cells.

Human MCF7 breast adenocarcinoma cells were seeded from logarithmically growing cultures in phenol red-free DME-F12 medium supplemented with 3% dextran-coated charcoal stripped CPSR and 5% dextran-coated FBS. After attaching for approximately 15–18 hours, the cells were washed once with serum-free DME-F12 medium. The medium was replaced with phenol red-free DME-F12 medium supplemented with 3% stripped CPSR2, 1% stripped FBS ("3/1" medium) or 3/1 medium containing OvIFNτ at the indicated number of units of antiviral activity as determined in the vesicular stomatitis virus challenge assay for interferons. Media containing a similar dilution of buffer (undiluted buffer=10 mM Tris, 330 mM NaCl [TS]) was used for controls. Cells were pulse labeled with $^3$H-thymidine for 2 hours at approximately 48 hours post-treatment.

The trichloroacetic acid (TCA) precipitable incorporated counts were determined by scintillation counting. Three replicates were included per treatment. Mean values for OvIFNτ treatments were compared to samples containing comparable dilutions of carrier TS buffer. The results of these analyses are shown in Table 8.

TABLE 8

$^3$H-Thymidine Incorporation

| Treatment | % Reduction $^3$H-Thymidine Incorporation |
|---|---|
| MCF7 Human | |
| 3/1 | — |
| $10^3$ u OvIFNτ/ml | 35 |
| 1:5000 TS | — |
| $10^4$ u OvIFNτ/ml | 53 |
| 1:500 TS | — |
| $10^5$ u OvIFNτ/ml | 70 |

As can be seen from the results shown in Table 8, OvIFNτ was able to substantially reduce the rate of $^3$H-thymidine incorporation in the human carcinoma cell line. This demonstrates the efficacy of OvIFNτ in inhibiting tumor cell proliferation, in particular, mammary tumor cell proliferation.

B. Human Promyelocytic Leukemia.

A comparison of the antiproliferative effects of OvIFNτ and IFNα was conducted using HL-60 (human leukemia) cells (Foa, et al.; Todd, et al.) essentially as described above for MDBK cells. Both OvIFNτ and rHuIFNα inhibit HL-60 cell proliferation. Results of one of three replicate experiments are presented as mean % growth reduction±SD in FIG. 4. FIG. 4 shows that both OvIFNτ and IFNα were able to drastically reduce growth of HL-60 cells. The growth reduction for each compound exceeded 60% for each concentration tested. At 10,000 units/ml, OvIFNτ caused an approximately 80% reduction in growth while IFNα caused a 100% reduction in growth.

However, the data presented in FIG. 4 reveal, that a substantial factor in the ability of IFNα to reduce growth was its toxic effect on the cells. At 10,000 units/ml, the toxicity of IFNα resulted in less than 25% of the cells remaining viable. By contrast, nearly 100% of the cells remained viable when OvIFNτ was applied at 10,000 units/ml.

FIG. 5 presents data demonstrating that rHuIFNα is cytotoxic. In the figure, results of one of three replicate experiments are presented as mean % viability±SD.

C. Human Cutaneous T Cell Lymphoma.

The cutaneous T cell lymphoma, HUT 78, responded similarly to HL-60 when treated with IFNτ (FIG. 9). Both OvIFNτ and rHuIFNα reduce HUT 78 cell growth, but 10,000 units/ml of rHuIFNα decreased the cell number below that originally plated (5×10$^5$). This is indicative of a reduction in cell viability to approximately 60%.

Cell cycle analysis (performed by cell flow cytometry) revealed an increased proportion of cells in G2/M phase of the cell cycle upon 48 hours of treatment with both interferons (Table 9). In Table 9 the results from one of three replicate experiments are presented as the percentage of cells in each phase of the cell cycle. 10,000 events were analyzed per sample.

This result is likely due to the slower progress of cells through the cell cycle. In the sample treated with 10,000 units/ml of rHuIFNα, a large percentage of events with low forward and high side scatter, identifying dead cells, were present. This is consistent with the data obtained from proliferation experiments, where only OvIFNτ inhibited HUT 78 proliferation without toxicity.

TABLE 9

HUT 78 Cell Cycle Analysis.

| Treatment (units/ml) | G0/G1 | S | G2/M |
|---|---|---|---|
| Media | 44.43 | 49.95 | 5.61 |
| 100 OvIFNτ | 44.35 | 47.45 | 8.20 |
| 100 rHuIFNα | 40.01 | 57.53 | 2.45 |
| 1,000 OvIFNτ | 41.29 | 50.50 | 8.21 |
| 1,000 rHuIFNα | 41.73 | 44.91 | 13.36 |
| 10,000 OvIFNτ | 42.79 | 42.61 | 14.60 |
| 10,000 rHuIFNα | 18.01 | 71.31 | 10.67 (cell death) |

D. Human T Cell Lymphoma.

The T cell lymphoma cell line H9 was slightly less sensitive to the antiproliferative effects of the IFNs than the tumor cell lines described above. Results of one of three replicate experiments are presented in FIG. 10 as mean % growth reduction±SD. While rHuIFNα was not toxic to the H9 cells, it failed to inhibit cell division significantly at any of the concentrations examined. In contrast, OvIFNτ was observed to reduce H9 growth by approximately 60% (FIG. 10). Thus, only OvIFNτ is an effective growth inhibitor of this T cell lymphoma.

The results presented above demonstrate both the antiproliferative effect of IFNτ as well as its low cytotoxicity.

EXAMPLE 16

Preliminary In Vivo Treatment with OvIFNτ

Three groups of 4 C57Bl/6 mice per group were given 2.5×10$^4$ B16-F10 cells via the tail vein: B16-F10 is a syngeneic mouse transplantable tumor selected because of its high incidence of pulmonary metastases (Poste, et al., 1981). Interferon treatment was initiated 3 days after the introduction of the tumor cells. Each mouse received 100 μl of either PBS alone, PBS containing 1×10$^5$ units of OvIFNτ, or PBS containing 1×10$^5$ units of recombinant murine IFNα (MuIFNα), i.v. per day for 3 consecutive days.

Mice were sacrificed at 21 days and the lungs were preserved in 10% buffered formalin. The frequency of pulmonary metastases were compared between control mice (PBS), OvIFNτ-treated mice, and MuIFNα-treated mice. The results of these in vivo administrations demonstrated that OvIFNτ dramatically reduced B16-F10 pulmonary tumors. These results support the use of IFNτ as an efficacious antineoplastic agent in vivo.

EXAMPLE 17

Competitive Binding of IFNτ Peptide Fragments

A. The Ability of IFNτ-Based Peptides to Block INFτ and IFN-α Antiviral Activity.

Overlapping synthetic peptides were synthesized corresponding to the entire IFNτ sequence (FIG. 6). Average hydropathicity values were calculated by taking the sum of the hydropathy values for each amino acid divided by the total number of amino acids in each sequence. Hydropathy values were taken from Kyte, et al. (1982).

These peptides were of approximately the same molecular weight but differed slightly in overall hydrophilicity. Despite this difference, all peptides were antigenic as demonstrated by the production of rabbit antisera with titers greater than 1:3,000 as assessed by ELISA (Harlow, et al.).

Figure 12:
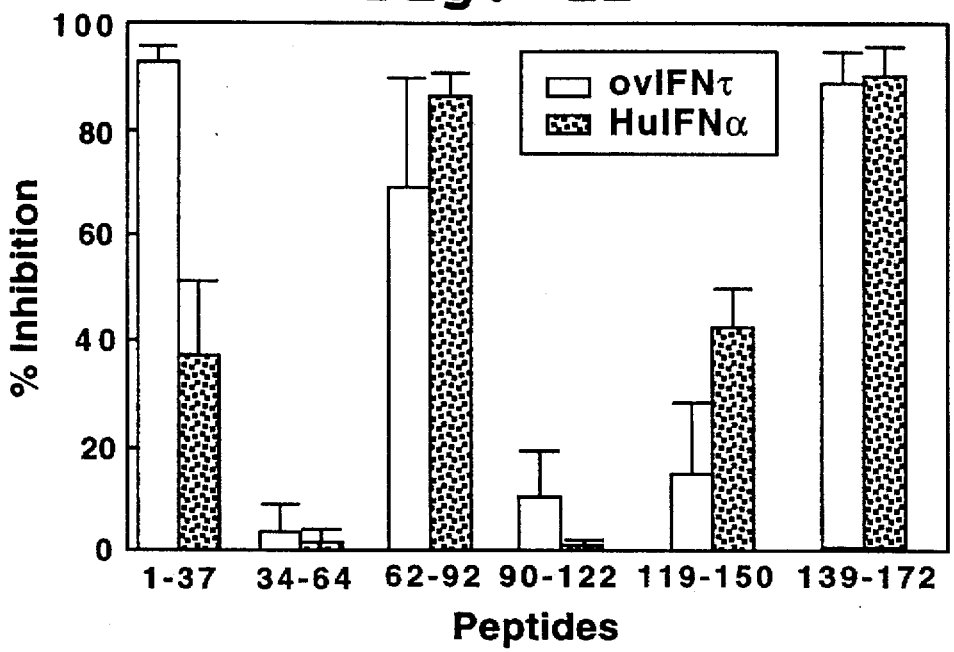
FIG. 12 presents data demonstrating the inhibition of the antiviral activity of IFNτ by IFNτ-derived peptides.

The peptides were used to inhibit the antiviral activity (Example 2) of OvIFNτ and rBoIFNα. The results of this analysis are presented in FIG. 12: 1 mM N- and C-terminal peptides both effectively blocked the antiviral activity of OvINFτ using MDBK cells. A third peptide, representing amino acids 62-92, also reduced IFNτ antiviral activity (70% inhibition). The peptide OvIFNτ (119-150) showed minimal inhibitory activity. The OvIFNτ (34-64) and (90-122) peptides had no apparent inhibitory activity.

Figure 13:
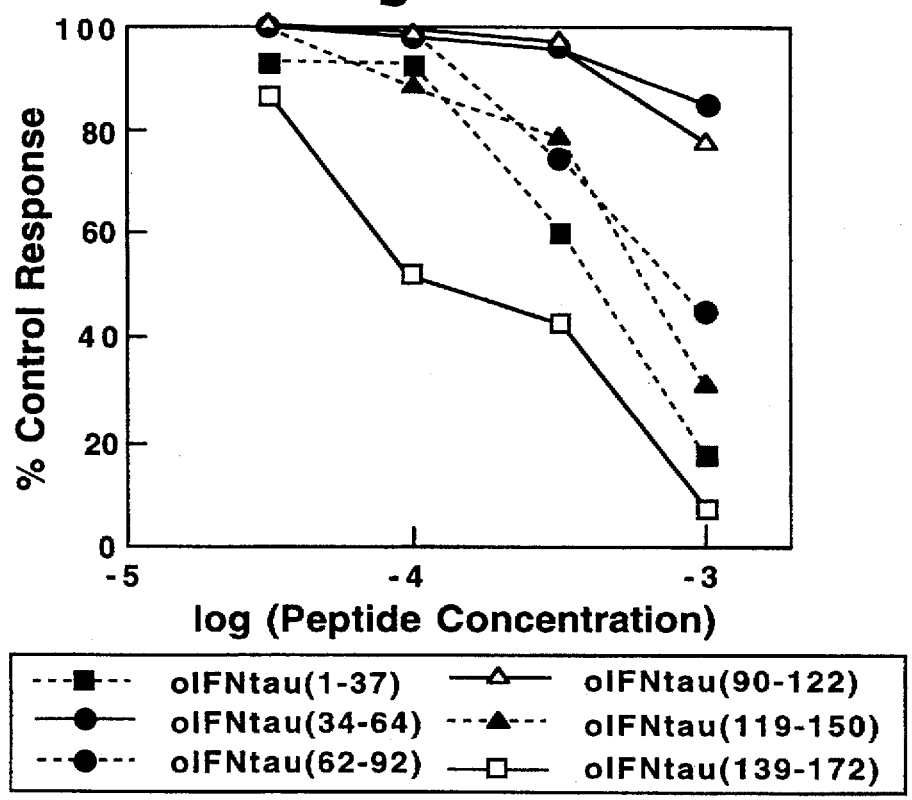
FIG. 13 presents data demonstrating the inhibition by IFNτ-derived peptides of OvIFNτ antiviral activity.

Peptide inhibition of OvIFNτ antiviral activity was also examined as follows. Monolayers of Madin Darby bovine kidney cells were incubated with 40 units/ml OvIFNτ in the presence or absence of various concentrations of OvIFNτ peptides (see FIG. 13). Results in FIG. 13 are expressed as the percent of control antiviral activity: that is, in the absence of any competing peptide. Data presented are the means of 6 replicate experiments. The data demonstrate that inhibition by OvIFNτ (1-37), (62-92), (119-150), and (139-172) were significantly different than OvIFNτ (34-64) and (90-122) at $10^{-3}$M and $3\times10^{-3}$M. OvINFτ (139-172) was significantly different than all other peptides at $10^{-3}$M. Significance was assessed by analysis of variance followed by Scheffé's F test at $p<0.05$. Thus, OvIFNτ (1-37) (62-92), (119-150), and (139-172), in particular (139-172), may represent receptor binding regions for IFNτ.

The ability of the OvIFNτ peptides to inhibit bovine IFNα (BoIFNα) antiviral activity was examined as follows. Monolayers of Madin Darby bovine kidney cells were incubated with 40 units/ml bovine IFNα in the presence or absence of various concentrations of OvIFNτ peptides. The results are presented in FIG. 14 and are expressed as the percent of control antiviral activity in the absence of OvIFNτ peptides. The data presented are the means of 4 replicate experiments. The results indicate that inhibition by OvIFNτ (62-92), (119-150), and (139-172) were significantly different from OvIFNτ (1-37), (34-64) and (90-122) at $10^{-3}$M. OvIFNτ (139-172) was significantly different than OvIFNτ (1-37), (34-64) and (90-122) at $3\times10^{-3}$M. Significance was assessed by analysis of variance followed by Scheffé's F test at $p<0.05$. Thus, OvIFNτ (62-92), (119-150), and (139-172), in particular (139-172), may represent common receptor binding regions for IFNτ and bovine IFNα.

Peptide inhibition by OvIFNτ peptides of human IFNα antiviral activity was also examined. Monolayers of Madin Darby bovine kidney cells were incubated with 40 units/ml human IFNα in the presence or absence of various concentrations of OvIFNτ peptides. The results are expressed as the percent of control antiviral activity in the absence of OvIFNτ peptides. The data are presented in FIG. 15 and are the means of 3 replicate experiments. OvIFNτ (139-172) was significantly different from all other peptides at $10^{-3}$M. Significance was assessed by analysis of variance followed by Scheffé's F test at $p<0.05$. Thus, OvIFNτ (139-172) may represent a common receptor binding region for IFNτ and various IFNα(s).

Figure 16:
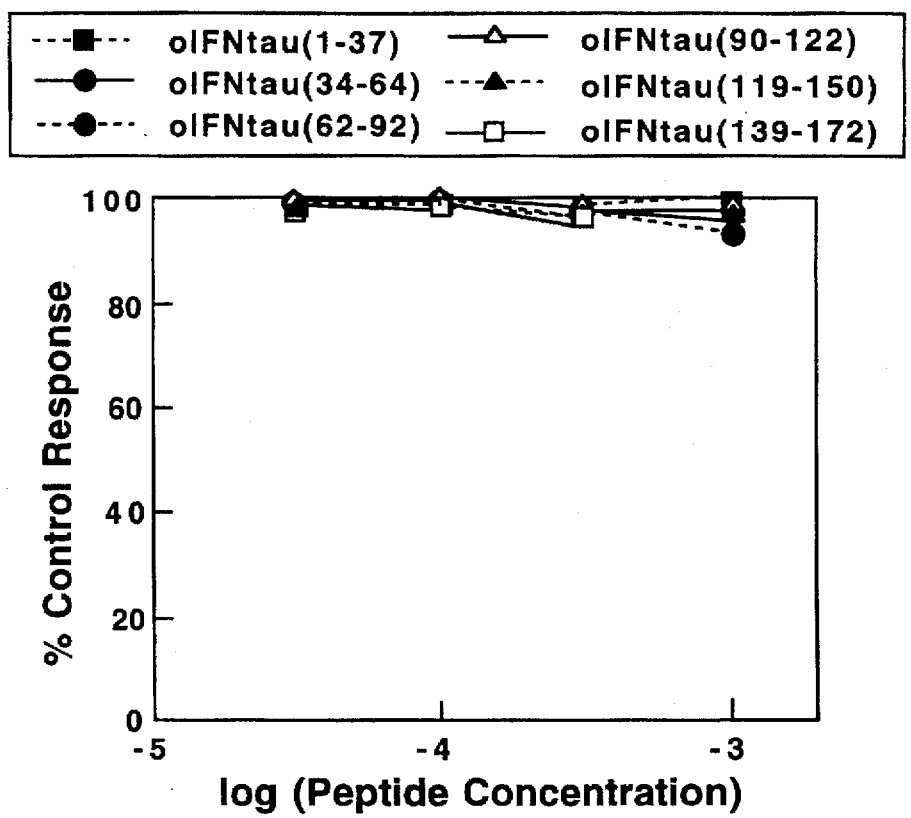
FIG. 16 presents data evaluating the lack of inhibition by IFNτ-derived peptides of bovine IFNγ antiviral activity.

The OvIFNτ peptides described above appear to have no effect on the antiviral activity of IFNγ. Peptide inhibition of bovine IFNγ antiviral activity was evaluated as follows. Monolayers of Madin Darby bovine kidney cells were incubated with 40 units/ml bovine IFN gamma in the presence or absence of various concentrations of OVIFNτ peptides. Results are expressed as the percent of control antiviral activity in the absence of OvIFNτ peptides. The data are presented in FIG. 16 and are the means of 3 replicate experiments. There were no significant differences among peptides as assessed by analysis of variance followed by Scheffé's F test at $p<0.05$.

The two synthetic peptides OvIFNτ (1-37) and OvIFNτ (139-172) also blocked OvIFNτ anti-FIV and anti-HIV activity. Reverse transcriptase (RT) activity (Examples 12 and 13) was monitored over a 14 day period in FIV-infected FET-1 cells ($1\times10^6$/ml) and HIV-infected HPBL ($1\times10^6$/ml). Control cultures received no OvIFNτ. OvIFNτ was used at 100 ng/ml, and peptides were used at 200 µM. Data from a representative experiment are expressed as cpm/ml culture supernatant and are presented for FIV infected cells, FIG. 11A, and HIV infected cells, FIG. 11B. Both the N- and C-terminus of OvIFNτ appear to be involved in its anti-retroviral activity. While both peptides blocked FIV RT activity, only the C-terminal peptide, OvIFNτ (139-172), was an efficient inhibitor of vesicular stomatitis virus activity on the feline cell line, Fc9. Thus the C-terminal regions of type I IFNs may bind to common site on the type I IFN receptor, while the N-terminal region may be involved in the elicitation of unique functions.

B. Anti-Peptide Sera.

Figure 17:
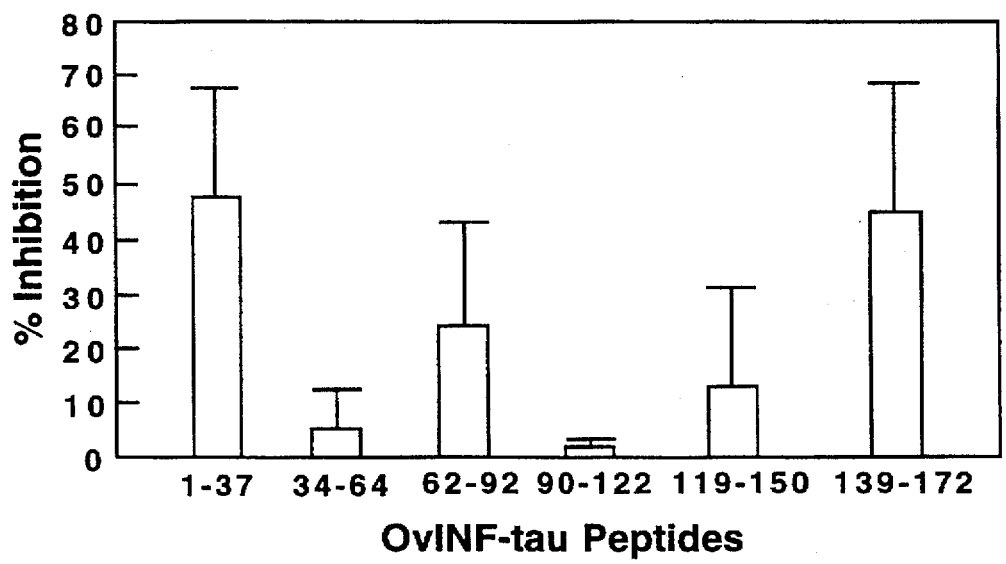
FIG. 17 presents data demonstrating the anti-IFNτ-derived peptide antisera inhibition of the antiviral activity of IFNτ.

The ability of anti-peptide antisera to inhibit OvIFNτ antiviral activity was also determined. Antipeptide antisera inhibition of OvIFNτ antiviral activity was evaluated as follows. Monolayers of MDBK cells were incubated with 20 units/ml of OvIFNτ in the presence a 1:30 dilution of either preimmune sera or antisera to each of the OvIFNτ peptides described above. In FIG. 17 the data from duplicate experiments are presented as the mean percent inhibition of OvIFNτ antiviral activity produced by antipeptide antisera relative to the appropriate preimmune sera±standard error. Significant differences were assessed by analysis of variance followed by Scheffé's F test at $p<0.05$. Consistent with peptide inhibition of antiviral activities, sera containing antibodies immunoreactive to OvIFNτ (1-37), OvIFNτ (62-92), and OvIFNτ (139-172) were also the most effective inhibitors of OvIFNτ antiviral activity, with antibodies directed against the N-terminal and C-terminal peptides being the most efficacious.

The same sera were also used to examine their effect on the binding of IFNτ to its receptor.

Figure 18:
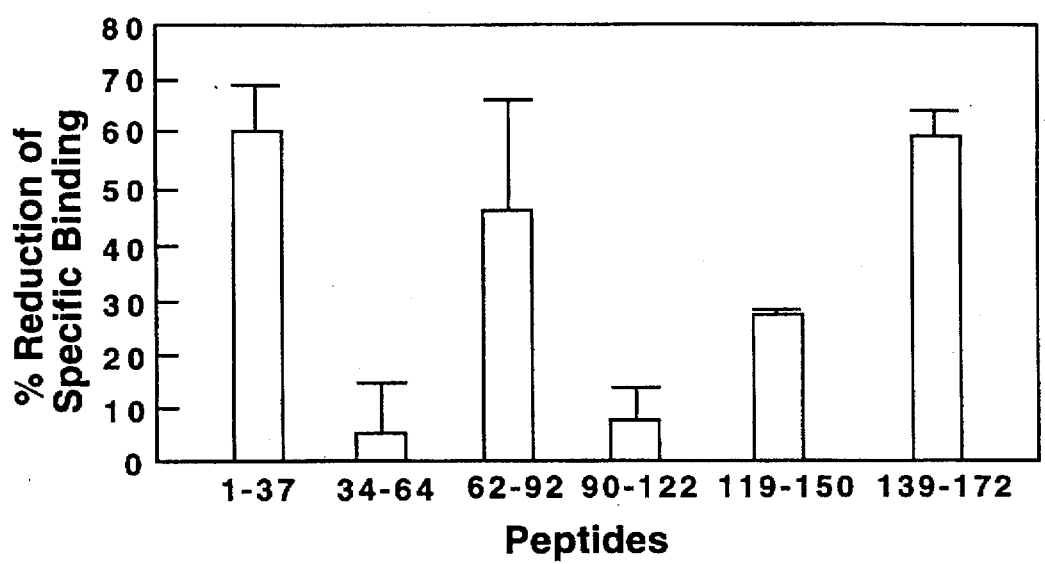
FIG. 18 presents data demonstrating the anti-IFNτ-derived peptide antisera inhibition of the binding of radio-labeled IFNτ to cells.

The IFNτ binding assay was carried out as follows. Five µg of IFNτ was iodinated for 2 minutes with 500 µCi of Na$^{125}$ I (15 mCi/µg; Amersham Corporation, Arlington Heights, Ill.) in 25 µl of 0.5M potassium phosphate buffer, pH 7.4, and 10 µl of chloramine-T (5 mg/ml) (Griggs, et al., 1992). The specific activity of the iodinated protein was 137 µCi/µg. For binding assays, monolayers of MDBK cells were fixed with paraformaldehyde and blocked with 5% nonfat dry milk. Cells were incubated with 5 nM $^{125}$I-IFNτ in phosphate buffered saline with 1% BSA for 2 hours at 4° C. in the presence or absence of a 1:30 dilution of sera containing antibodies raised against IFNτ peptides or the appropriate preimmune sera. Specific binding was assessed by incubation with a 100-fold molar excess of unlabeled IFNτ. Specific binding of 36% was determined by competition with 500 nM unlabeled IFNτ. For example, total counts bound were 6850±133, and a 100-fold molar excess of OvIFNτ produced 4398±158 counts per minute. After incubation, the monolayers were washed three times, solubilized with 1% sodium dodecyl sulfate, and the radioactivity counted. Data from three replicate experiments are presented in FIG. 18 as the mean percent reduction of OvIFNτ specific binding produced by antipeptide antisera relative to the appropriate preimmune sera±standard deviation. Significant differences were assessed by analysis of variance followed by Scheffe's F test.

The same sera (containing antibodies immunoreactive to OvIFNτ (1-37), OvIFNτ (62-92), and OvIFNτ (139-172)) were the most effective inhibitors of $^{125}$I-IFNτ binding to its receptor on MDBK cells. The lack of effect of sera immunoreactive with other IFNτ-derived peptides was not a function of titer against OvIFNτ, since each sera had equal or greater titer to their respective peptide relative to the three inhibiting sera: similar results were obtained when sera reactivity against the whole OvIFNτ molecule was assessed by ELISA for each sera.

These peptides, although apparently binding to the interferon receptor, did not in and of themselves elicit interferon-like effects in the cells.

C. Anti-Proliferative Activity.

Functionally important sites for the antiproliferative activity of IFNτ were also examined using synthetic peptides (Table 10). Cellular proliferation was assayed as described above using MDBK cells. MDBK cells were cultured at $5 \times 10^5$ cells/well in experiments 1 and 2 or $10 \times 10^5$ cells in experiment 3 and treated with medium alone, IFNτ at a concentration of 300 units/ml and peptides at 1 mM for 48 hours. Duplicate wells were counted in each of three replicate experiments. For statistical analysis, data were normalized based on medium alone and assessed by analysis of variance followed by Least Significant Difference multiplate comparison test (p>0.05).

TABLE 10

Peptide Inhibition of IFNτ Antiproliferative Activity

| Treatment | Experiment 1 Cell Count | Viability | Experiment 2 Cell Count | Viability | Experiment 3 Cell Count | Viability |
|---|---|---|---|---|---|---|
| Medium alone | $9.8 \times 10^5$ | 99% | $13.0 \times 10^5$ | 96% | $27.3 \times 10^5$ | 97% |
| IFNτ | $5.0 \times 10^5$ | 98% | $5.6 \times 10^5$ | 97% | $8.3 \times 10^5$ | 97% |
| IFNτ + IFNτ (1-37) | $6.3 \times 10^5$ | 100% | $10.6 \times 10^5$ | 98% | $13.4 \times 10^5$ | 100% |
| IFNτ + IFNτ (34-64) | $5.3 \times 10^5$ | 96% | $6.9 \times 10^5$ | 95% | $16.0 \times 10^5$ | 98% |
| IFNτ + IFNτ (62-92) | $6.5 \times 10^5$ | 97% | $9.2 \times 10^5$ | 93% | $8.9 \times 10^5$ | 96% |
| IFNτ + IFNτ (90-122) | $5.9 \times 10^5$ | 100% | $11.0 \times 10^5$ | 97% | $19.6 \times 10^5$ | 98% |
| IFNτ + IFNτ (119-150) | $8.4 \times 10^5$ | 100% | $13.2 \times 10^5$ | 96% | $31.8 \times 10^5$ | 90% |
| IFNτ + IFNτ (139-172) | $5.1 \times 10^5$ | 100% | $12.7 \times 10^5$ | 98% | $18.9 \times 10^5$ | 98% |

When proliferation of MDBK cells was monitored over a two-day period, cell number increased roughly 2-fold with greater than 95% viability. Addition of 300 units/ml of OvIFNτ entirely eliminated cell proliferation without a decrease in cell viability. Ovine IFNτ (119-150) was the most effective inhibitor of IFNτ antiproliferative activity.

Antisera to IFNτ (119-150), which inhibited binding of OvIFNτ to receptor, also reversed the OvIFNτ antiproliferative effect. Several other peptides, notably IFNτ (139-172), reversed the OvIFNτ antiproliferative effect, but to a lesser extent.

EXAMPLE 18

Further Analysis of the Cellular and Anti-Viral Effects of IFNτ

A. HIV Anti-Viral Effects.

The antiviral effects of IFNτ against HIV were evaluated by treating human PBMC cells with various amounts of either recombinant ovine IFNτ (r-OvIFNτ) or recombinant human IFNα2a at the time of infection with HIV. IFNτ was present throughout the experiment. At day 7 and day 14, p24 production was determined (by ELISA (Wang, et al., 1988, 1989) and compared to a zero drug control. The results of this analysis are presented in Table 11.

TABLE 11

| Amounts of Drug Units/ml | | % Inhibition | % Inhibition |
|---|---|---|---|
| IFNα2a | IFNτ | Day 7 | Day 14 |
| 10 | | 58%, 48% | 91%, 91% |
| | 26 | 48%, 45% | 88%, 59% |
| 100 | | 68%, 74% | 94%, 91% |
| | 260 | 58%, 51% | 82%, 70% |
| 1,000 | | 89%, 86% | 97%, 93% |
| | 2,600 | 65%, 68% | 87%, 79% |
| 10,000 | | 90%, 86% | 99%, 99% |
| | 26,000 | 77%, 85% | 77%, 96% |
| | 260,000 | 85%, 84% | 96%, 86% |

The data from these experiments support the conclusion that, at relatively low concentrations, IFNα2a and IFNτ are effective in reducing the replication of HIV in human lymphocytes.

B. In vitro Cytotoxicity Test in PBMC's

Human PBMC's were seeded at $5 \times 10^5$ cells/ml. Cells were stimulated at day 0 with 3 μg/ml PHA. Cells were treated with recombinant human IFNα2A (at concentrations of 10, 100, 1,000 and 10,000 units/ml) and IFNτ (at concentrations of 2.6, 26, 260, 2,600, 26,000, 260,000, and 2,600,000 units/ml) in 200 μl/wells (4 replicates of each concentration using 96 well flat bottom plates). Control cultures were given no interferons. After 4 days of incubation, cells were pulsed for 9 hours using $^3$H-thymidine at 1 uCi/well. The cells were harvested and the incorporation of labeled thymidine into DNA was determined (FIG. 8).

No cytotoxicity was observed by measuring the uptake of thymidine at any concentration of IFNτ. However, rHuIFNα2 was toxic to cells at 1,000 units/ml.

In a second experiment, the same human PBMC's were treated with either IFNτ or human IFNα2A at concentrations of 100 units/ml or 10,000 units/ml. After 3 days or 8 days of incubation, viable cells were counted by flow cytometry. The results of this analysis are presented in Table 12.

TABLE 12

| | Number of Viable Cells × 10,000 | |
|---|---|---|
| Treatment (units/ml) | Day 3 | Day 8 |
| No Treatment | 735 | 840 |
| IFNτ 100 units/ml | 745 | 860 |
| IFNτ 10,000 units/ml | 695 | 910 |
| IFNα2a 100 units/ml | 635 | 750 |
| IFNα2a 10,000 units/ml | 680 | 495 |

No cytotoxicity was observed in the cells treated with IFNτ. However, there was 10% cell death in IFNα2a treated cells at Day 3 and 49% cell death at Day 8.

C. Inhibition of Hepatitis B Virus DNA Replication in Hepatocytes

The cell line used, HepG2-T14, is a human cell that was derived from liver cells transfected with Hepatitis B Virus (HBV). The cell line semi-stably produces HBV virus: over time the cell line's production of HBV intracellular DNA and secreted virus decreases. In order to maximize production of HBV DNA and virus, the cells are pre-treated with deAZA-C (5-azacytidine; Miyoshi, et al.) to induce production of the virus. Treatment was for 2–3 days and the amount of induction was about a factor of two.

The cells were then treated with either the IFNα and IFNτ at levels of 0, 5,000, 10,000, 20,000 and 40,000 units per ml.

All levels of either IFNα or IFNτ reduced DNA production by about a factor of 2 compared to the no drug control.

D. Inhibition of Hepatospecific Messenger RNA Production in Hepatocytes

The hepatocyte cell line HepG2-T14 (described above) was examined for the effects of IFNα and IFNτ on hepatospecific mRNA production. Cells were incubated in concentrations of IFNα or IFNτ at 0, 5,000, 10,000, 20,000, and 40,000 units per ml. The messenger RNAs for the hepatocyte specific proteins Apo E and Apo A1 were detected by hybridization analysis (Sambrook, et al.; Maniatis, et al.) using probes specific for these two mRNA's (Shoulders, et al., and Wallis, et al.).

No reduction of mRNA production was seen for Apo E or Apo A1 mRNA production with up to 40,000 units of either IFNα or IFNτ. This result suggests that the reduction of viral DNA replication in previous experiments was not due to the effects of IFNs on cellular house-keeping activities; rather the reduction was likely due to specific inhibition of viral replication in the host cells.

E. In Vitro Toxicity of IFNβ, IFNγ and IFNτ—L929 Cell Assay

The toxicity of IFN treatment was measured in vitro using the mouse L929 cell line. L929 cells were treated with 6000 U/ml to 200,000 U/ml of either OvIFNτ or MuIFNβ. The interferons were added at time zero and the cells were incubated for 72 hours and stained with crystal violet. The percentage of living cells was determined by measuring the absorbance at 405 nm.

Figure 21:
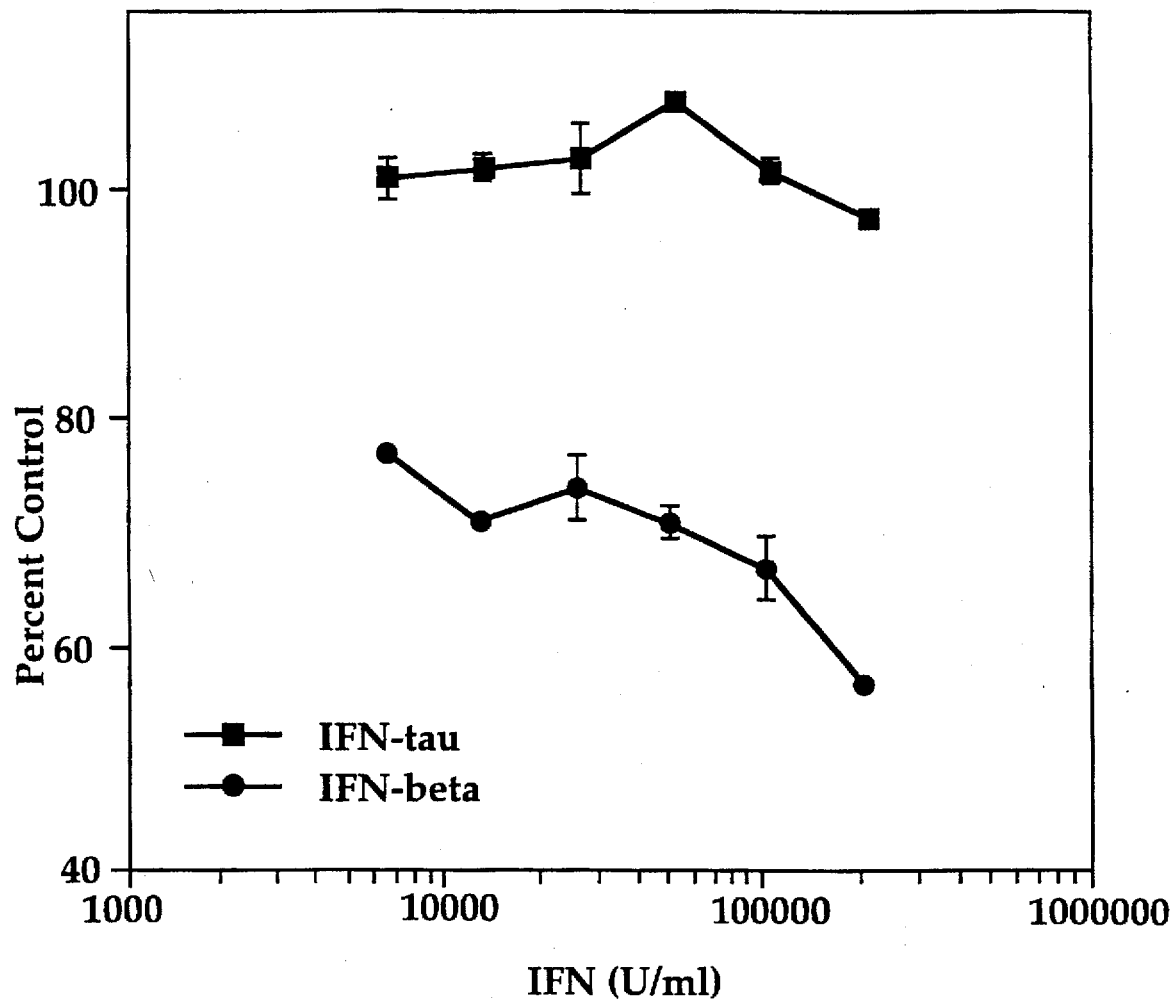
FIG. 21 presents data comparing the cytotoxicity of IFNτ with IFNβ.

Exemplary data are shown in FIG. 21. Values are presented as percent viability±standard error in which 100 percent is equal to the viability of L929 cells treated with media alone. At 6000 U/ml, IFNβ-treated cells exhibited a 77.0±0.6% viability. Viability of L929 cells decreased as the concentrations of IFNβ increased in a dose-dependent manner. In contrast, L929 cells showed no decrease in viability at any of the IFNτ concentrations tested. These data indicate that, unlike IFNβ, IFNτ lacks toxicity at high concentrations in vitro.

Taken together, the results summarized above demonstrate that IFNτ is essentially non-toxic at concentrations at which IFNτ induces toxicity both in vitro and in vivo.

F. In Vivo Toxicity of IFNβ, IFNγ and IFNτ—Cell Counts and Weight Changes

The effects of in vivo treatment with IFNτ, IFNβ and IFNα ($10^5$ U/injection) on total white blood cell (WBC), total lymphocyte counts and weight measurements in NZW mice were assessed as follows. Interferons (OvIFNτ, MuIFNβ, and MuIFNα) were injected intraperitoneally (i.p.) at a concentration of $10^5$ U in a total volume of 0.2 ml in PBS into groups of New Zealand White (NZW) mice (Jackson Laboratories, Bar Harbor, Me.). Three to four animals were included in each group. White blood cell (WBC) counts were determined before injection and at selected timepoints thereafter (typically 12 and 24 hours) using a hemocytometer and standard techniques. Differential WBC counts were performed on Wright-Giemsa stained blood smears. The Before injection, the weights of the animals ranged from 20 to 23 grams.

The results are summarized in Table 13, below.

TABLE 13

IN VIVO TOXICITY OF INTERFERONS AS MEASURED BY WHITE BLOOD CELL COUNTS AND PERCENT WEIGHT CHANGE

| | Cell Count (Cell No. × $10^3$) | | | | % Lymphocyte Depression | % Weight Change 24 Hours after Injection |
|---|---|---|---|---|---|---|
| | Before Injection | | 12 hr. after Injection | | | |
| IFN | Total WBC | Lymphocytes | Total WBC | Lymphocytes | | |
| none | 7.3 ± 1.0 | 6.4 ± 0.7 | 8.0 ± 0.8 | 7.1 ± 0.7 | 0 | +0.5 ± 0.7 |
| τ | 6.7 ± 0.7 | 5.9 ± 0.6 | 6.7 ± 0.5 | 5.8 ± 0.4 | 1.7 | +1.3 ± 0.5 |
| β | 7.0 ± 1.4 | 6.0 ± 0.5 | 6.8 ± 0.8 | 4.1 ± 0.3 | 31.7 | −20.0 ± 1.0 |
| α | 6.0 ± 0.8 | 5.2 ± 0.7 | 4.8 ± 0.5 | 2.3 ± 0.2 | 55.8 | −8.5 ± 2.0 |

No significant differences in WBC counts, lymphocyte counts or weight change were observed between IFNτ-treated and untreated mice. In contrast, IFNβ-treated mice exhibited a 31.7% depression in lymphocyte counts 12 hours after injection, which continued for at least the next 12 hours. IFNα-treated mice exhibited a 55.8% lymphocyte depression and significant weight loss 12 hours after injection. These data indicate that, unlike IFNβ and IFNα, IFNτ lacks toxicity in vivo at the above concentrations as evidenced by peripheral blood cell counts and weight measurements.

EXAMPLE 19

Isolation of Interferon-τ Fusion Protein

Sepharose 4B beads conjugated with anti-beta galactosidase is purchased from Promega. The beads are packed in 2 ml column and washed successively with phosphate-buffered saline with 0.02% sodium azide and 10 ml TX buffer (10 mM Tris buffer, pH 7.4, 1% aprotinin).

The IFNτ coding sequence (e.g., SEQ ID NO:33, i.e., minus the nucleotides corresponding to the leader sequence) is cloned into the polylinker site of lambda gt11. The IFNτ coding sequence is placed in-frame with the amino terminal β-galactosidase coding sequences in lambda gt11. Lysogens infected with gt11/IFNτ are used to inoculate 500 ml of NZYDT broth. The culture is incubated at 32° C. with aeration to an O.D. of about 0.2 to 0.4, then brought to 43° C. quickly in a 43° C. water bath for 15 minutes to induce gt11 peptide synthesis, and incubated further at 37° C. for 1 hour. The cells are pelleted by centrifugation, suspended in 10 ml of lysis buffer (10 mM Tris, pH 7.4 containing 2% "TRITON X-100" and 1% aprotinin added just before use.

The resuspended cells are frozen in liquid nitrogen then thawed, resulting in substantially complete cell lysis. The lysate is treated with DNaseI to digest bacterial and phage DNA, as evidenced by a gradual loss of viscosity in the lysate. Non-solubilized material is removed by centrifugation.

The clarified lysate material is loaded on the Sepharose column, the ends of the column closed, and the column placed on a rotary shaker for 2 hrs. at room temperature and 16 hours at 4° C. After the column settles, it is washed with 10 ml of TX buffer. The fused protein is eluted with 0.1M carbonate/bicarbonate buffer, pH10. Typically, 14 ml of the elution buffer is passed through the column, and the fusion protein is eluted in the first 4–6 ml of eluate.

The eluate containing the fusion protein is concentrated in "CENTRICON-30" cartridges (Amicon, Danvers, Mass.). The final protein concentrate is resuspended in, for example, 400 µl PBS buffer. Protein purity is analyzed by SDS-PAGE.

For polyclonal antibodies, the purified fused protein is injected subcutaneously in Freund's adjuvant in a rabbit. Approximately 1 mg of fused protein is injected at days 0 and 21, and rabbit serum is typically collected at 6 and 8 weeks.

EXAMPLE 20

Preparation of Anti-IFNτ Antibody

A. Expression of Glutathione-S-Transferase Fusion Proteins.

The IFNτ coding sequence (e.g., SEQ ID NO:33) is cloned into the pGEX vector (Boyer, et al.; Frangioni, et al.; Guan, et al.; Hakes, et al.; Smith, et al., 1988). The pGEX vector (Smith, et al.) was modified by insertion of a thrombin cleavage sequence in-frame with the glutathione-S-transferase protein (GST—sj26 coding sequence). This vector is designated pGEXthr. The IFNτ coding sequence is placed in-frame with the sj26-thrombin coding sequences (Guan, et al.; Hakes, et al.). The IFNτ coding sequence insert can be generated by the polymerase chain reaction using PCR primers specific for the insert.

The IFNτ fragment is ligated to the linearized pGEXthr vector. The ligation mixture is transformed into E. coli and ampicillin resistant colonies are selected. Plasmids are isolated from the ampicillin resistant colonies and analyzed by restriction enzyme digestion to identify clones containing the IFNτ insert (vector designated pGEXthr-IFNτ).

E. coli strain XL-I Blue is transformed with pGEXthr-IFNτ and is grown at 37° C. overnight. DNA is prepared from randomly-picked colonies. The presence of the insert coding sequence is typically confirmed by (i) restriction digest mapping, (ii) hybridization screening using labelled IFNτ probes (i.e., Southern analysis), or (iii) direct DNA sequence analysis.

B. Partial Purification of Fusion Proteins.

A pGEXthr-IFNτ clone is grown overnight. The overnight culture is diluted 1:10 with LB medium containing ampicillin and grown for one hour at 37° C. Alternatively, the overnight culture is diluted 1:100 and grown to OD of 0.5–1.0 before addition of IPTG (isopropylthio-β-galactoside). IPTG (GIBCO-BRL, Gaithersburg Md.) is added to a final concentration of 0.2–0.5 mM for the induction of protein expression and the incubation is typically continued for 2–5 hours, preferably 3.5 hours.

Bacterial cells are harvested by centrifugation and resuspended in 1/100 culture volume of MTPBS (150 mM NaCl, 16 mM $Na_2HPO_4$, 4 mM $NaH_2PO_4$). Cells are lysed by lysozyme, sonication or French press, and lysates cleared of cellular debris by centrifugation.

An aliquot of the supernatant obtained from IPTG-induced cultures of pGEXthr-IFNτ-containing cells and an aliquot of the supernatant obtained from IPTG-induced cultures of pGEXthr-vector alone are analyzed by SDS-polyacrylamide gel electrophoresis followed by Western blotting, as described below.

If necessary, the extracts can be concentrated by ultrafiltration using, for example, a "CENTRICON 10" filter.

Alternatively, the fusion proteins are partially purified over a glutathione agarose affinity column as described in detail by Smith, et al. In this method, 100 ml cultures are grown overnight. The cultures are diluted to 1 liter, and the cells grown another hour at 37° C. Expression of the fusion proteins is induced using IPTG. The induced cultures are grown at 37° C. for 3.5 hours. Cells are harvested and a sonicator used to lyse the cells. Cellular debris is pelleted and the clear lysate loaded onto a glutathione "SEPHAROSE" column. The column is washed with several column volumes. The fusion protein is eluted from the affinity column with reduced glutathione and dialyzed. The IFNτ can be liberated from the hybrid protein by treatment with thrombin. The sj26 and IFNτ fragments of the hybrid protein can then be separated by size fractionation over columns or on gels.

Alternatively, the IFNτ portion of the hybrid protein is released from the column by treatment with thrombin (Guan, et al.; Hakes, et al.).

C. Antibodies Against the Fusion Protein.

The purified Sj26/IFNτ fused protein is injected subcutaneously in Freund's adjuvant in a rabbit. Approximately 1 mg of fused protein is injected at days 0 and 21, and rabbit serum is typically collected at 6 and 8 weeks. A second rabbit is similarly immunized with purified Sj26 protein obtained from control bacterial lysate.

Minilysates from the following bacterial cultures are prepared: (1) KM392 cells infected with pGEXthr and pGEXthr containing the IFNτ insert; and (2) cells infected with lambda gt11 containing the IFNτ insert. The minilysates and a commercial source β-galactosidase are fractionated by SDS-PAGE, and the bands transferred to nitrocellulose filters for Western blotting (Sambrook, et al.; Ausubel, et al.).

Summarizing the expected results, serum from control (Sj26) rabbits is immunoreactive with each of the Sj26 and Sj26 fused protein antigens. Serum from the animal immunized with Sj26/IFNτ fused protein is reactive with all Sj-26 and beta-gal fusion proteins containing IFNτ coding sequences, indicating the presence of specific immunoreaction with the IFNτ antigen. None of the sera are expected to be immunoreactive with beta-galactosidase.

Anti-IFNτ antibody present in the sera from the animal immunized with the Sj26/IFNτ is purified by affinity chromatography (using immobilized recombinantly produced IFNτ as ligand, essentially as described above in Example 12 for the anti-beta-galactosidase antibody).

It is claimed:

1. An isolated human interferon-τ protein comprising an amino acid sequence encoded by a nucleic acid molecule present in a human DNA library, wherein the coding sequence of said nucleic acid molecule exhibits at least 95% identity to the coding sequence set forth in SEO ID NO: 43, 29, 33, 25, 27, 21, or 23.

2. A protein of claim 1, where said protein is recombinantly produced.

3. A method of inhibiting the growth of tumor cells, comprising the step of contacting the tumor cells with a human interferon-τ protein according to claim 1 at a concentration effective to inhibit their growth.

4. A method according to claim 3, wherein the tumor cells are human carcinoma cells, human leukemia cells, human T-lymphoma cells, or human melanoma cells.

5. A methods according to claim 4, wherein the tumor cells are steroid-sensitive.

6. A method according to claim 5, wherein the tumor cells are mammary tumor cells.

7. A method of inhibiting the replication of a virus within cells infected by the virus, comprising the step of contacting the infected cells with a human interferon-τ protein according to claim 1 at a concentration effective to inhibit the replication of the virus within the cells.

8. A method according to claim 7, wherein the virus is an RNA virus.

9. A method according to claim 8, wherein the virus is a human immunodeficiency virus or hepatitis C virus.

10. A method according to claim 7, wherein the virus is a DNA virus.

11. A method according to claim 10, wherein the virus is hepatitis B virus.

12. An isolated interferon-τ protein comprising the amino acid sequence presented as SEQ ID NO: 44.

13. An isolated interferon-τ protein comprising the amino acid sequence presented as SEQ ID NO: 30, wherein Xaa represents any amine acid.

14. An isolated interferon-τ protein comprising the amino acid sequence presented as SEQ ID NO: 34.

15. An isolated interferon-τ protein comprising the amino acid sequence presented as SEQ ID NO: 26.

16. An isolated interferon-τ protein comprising the amino acid sequence presented as SEQ ID NO: 28.

17. An isolated interferon-τ protein comprising the amino acid sequence presented as SEQ ID NO: 22.

18. An solated interferon-τ proten comprising the amino acid sequence presented as SEQ ID NO: 24.

\* \* \* \* \*

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
    ( A ) LENGTH: 516 base pairs
    ( B ) TYPE: nucleic acid
    ( C ) STRANDEDNESS: double
    ( D ) TOPOLOGY: circular ( i i ) MOLECULE TYPE: DNA ( i i i ) HYPOTHETICAL: NO ( i v ) ANTI-SENSE: NO ( v i ) ORIGINAL SOURCE:
    ( A ) ORGANISM: Ovis aries
    ( B ) STRAIN: Domestic
    ( D ) DEVELOPMENTAL STAGE: Blastula (blastocyst)
    ( F ) TISSUE TYPE: Trophectoderm
    ( G ) CELL TYPE: Mononuclear trophectoderm cells ( v i i ) IMMEDIATE SOURCE:
    ( B ) CLONE: oTP-1a ( v i i i ) POSITION IN GENOME:
    ( C ) UNITS: bp ( i x ) FEATURE:
    ( A ) NAME/KEY: CDS
    ( B ) LOCATION: 1..516

( x ) PUBLICATION INFORMATION:
    ( A ) AUTHORS: Ott, Troy L
         Van Heeke, Gino
         Johnson, Howard M
         Bazer, Fuller W
    ( B ) TITLE: Cloning and Expression in Saccharomyces
         cerevisiae of a Synthetic Gene for the Type I
         Trophoblast Interferon Ovine Trophoblast
         Protein- 1:Purification and Antiviral Activity
    ( C ) JOURNAL: J. Interferon Res.
    ( D ) VOLUME: 11
    ( F ) PAGES: 357-364
    ( G ) DATE: 1991
    ( K ) RELEVANT RESIDUES IN SEQ ID NO:1: FROM 1 TO 516

( x i ) SEQUENCE DESCRIPTION: SEQ ID NO:1:

```
TGC  TAC  CTG  TGG  CGA  AAA  CTG  ATG  CTG  GAC  GCT  CGA  GAA  AAT  TTA  AAA      48
Cys  Tyr  Leu  Ser  Arg  Lys  Leu  Met  Leu  Asp  Ala  Arg  Glu  Asn  Leu  Lys
  1              5                        10                       15

CTG  CTG  GAC  CGT  ATG  AAT  CGA  TTG  TCT  CCG  CAC  AGC  TGC  CTG  CAA  GAC      96
Leu  Leu  Asp  Arg  Met  Asn  Arg  Leu  Ser  Pro  His  Ser  Cys  Leu  Gln  Asp
                 20                        25                       30

CGG  AAA  GAC  TTC  GGT  CTG  CCG  CAG  GAA  ATG  GTT  GAA  GGT  GAC  CAA  CTG     144
Arg  Lys  Asp  Phe  Gly  Leu  Pro  Gln  Glu  Met  Val  Glu  Gly  Asp  Gln  Leu
            35                        40                       45

CAA  AAA  GAC  CAA  GCT  TTC  CCG  GTA  CTG  TAT  GAA  ATG  CTG  CAG  CAG  TCT     192
Gln  Lys  Asp  Gln  Ala  Phe  Pro  Val  Leu  Tyr  Glu  Met  Leu  Gln  Gln  Ser
       50                        55                       60

TTC  AAC  CTG  TTC  TAC  ACT  GAA  CAT  TCT  TCG  GCC  GCT  TGG  GAC  ACT  ACT     240
Phe  Asn  Leu  Phe  Tyr  Thr  Glu  His  Ser  Ser  Ala  Ala  Trp  Asp  Thr  Thr
 65                        70                       75                       80

CTT  CTA  GAA  CAA  CTG  TGC  ACT  GGT  CTG  CAA  CAG  CAA  CTG  GAC  CAT  CTG     288
```

```
Leu Leu Glu Gln Leu Cys Thr Gly Leu Gln Gln Gln Leu Asp His Leu
             85                  90                  95

GAC ACT TGC CGT GGC CAG GTT ATG GGT GAA GAA GAC TCT GAA CTG GGT      336
Asp Thr Cys Arg Gly Gln Val Met Gly Glu Glu Asp Ser Glu Leu Gly
            100                 105                 110

AAC ATG GAT CCG ATC GTT ACT GTT AAA AAA TAT TTC CAG GGT ATC TAC      384
Asn Met Asp Pro Ile Val Thr Val Lys Lys Tyr Phe Gln Gly Ile Tyr
        115                 120                 125

GAC TAC CTG CAG GAA AAA GGT TAC TCT GAC TGC GCT TGG GAA ATC GTA      432
Asp Tyr Leu Gln Glu Lys Gly Tyr Ser Asp Cys Ala Trp Glu Ile Val
    130                 135                 140

CGC GTT GAA ATG ATG CGG GCC CTG ACT GTG TCG ACT ACT CTG CAA AAA      480
Arg Val Glu Met Met Arg Ala Leu Thr Val Ser Thr Thr Leu Gln Lys
145                 150                 155                 160

CGG TTA ACT AAA ATG GGT GGT GAC CTG AAT TCT CCG                      516
Arg Leu Thr Lys Met Gly Gly Asp Leu Asn Ser Pro
                165                 170
```

( 2 ) INFORMATION FOR SEQ ID NO:2:

( i ) SEQUENCE CHARACTERISTICS:
        ( A ) LENGTH: 172 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: amino acid sequence of a mature
            OvIFNtau protein ( x i ) SEQUENCE DESCRIPTION: SEQ ID NO:2:

```
Cys Tyr Leu Ser Arg Lys Leu Met Leu Asp Ala Arg Glu Asn Leu Lys
 1               5                  10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Pro Val Leu Tyr Glu Met Leu Gln Gln Ser
    50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Gln Leu Asp His Leu
             85                  90                  95

Asp Thr Cys Arg Gly Gln Val Met Gly Glu Glu Asp Ser Glu Leu Gly
            100                 105                 110

Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
    130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

( 2 ) INFORMATION FOR SEQ ID NO:3:

( i ) SEQUENCE CHARACTERISTICS:
        ( A ) LENGTH: 516 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
   ( C ) INDIVIDUAL ISOLATE: synthetic nucleotide sequence encoding
   a mature human interferon-tau protein, HuIFNtau1.

( x i ) SEQUENCE DESCRIPTION: SEQ ID NO:3:

```
TGTGACTTGT CTCAAAACCA CGTTTTGGTT GGTAGAAAGA ACTTAAGACT ACTAGACGAA      60
ATGAGACGTC TATCTCCACG CTTCTGTCTA CAAGACAGAA AGGACTTCGC TTTGCCTCAG     120
GAAATGGTTG AAGGTGGCCA ACTACAAGAA GCTCAAGCGA TATCTGTTTT GCACGAAATG     180
TTGCAACAAA GCTTCAACTT GTTCCACACC GAACACTCTT CGGCCGCTTG GGACACCACC     240
TTGTTGGAAC AGCTCAGAAC CGGTTTGCAC CAACAATTGG ACAACTTGGA TGCATGTTTG     300
GGTCAAGTTA TGGGTGAAGA AGACTCTGCT CTCGGGAGAA CCGGTCCAAC GCTAGCTTTG     360
AAGAGATACT TCCAAGGTAT CCACGTTTAC TTGAAGGAAA AGGGTTACTC TGACTGTGCT     420
TGGGAAACCG TGCGTCTAGA AATCATGCGT AGCTTCTCTT CTTTGATCAG CTTGCAAGAA     480
AGATTACGTA TGATGGACGG TGACTTGTCG AGCCCA                              516
```

( 2 ) INFORMATION FOR SEQ ID NO:4:

( i ) SEQUENCE CHARACTERISTICS:
      ( A ) LENGTH: 172 amino acids
      ( B ) TYPE: amino acid
      ( C ) STRANDEDNESS: single
      ( D ) TOPOLOGY: linear ( i i ) MOLECULE TYPE: protein ( v i ) ORIGINAL SOURCE:
      ( C ) INDIVIDUAL ISOLATE: amino acid sequence for a mature
      HuIFNtau protein, HuIFNtau1.

( x i ) SEQUENCE DESCRIPTION: SEQ ID NO:4:

```
Cys Asp Leu Ser Gln Asn His Val Leu Val Gly Arg Lys Asn Leu Arg
1               5                   10                  15

Leu Leu Asp Glu Met Arg Arg Leu Ser Pro Arg Phe Cys Leu Gln Asp
                20                  25                  30

Arg Lys Asp Phe Ala Leu Pro Gln Glu Met Val Glu Gly Gly Gln Leu
            35                  40                  45

Gln Glu Ala Gln Ala Ile Ser Val Leu His Glu Met Leu Gln Gln Ser
        50                  55                  60

Phe Asn Leu Phe His Thr Glu His Ser Ser Ala Ala Trp Asp Thr Thr
65                  70                  75                  80

Leu Leu Glu Gln Leu Arg Thr Gly Leu His Gln Gln Leu Asp Asn Leu
                85                  90                  95

Asp Ala Cys Leu Gly Gln Val Met Gly Glu Glu Asp Ser Ala Leu Gly
            100                 105                 110

Arg Thr Gly Pro Thr Leu Ala Leu Lys Arg Tyr Phe Gln Gly Ile His
        115                 120                 125

Val Tyr Leu Lys Glu Lys Gly Tyr Ser Asp Cys Ala Trp Glu Thr Val
    130                 135                 140

Arg Leu Glu Ile Met Arg Ser Phe Ser Ser Leu Ile Ser Leu Gln Glu
145                 150                 155                 160

Arg Leu Arg Met Met Asp Gly Asp Leu Ser Ser Pro
                165                 170
```

( 2 ) INFORMATION FOR SEQ ID NO:5:

( i ) SEQUENCE CHARACTERISTICS:
    ( A ) LENGTH: 37 amino acids
    ( B ) TYPE: amino acid
    ( D ) TOPOLOGY: linear ( i i ) MOLECULE TYPE: protein ( v i ) ORIGINAL SOURCE:
    ( C ) INDIVIDUAL ISOLATE: amino acid sequence of fragment 1-37
        of SEQ ID NO:2

( x i ) SEQUENCE DESCRIPTION: SEQ ID NO:5:

```
Cys Tyr Leu Ser Arg Lys Leu Met Leu Asp Ala Arg Glu Asn Leu Lys
                  5                  10                      15
Leu Leu Asp Arg Met Asn Arg Leu Ser Pro His Ser Cys Leu Gln Asp
             20                  25                  30
Arg Lys Asp Phe Gly
         35
```

( 2 ) INFORMATION FOR SEQ ID NO:6:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: amino acid sequence of fragment 34-64
            of SEQ ID NO:2

( x i ) SEQUENCE DESCRIPTION: SEQ ID NO:6:

```
Lys Asp Phe Gly Leu Pro Gln Glu Met Val Glu Gly Asp Gln Leu Gln
                 5                  10                      15
Lys Asp Gln Ala Phe Pro Val Leu Tyr Glu Met Leu Gln Gln Ser
             20                  25                  30
```

( 2 ) INFORMATION FOR SEQ ID NO:7:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: amino acid sequence of fragment 62-92
            of SEQ ID NO:2

( x i ) SEQUENCE DESCRIPTION: SEQ ID NO:7:

```
Gln Gln Ser Phe Asn Leu Phe Tyr Thr Glu His Ser Ser Ala Ala Trp
                 5                  10                      15
Asp Thr Thr Leu Leu Glu Gln Leu Cys Thr Gly Leu Gln Gln Gln
             20                  25                  30
```

( 2 ) INFORMATION FOR SEQ ID NO:8:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: amino acid sequence of fragment 90-122
            of SEQ ID NO:2

( x i ) SEQUENCE DESCRIPTION: SEQ ID NO:8:

Gln Gln Gln Leu Asp His Leu Asp Thr Cys Arg Gly Gln Val Met Gly
                    5                   10                  15

Glu Glu Asp Ser Glu Leu Gly Asn Met Asp Pro Ile Val Thr Val Lys
                20                  25                  30

Lys ( 2 ) INFORMATION FOR SEQ ID NO:9:

( i ) SEQUENCE CHARACTERISTICS:
      ( A ) LENGTH: 32 amino acids
      ( B ) TYPE: amino acid
      ( D ) TOPOLOGY: linear ( i i ) MOLECULE TYPE: protein ( v i ) ORIGINAL SOURCE:
      ( C ) INDIVIDUAL ISOLATE: amino acid sequence of fragment 119-15
          of SEQ ID NO:2

( x i ) SEQUENCE DESCRIPTION: SEQ ID NO:9:

Thr Val Lys Lys Tyr Phe Gln Gly Ile Tyr Asp Tyr Leu Gln Glu Lys
                5                   10                  15

Gly Tyr Ser Asp Cys Ala Trp Glu Ile Val Arg Val Glu Met Met Arg
                20                  25                  30

( 2 ) INFORMATION FOR SEQ ID NO:10:

( i ) SEQUENCE CHARACTERISTICS:
      ( A ) LENGTH: 34 amino acids
      ( B ) TYPE: amino acid
      ( D ) TOPOLOGY: linear ( i i ) MOLECULE TYPE: protein ( v i ) ORIGINAL SOURCE:
      ( C ) INDIVIDUAL ISOLATE: amino acid sequence of fragment 139-17
          of SEQ ID NO:2

( x i ) SEQUENCE DESCRIPTION: SEQ ID NO:10:

Cys Ala Trp Glu Ile Val Arg Val Glu Met Met Arg Ala Leu Thr Val
                5                   10                  15

Ser Thr Thr Leu Gln Lys Arg Leu Thr Lys Met Gly Gly Asp Leu Asn
                20                  25                  30

Ser Pro ( 2 ) INFORMATION FOR SEQ ID NO:11:

( i ) SEQUENCE CHARACTERISTICS:
      ( A ) LENGTH: 588 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( C ) INDIVIDUAL ISOLATE: HuIFNtau1 Human Interferon Tau coding
          sequence with a leader sequence.

( i x ) FEATURE:
      ( A ) NAME/KEY: CDS
      ( B ) LOCATION: 1..585

( x i ) SEQUENCE DESCRIPTION: SEQ ID NO:11:

```
ATG  GCC  TTC  GTG  CTC  TCT  CTA  CTC  ATG  GCC  CTG  GTG  CTG  GTC  AGC  TAC         48
Met  Ala  Phe  Val  Leu  Ser  Leu  Leu  Met  Ala  Leu  Val  Leu  Val  Ser  Tyr
 1              5                        10                       15

GGC  CCA  GGA  GGA  TCC  CTG  GGT  TGT  GAC  CTG  TCT  CAG  AAC  CAC  GTG  CTG         96
Gly  Pro  Gly  Gly  Ser  Leu  Gly  Cys  Asp  Leu  Ser  Gln  Asn  His  Val  Leu
                20                       25                       30

GTT  GGC  AGG  AAG  AAC  CTC  AGG  CTC  CTG  GAC  GAA  ATG  AGG  AGA  CTC  TCC        144
Val  Gly  Arg  Lys  Asn  Leu  Arg  Leu  Leu  Asp  Glu  Met  Arg  Arg  Leu  Ser
           35                       40                       45

CCT  CGC  TTT  TGT  CTG  CAG  GAC  AGA  AAA  GAC  TTC  GCT  TTA  CCC  CAG  GAA        192
Pro  Arg  Phe  Cys  Leu  Gln  Asp  Arg  Lys  Asp  Phe  Ala  Leu  Pro  Gln  Glu
      50                       55                       60

ATG  GTG  GAG  GGC  GGC  CAG  CTC  CAG  GAG  GCC  CAG  GCC  ATC  TCT  GTG  CTC        240
Met  Val  Glu  Gly  Gly  Gln  Leu  Gln  Glu  Ala  Gln  Ala  Ile  Ser  Val  Leu
 65                       70                       75                       80

CAT  GAG  ATG  CTC  CAG  CAG  AGC  TTC  AAC  CTC  TTC  CAC  ACA  GAG  CAC  TCC        288
His  Glu  Met  Leu  Gln  Gln  Ser  Phe  Asn  Leu  Phe  His  Thr  Glu  His  Ser
                     85                       90                       95

TCT  GCT  GCC  TGG  GAC  ACC  ACC  CTC  CTG  GAG  CAG  CTC  CGC  ACT  GGA  CTC        336
Ser  Ala  Ala  Trp  Asp  Thr  Thr  Leu  Leu  Glu  Gln  Leu  Arg  Thr  Gly  Leu
               100                      105                      110

CAT  CAG  CAG  CTG  GAC  AAC  CTG  GAT  GCC  TGC  CTG  GGG  CAG  GTG  ATG  GGA        384
His  Gln  Gln  Leu  Asp  Asn  Leu  Asp  Ala  Cys  Leu  Gly  Gln  Val  Met  Gly
          115                      120                      125

GAG  GAA  GAC  TCT  GCC  CTG  GGA  AGG  ACG  GGC  CCC  ACC  CTG  GCT  CTG  AAG        432
Glu  Glu  Asp  Ser  Ala  Leu  Gly  Arg  Thr  Gly  Pro  Thr  Leu  Ala  Leu  Lys
     130                      135                      140

AGG  TAC  TTC  CAG  GGC  ATC  CAT  GTC  TAC  CTG  AAA  GAG  AAG  GGA  TAC  AGC        480
Arg  Tyr  Phe  Gln  Gly  Ile  His  Val  Tyr  Leu  Lys  Glu  Lys  Gly  Tyr  Ser
145                      150                      155                      160

GAC  TGC  GCC  TGG  GAA  ACC  GTC  AGA  CTG  GAA  ATC  ATG  AGA  TCC  TTC  TCT        528
Asp  Cys  Ala  Trp  Glu  Thr  Val  Arg  Leu  Glu  Ile  Met  Arg  Ser  Phe  Ser
               165                      170                      175

TCA  TTA  ATC  AGC  TTG  CAA  GAA  AGG  TTA  AGA  ATG  ATG  GAT  GGA  GAC  CTG        576
Ser  Leu  Ile  Ser  Leu  Gln  Glu  Arg  Leu  Arg  Met  Met  Asp  Gly  Asp  Leu
          180                      185                      190

AGC  TCA  CCT  TGA                                                                    588
Ser  Ser  Pro
          195
```

( 2 ) INFORMATION FOR SEQ ID NO:12:

( i ) SEQUENCE CHARACTERISTICS:
        ( A ) LENGTH: 195 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: predicted amino acid coding sequence
            of SEQ ID NO:11 (HuIFNtau1).

( x i ) SEQUENCE DESCRIPTION: SEQ ID NO:12:

```
Met  Ala  Phe  Val  Leu  Ser  Leu  Leu  Met  Ala  Leu  Val  Leu  Val  Ser  Tyr
 1              5                        10                       15

Gly  Pro  Gly  Gly  Ser  Leu  Gly  Cys  Asp  Leu  Ser  Gln  Asn  His  Val  Leu
                20                       25                       30

Val  Gly  Arg  Lys  Asn  Leu  Arg  Leu  Leu  Asp  Glu  Met  Arg  Arg  Leu  Ser
           35                       40                       45

Pro  Arg  Phe  Cys  Leu  Gln  Asp  Arg  Lys  Asp  Phe  Ala  Leu  Pro  Gln  Glu
      50                       55                       60
```

```
Met  Val  Glu  Gly  Gly  Gln  Leu  Gln  Glu  Ala  Gln  Ala  Ile  Ser  Val  Leu
 65             70                  75                            80

His  Glu  Met  Leu  Gln  Gln  Ser  Phe  Asn  Leu  Phe  His  Thr  Glu  His  Ser
               85                       90                       95

Ser  Ala  Ala  Trp  Asp  Thr  Thr  Leu  Leu  Glu  Gln  Leu  Arg  Thr  Gly  Leu
              100                  105                      110

His  Gln  Gln  Leu  Asp  Asn  Leu  Asp  Ala  Cys  Leu  Gly  Gln  Val  Met  Gly
          115                  120                      125

Glu  Glu  Asp  Ser  Ala  Leu  Gly  Arg  Thr  Gly  Pro  Thr  Leu  Ala  Leu  Lys
          130                  135                      140

Arg  Tyr  Phe  Gln  Gly  Ile  His  Val  Tyr  Leu  Lys  Glu  Lys  Gly  Tyr  Ser
145                      150                  155                           160

Asp  Cys  Ala  Trp  Glu  Thr  Val  Arg  Leu  Glu  Ile  Met  Arg  Ser  Phe  Ser
              165                       170                      175

Ser  Leu  Ile  Ser  Leu  Gln  Glu  Arg  Leu  Arg  Met  Met  Asp  Gly  Asp  Leu
              180                  185                      190

Ser  Ser  Pro
          195
```

(2) INFORMATION FOR SEQ ID NO:13:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 25-mer synthetic oligonucleotide (xi) SEQUENCE DESCRIPTION: SEQ ID NO:13:

CCTGTCTGCA GGACAGAAAA GACTT 25

(2) INFORMATION FOR SEQ ID NO:14:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 25-mer synthetic oligonucleotide (xi) SEQUENCE DESCRIPTION: SEQ ID NO:14:

TCTGAATTCT GACGATTTCC CAGGC 25

(2) INFORMATION FOR SEQ ID NO:15:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (C) INDIVIDUAL ISOLATE: Amino acid sequence of fragment
        1-37 of SEQ ID NO:4

( x i ) SEQUENCE DESCRIPTION: SEQ ID NO:15:

Cys Asp Leu Ser Gln Asn His Val Leu Val Gly Arg Lys Asn Leu Arg
1               5                       10                      15

Leu Leu Asp Glu Met Arg Arg Leu Ser Pro Arg Phe Cys Leu Gln Asp
                20                  25                  30

Arg Lys Asp Phe Ala
            35

( 2 ) INFORMATION FOR SEQ ID NO:16:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( C ) INDIVIDUAL ISOLATE: Amino acid sequence of fragment
        34-64 of SEQ ID NO:4

( x i ) SEQUENCE DESCRIPTION: SEQ ID NO:16:

Lys Asp Phe Ala Leu Pro Gln Glu Met Val Glu Gly Gly Gln Leu Gln
1               5                       10                      15

Glu Ala Gln Ala Ile Ser Val Leu His Glu Met Leu Gln Gln Ser
                20                  25                  30

( 2 ) INFORMATION FOR SEQ ID NO:17:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( C ) INDIVIDUAL ISOLATE: Amino acid sequence of fragment
        62-92 of SEQ ID NO:4

( x i ) SEQUENCE DESCRIPTION: SEQ ID NO:17:

Gln Gln Ser Phe Asn Leu Phe His Thr Glu His Ser Ser Ala Ala Trp
1               5                       10                      15

Asp Thr Thr Leu Leu Glu Gln Leu Arg Thr Gly Leu His Gln Gln
                20                  25                  30

( 2 ) INFORMATION FOR SEQ ID NO:18:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( C ) INDIVIDUAL ISOLATE: Amino acid sequence of fragment
        90-122 of SEQ ID NO:4

( x i ) SEQUENCE DESCRIPTION: SEQ ID NO:18:

His Gln Gln Leu Asp Asn Leu Asp Ala Cys Leu Gly Gln Val Met Gly
1               5                       10                      15

```
     Glu  Glu  Asp  Ser  Ala  Leu  Gly  Arg  Thr  Gly  Pro  Thr  Leu  Ala  Leu  Lys
                     20                       25                      30

Arg
```

( 2 ) INFORMATION FOR SEQ ID NO:19:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( C ) INDIVIDUAL ISOLATE: Amino acid sequence of fragment
            119-150 of SEQ ID NO:4

( x i ) SEQUENCE DESCRIPTION: SEQ ID NO:19:

```
     Ala  Leu  Lys  Arg  Tyr  Phe  Gln  Gly  Ile  His  Val  Tyr  Leu  Lys  Glu  Lys
     1              5                         10                      15

Gly  Tyr  Ser  Asp  Cys  Ala  Trp  Glu  Thr  Val  Arg  Leu  Glu  Ile  Met  Arg
                     20                       25                      30
```

( 2 ) INFORMATION FOR SEQ ID NO:20:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( C ) INDIVIDUAL ISOLATE: Amino acid sequence of fragment
            139-172 of SEQ ID NO:4

( x i ) SEQUENCE DESCRIPTION: SEQ ID NO:20:

```
     Cys  Ala  Trp  Glu  Thr  Val  Arg  Leu  Glu  Ile  Met  Arg  Ser  Phe  Ser  Ser
     1              5                         10                      15

Leu  Ile  Ser  Leu  Gln  Glu  Arg  Leu  Arg  Met  Met  Asp  Gly  Asp  Leu  Ser
                     20                       25                      30

Ser  Pro
```

( 2 ) INFORMATION FOR SEQ ID NO:21:

( i ) SEQUENCE CHARACTERISTICS:
        ( A ) LENGTH: 299 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: HuIFNtau6

( i x ) FEATURE:
        ( A ) NAME/KEY: CDS
        ( B ) LOCATION: 2..298

( x i ) SEQUENCE DESCRIPTION: SEQ ID NO:21:

```
C  CAG  GAG  ATG  GTG  GAG  GGC  GGC  CAG  CTC  CAG  GAG  GCC  CAG  GCC  ATC        46
```

```
    Gln Glu Met Val Glu Gly Gly Gln Leu Gln Glu Ala Gln Ala Ile
     1           5                   10                  15

TCT GTG CTC CAC AAG ATG CTC CAG CAG AGC TTC AAC CTC TTC CAC ACA         94
Ser Val Leu His Lys Met Leu Gln Gln Ser Phe Asn Leu Phe His Thr
             20                  25                  30

GAG CGC TCC TCT GCT GCC TGG GAC ACC ACC CTC CTG GAG CAG CTC CGC        142
Glu Arg Ser Ser Ala Ala Trp Asp Thr Thr Leu Leu Glu Gln Leu Arg
         35                  40                  45

ACT GGA CTC CAT CAG CAG CTG GAT GAC CTG GAC GCC TGC CTG GGG CAG        190
Thr Gly Leu His Gln Gln Leu Asp Asp Leu Asp Ala Cys Leu Gly Gln
             50                  55                  60

GTG ACG GGA GAG GAA GAC TCT GCC CTG GGA AGG ACG GGC CCC ACC CTG        238
Val Thr Gly Glu Glu Asp Ser Ala Leu Gly Arg Thr Gly Pro Thr Leu
         65                  70                  75

GCC GTG AAG AGC TAC TTC CAG GGC ATC CAT ATC TAC CTG CAA GAG AAG        286
Ala Val Lys Ser Tyr Phe Gln Gly Ile His Ile Tyr Leu Gln Glu Lys
 80                  85                  90                  95

GGA TAC AGC GAC T                                                      299
Gly Tyr Ser Asp
```

( 2 ) INFORMATION FOR SEQ ID NO:22:

( i ) SEQUENCE CHARACTERISTICS:
        ( A ) LENGTH: 99 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: predicted amino acid coding sequence
           of SEQ ID NO:21 (HuIFNtau6).

( x i ) SEQUENCE DESCRIPTION: SEQ ID NO:22:

```
Gln Glu Met Val Glu Gly Gly Gln Leu Gln Glu Ala Gln Ala Ile Ser
 1           5                  10                  15

Val Leu His Lys Met Leu Gln Gln Ser Phe Asn Leu Phe His Thr Glu
             20                  25                  30

Arg Ser Ser Ala Ala Trp Asp Thr Thr Leu Leu Glu Gln Leu Arg Thr
         35                  40                  45

Gly Leu His Gln Gln Leu Asp Asp Leu Asp Ala Cys Leu Gly Gln Val
     50                  55                  60

Thr Gly Glu Glu Asp Ser Ala Leu Gly Arg Thr Gly Pro Thr Leu Ala
 65                  70                  75                  80

Val Lys Ser Tyr Phe Gln Gly Ile His Ile Tyr Leu Gln Glu Lys Gly
             85                  90                  95

Tyr Ser Asp
```

( 2 ) INFORMATION FOR SEQ ID NO:23:

( i ) SEQUENCE CHARACTERISTICS:
        ( A ) LENGTH: 288 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: HuIFNtau7

5,738,845

-continued (ix) FEATURE:
    (A) NAME/KEY: CDS
    (B) LOCATION: 2..286

(xi) SEQUENCE DESCRIPTION: SEQ ID NO:23:

```
C CAG GAG ATG GTG GAG GTC AGC CAG TTC CAG GAG GCC CAG GCC ATT      46
  Gln Glu Met Val Glu Val Ser Gln Phe Gln Glu Ala Gln Ala Ile
  1               5                   10                  15

TCT GTG CTC CAT GAG ATG CTC CAG CAG AGC TTC AAC CTC TTC CAC AAA    94
Ser Val Leu His Glu Met Leu Gln Gln Ser Phe Asn Leu Phe His Lys
                20                  25                  30

GAG CGC TCC TCT GCT GCC TGG GAC ACT ACC CTC CTG GAG CAG CTC CTC   142
Glu Arg Ser Ser Ala Ala Trp Asp Thr Thr Leu Leu Glu Gln Leu Leu
            35                  40                  45

ACT GGA CTC CAT CAG CAG CTG GAT GAC CTG GAT GCC TGT CTG GGG CAG   190
Thr Gly Leu His Gln Gln Leu Asp Asp Leu Asp Ala Cys Leu Gly Gln
        50                  55                  60

TTG ACT GGA GAG GAA GAC TCT GCC CTG GGA AGG ACG GGC CCC ACC CTG   238
Leu Thr Gly Glu Glu Asp Ser Ala Leu Gly Arg Thr Gly Pro Thr Leu
    65                  70                  75

GCC GTG AAG AGC TAC TTC CAG GGC ATC CAT GTC TAC CTG CAA GAG AAG   286
Ala Val Lys Ser Tyr Phe Gln Gly Ile His Val Tyr Leu Gln Glu Lys
80                  85                  90                  95

GG                                                                288
```

(2) INFORMATION FOR SEQ ID NO:24:

(i) SEQUENCE CHARACTERISTICS:
        (A) LENGTH: 95 amino acids
        (B) TYPE: amino acid
        (D) TOPOLOGY: linear (ii) MOLECULE TYPE: protein (vi) ORIGINAL SOURCE:
        (C) INDIVIDUAL ISOLATE: predicted amino acid coding sequence
            of SEQ ID NO:23 (HuIFNtau7).

(xi) SEQUENCE DESCRIPTION: SEQ ID NO:24:

```
Gln Glu Met Val Glu Val Ser Gln Phe Gln Glu Ala Gln Ala Ile Ser
1               5                   10                  15

Val Leu His Glu Met Leu Gln Gln Ser Phe Asn Leu Phe His Lys Glu
                20                  25                  30

Arg Ser Ser Ala Ala Trp Asp Thr Thr Leu Leu Glu Gln Leu Leu Thr
            35                  40                  45

Gly Leu His Gln Gln Leu Asp Asp Leu Asp Ala Cys Leu Gly Gln Leu
        50                  55                  60

Thr Gly Glu Glu Asp Ser Ala Leu Gly Arg Thr Gly Pro Thr Leu Ala
65                  70                  75                  80

Val Lys Ser Tyr Phe Gln Gly Ile His Val Tyr Leu Gln Glu Lys
                85                  90                  95
```

(2) INFORMATION FOR SEQ ID NO:25:

(i) SEQUENCE CHARACTERISTICS:
        (A) LENGTH: 307 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
   (C) INDIVIDUAL ISOLATE: HuIFNtau4

(ix) FEATURE:
   (A) NAME/KEY: CDS
   (B) LOCATION: 2..307

(xi) SEQUENCE DESCRIPTION: SEQ ID NO:25:

| | | | | | | | | | | | | | | | | |
|---|---|---|---|---|---|---|---|---|---|---|---|---|---|---|---|---|
| C | CAG | GAG | ATG | GTG | GAG | GGT | GGC | CAG | CTC | CAG | GAG | GCC | CAG | GCC | ATC | 46 |
| | Gln | Glu | Met | Val | Glu | Gly | Gly | Gln | Leu | Gln | Glu | Ala | Gln | Ala | Ile | |
| | 1 | | | 5 | | | | | 10 | | | | | 15 | | |

| TCT | GTG | CTC | CAC | GAG | ATG | CTC | CAG | CAG | AGC | TTC | AAC | CTC | TTC | CAC | ACA | 94 |
|---|---|---|---|---|---|---|---|---|---|---|---|---|---|---|---|---|
| Ser | Val | Leu | His | Glu | Met | Leu | Gln | Gln | Ser | Phe | Asn | Leu | Phe | His | Thr | |
| | | | | 20 | | | | 25 | | | | | 30 | | | |

| GAG | CAC | TCC | TCT | GCT | GCC | TGG | GAC | ACC | ACC | CTC | CTG | GAG | CAG | CTC | CGC | 142 |
|---|---|---|---|---|---|---|---|---|---|---|---|---|---|---|---|---|
| Glu | His | Ser | Ser | Ala | Ala | Trp | Asp | Thr | Thr | Leu | Leu | Glu | Gln | Leu | Arg | |
| | | | 35 | | | | | 40 | | | | | 45 | | | |

| ACT | GGA | CTC | CAT | CAG | CAG | CTG | GAT | GAC | CTG | GAT | GCC | TGC | CTG | GGG | CAG | 190 |
|---|---|---|---|---|---|---|---|---|---|---|---|---|---|---|---|---|
| Thr | Gly | Leu | His | Gln | Gln | Leu | Asp | Asp | Leu | Asp | Ala | Cys | Leu | Gly | Gln | |
| | | 50 | | | | | 55 | | | | | 60 | | | | |

| GTG | ACG | GGA | GAG | GAA | GAC | TCT | GCC | CTG | GGA | AGG | ACG | GGC | CCC | ACC | CTG | 238 |
|---|---|---|---|---|---|---|---|---|---|---|---|---|---|---|---|---|
| Val | Thr | Gly | Glu | Glu | Asp | Ser | Ala | Leu | Gly | Arg | Thr | Gly | Pro | Thr | Leu | |
| | 65 | | | | | 70 | | | | | 75 | | | | | |

| GCC | ATG | AAG | ACG | TAT | TTC | CAG | GGC | ATC | CAT | GTC | TAC | CTG | AAA | GAG | AAG | 286 |
|---|---|---|---|---|---|---|---|---|---|---|---|---|---|---|---|---|
| Ala | Met | Lys | Thr | Tyr | Phe | Gln | Gly | Ile | His | Val | Tyr | Leu | Lys | Glu | Lys | |
| 80 | | | | | 85 | | | | | 90 | | | | | 95 | |

| GGA | TAT | AGT | GAC | TGC | GCC | TGG | | | | | | | | | | 307 |
|---|---|---|---|---|---|---|---|---|---|---|---|---|---|---|---|---|
| Gly | Tyr | Ser | Asp | Cys | Ala | Trp | | | | | | | | | | |
| | | | | 100 | | | | | | | | | | | | |

(2) INFORMATION FOR SEQ ID NO:26:

(i) SEQUENCE CHARACTERISTICS:
      (A) LENGTH: 102 amino acids
      (B) TYPE: amino acid
      (D) TOPOLOGY: linear (ii) MOLECULE TYPE: protein (vi) ORIGINAL SOURCE:
      (C) INDIVIDUAL ISOLATE: predicted amino acid coding sequence
          of SEQ ID NO:25 (HuIFNtau4).

(xi) SEQUENCE DESCRIPTION: SEQ ID NO:26:

| Gln | Glu | Met | Val | Glu | Gly | Gly | Gln | Leu | Gln | Glu | Ala | Gln | Ala | Ile | Ser |
|---|---|---|---|---|---|---|---|---|---|---|---|---|---|---|---|
| 1 | | | | 5 | | | | | 10 | | | | | 15 | |

| Val | Leu | His | Glu | Met | Leu | Gln | Gln | Ser | Phe | Asn | Leu | Phe | His | Thr | Glu |
|---|---|---|---|---|---|---|---|---|---|---|---|---|---|---|---|
| | | | 20 | | | | 25 | | | | | 30 | | | |

| His | Ser | Ser | Ala | Ala | Trp | Asp | Thr | Thr | Leu | Leu | Glu | Gln | Leu | Arg | Thr |
|---|---|---|---|---|---|---|---|---|---|---|---|---|---|---|---|
| | | 35 | | | | | 40 | | | | | 45 | | | |

| Gly | Leu | His | Gln | Gln | Leu | Asp | Asp | Leu | Asp | Ala | Cys | Leu | Gly | Gln | Val |
|---|---|---|---|---|---|---|---|---|---|---|---|---|---|---|---|
| | 50 | | | | | 55 | | | | | 60 | | | | |

| Thr | Gly | Glu | Glu | Asp | Ser | Ala | Leu | Gly | Arg | Thr | Gly | Pro | Thr | Leu | Ala |
|---|---|---|---|---|---|---|---|---|---|---|---|---|---|---|---|
| 65 | | | | | 70 | | | | | 75 | | | | | 80 |

| Met | Lys | Thr | Tyr | Phe | Gln | Gly | Ile | His | Val | Tyr | Leu | Lys | Glu | Lys | Gly |
|---|---|---|---|---|---|---|---|---|---|---|---|---|---|---|---|
| | | | | 85 | | | | | 90 | | | | | 95 | |

| Tyr | Ser | Asp | Cys | Ala | Trp |
|---|---|---|---|---|---|
| | | | 100 | | |

(2) INFORMATION FOR SEQ ID NO:27:

(i) SEQUENCE CHARACTERISTICS:
      (A) LENGTH: 294 base pairs ( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( C ) INDIVIDUAL ISOLATE: HuIFNtau5

( i x ) FEATURE:
( A ) NAME/KEY: CDS
( B ) LOCATION: 2..292

( x i ) SEQUENCE DESCRIPTION: SEQ ID NO:27:

| C | CAG | GAG | ATG | GTG | GAG | GGT | GGC | CAG | CTC | CAG | GAG | GCC | CAG | GCC | ATC | 46 |
|---|---|---|---|---|---|---|---|---|---|---|---|---|---|---|---|---|
|   | Gln | Glu | Met | Val | Glu | Gly | Gly | Gln | Leu | Gln | Glu | Ala | Gln | Ala | Ile |   |
|   | 1   |     |     |     | 5   |     |     |     |     | 10  |     |     |     |     | 15  |   |

| TCT | GTG | CTC | CAC | GAG | ATG | CTC | CAG | CAG | AGC | TTC | AAC | CTC | TTC | CAC | ACA | 94 |
|---|---|---|---|---|---|---|---|---|---|---|---|---|---|---|---|---|
| Ser | Val | Leu | His | Glu | Met | Leu | Gln | Gln | Ser | Phe | Asn | Leu | Phe | His | Thr |   |
|     |     |     |     | 20  |     |     |     |     | 25  |     |     |     |     | 30  |     |   |

| GAG | CAC | TCC | TCT | GCT | GCC | TGG | GAC | ACC | ACC | CTC | CTG | GAG | CAG | CTC | CGC | 142 |
|---|---|---|---|---|---|---|---|---|---|---|---|---|---|---|---|---|
| Glu | His | Ser | Ser | Ala | Ala | Trp | Asp | Thr | Thr | Leu | Leu | Glu | Gln | Leu | Arg |   |
|     |     |     | 35  |     |     |     |     | 40  |     |     |     |     | 45  |     |     |   |

| ACT | GGA | CTC | CAT | CAG | CAG | CTG | GAT | GAC | CTG | GAT | GCC | TGC | CTG | GGG | CAG | 190 |
|---|---|---|---|---|---|---|---|---|---|---|---|---|---|---|---|---|
| Thr | Gly | Leu | His | Gln | Gln | Leu | Asp | Asp | Leu | Asp | Ala | Cys | Leu | Gly | Gln |   |
|     |     |     | 50  |     |     |     |     | 55  |     |     |     |     | 60  |     |     |   |

| GTG | ACG | GGA | GAG | GAA | GAC | TCT | GCC | CTG | GGA | AGG | ACG | GGC | CCC | ACC | CTG | 238 |
|---|---|---|---|---|---|---|---|---|---|---|---|---|---|---|---|---|
| Val | Thr | Gly | Glu | Glu | Asp | Ser | Ala | Leu | Gly | Arg | Thr | Gly | Pro | Thr | Leu |   |
|     | 65  |     |     |     |     | 70  |     |     |     |     | 75  |     |     |     |     |   |

| GCC | ATG | AAG | ACG | TAT | TTC | CAG | GGC | ATC | CAT | GTC | TAC | CTG | AAA | GAG | AAG | 286 |
|---|---|---|---|---|---|---|---|---|---|---|---|---|---|---|---|---|
| Ala | Met | Lys | Thr | Tyr | Phe | Gln | Gly | Ile | His | Val | Tyr | Leu | Lys | Glu | Lys |   |
| 80  |     |     |     |     | 85  |     |     |     |     | 90  |     |     |     |     | 95  |   |

| GGA | TAT | AG | | | | | | | | | | | | | | 294 |
|---|---|---|---|---|---|---|---|---|---|---|---|---|---|---|---|---|
| Gly | Tyr |   |   |   |   |   |   |   |   |   |   |   |   |   |   |   |

( 2 ) INFORMATION FOR SEQ ID NO:28:

( i ) SEQUENCE CHARACTERISTICS:
( A ) LENGTH: 97 amino acids
( B ) TYPE: amino acid
( D ) TOPOLOGY: linear ( i i ) MOLECULE TYPE: protein ( v i ) ORIGINAL SOURCE:
( C ) INDIVIDUAL ISOLATE: predicted amino acid coding sequence
of SEQ ID NO:27 (HuIFNtau5).

( x i ) SEQUENCE DESCRIPTION: SEQ ID NO:28:

| Gln | Glu | Met | Val | Glu | Gly | Gly | Gln | Leu | Gln | Glu | Ala | Gln | Ala | Ile | Ser |
|---|---|---|---|---|---|---|---|---|---|---|---|---|---|---|---|
| 1   |     |     |     | 5   |     |     |     |     | 10  |     |     |     |     | 15  |     |

| Val | Leu | His | Glu | Met | Leu | Gln | Gln | Ser | Phe | Asn | Leu | Phe | His | Thr | Glu |
|---|---|---|---|---|---|---|---|---|---|---|---|---|---|---|---|
|     |     |     | 20  |     |     |     |     | 25  |     |     |     |     | 30  |     |     |

| His | Ser | Ser | Ala | Ala | Trp | Asp | Thr | Thr | Leu | Leu | Glu | Gln | Leu | Arg | Thr |
|---|---|---|---|---|---|---|---|---|---|---|---|---|---|---|---|
|     |     | 35  |     |     |     |     | 40  |     |     |     |     | 45  |     |     |     |

| Gly | Leu | His | Gln | Gln | Leu | Asp | Asp | Leu | Asp | Ala | Cys | Leu | Gly | Gln | Val |
|---|---|---|---|---|---|---|---|---|---|---|---|---|---|---|---|
|     | 50  |     |     |     |     | 55  |     |     |     |     | 60  |     |     |     |     |

| Thr | Gly | Glu | Glu | Asp | Ser | Ala | Leu | Gly | Arg | Thr | Gly | Pro | Thr | Leu | Ala |
|---|---|---|---|---|---|---|---|---|---|---|---|---|---|---|---|
| 65  |     |     |     |     | 70  |     |     |     |     | 75  |     |     |     |     | 80  |

| Met | Lys | Thr | Tyr | Phe | Gln | Gly | Ile | His | Val | Tyr | Leu | Lys | Glu | Lys | Gly |
|---|---|---|---|---|---|---|---|---|---|---|---|---|---|---|---|
|     |     |     |     | 85  |     |     |     |     | 90  |     |     |     |     | 95  |     |

Tyr ( 2 ) INFORMATION FOR SEQ ID NO:29:

( i ) SEQUENCE CHARACTERISTICS:
        ( A ) LENGTH: 516 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: HuIFNtau2

( i x ) FEATURE:
        ( A ) NAME/KEY: CDS
        ( B ) LOCATION: 1..516

( i x ) FEATURE:
        ( A ) NAME/KEY: Modified-site
        ( B ) LOCATION: 115-117
        ( D ) OTHER INFORMATION: /note= "to allow expression of the
            encoded protein this site can be modified
            to encode an amino acid, e.g., Gln"

( x i ) SEQUENCE DESCRIPTION: SEQ ID NO:29:

```
GAC CTG TCT CAG AAC CAC GTG CTG GTT GGC AGG AAG AAC CTC AGG CTC      48
Asp Leu Ser Gln Asn His Val Leu Val Gly Arg Lys Asn Leu Arg Leu
 1               5                  10                  15

CTG GAC CAA ATG AGG AGA CTC TCC CCT CGC TTT TGT CTG CAG GAC AGA      96
Leu Asp Gln Met Arg Arg Leu Ser Pro Arg Phe Cys Leu Gln Asp Arg
             20                  25                  30

AAA GAC TTC GCT TTA CCC TAG GAA ATG GTG GAG GGC GGC CAG CTC CAG     144
Lys Asp Phe Ala Leu Pro     Glu Met Val Glu Gly Gly Gln Leu Gln
         35              40                  45

GAG GCC CAG GCC ATC TCT GTG CTC CAT GAG ATG CTC CAG CAG AGC TTC     192
Glu Ala Gln Ala Ile Ser Val Leu His Glu Met Leu Gln Gln Ser Phe
     50                  55                  60

AAC CTC TTC CAC ACA GAG CAC TCC TCT GCT GCC TGG GAC ACC ACC CTC     240
Asn Leu Phe His Thr Glu His Ser Ser Ala Ala Trp Asp Thr Thr Leu
 65                  70                  75                  80

CTG GAG CAG CTC CGC ACT GGA CTC CAT CAG CAG CTG GAC AAC CTG GAT     288
Leu Glu Gln Leu Arg Thr Gly Leu His Gln Gln Leu Asp Asn Leu Asp
                 85                  90                  95

GCC TGC CTG GGG CAG GTG ATG GGA GAG GAA GAC TCT GCC CTG GGA AGG     336
Ala Cys Leu Gly Gln Val Met Gly Glu Glu Asp Ser Ala Leu Gly Arg
            100                 105                 110

ACG GGC CCC ACC CTG GCT CTG AAG AGG TAC TTC CAG GGC ATC CAT GTC     384
Thr Gly Pro Thr Leu Ala Leu Lys Arg Tyr Phe Gln Gly Ile His Val
        115                 120                 125

TAC CTG AAA GAG AAG GGA TAC AGC GAC TGC GCC TGG GAA ACC GTC AGA     432
Tyr Leu Lys Glu Lys Gly Tyr Ser Asp Cys Ala Trp Glu Thr Val Arg
    130                 135                 140

GTG GAA ATC ATG AGA TCC TTC TCT TCA TTA ATC AGC TTG CAA GAA AGG     480
Val Glu Ile Met Arg Ser Phe Ser Ser Leu Ile Ser Leu Gln Glu Arg
145                 150                 155                 160

TTA AGA ATG ATG GAT GGA GAC CTG AGC TCA CCT TGA                     516
Leu Arg Met Met Asp Gly Asp Leu Ser Ser Pro
                165                 170
```

( 2 ) INFORMATION FOR SEQ ID NO:30:

(i) SEQUENCE CHARACTERISTICS:
(A) LENGTH: 171 amino acids
(B) TYPE: amino acid
(D) TOPOLOGY: linear (ii) MOLECULE TYPE: protein (vi) ORIGINAL SOURCE:
(C) INDIVIDUAL ISOLATE: predicted amino acid coding sequence of SEQ ID NO:29 (HuIFNtau2).

(ix) FEATURE:
(A) NAME/KEY: Modified-site
(B) LOCATION: 39
(D) OTHER INFORMATION: /note= "where Xaa a selected amino acid for example, Gln"

(xi) SEQUENCE DESCRIPTION: SEQ ID NO:30:

```
Asp Leu Ser Gln Asn His Val Leu Val Gly Arg Lys Asn Leu Arg Leu
 1               5                  10                  15
Leu Asp Gln Met Arg Arg Leu Ser Pro Arg Phe Cys Leu Gln Asp Arg
            20                  25                  30
Lys Asp Phe Ala Leu Pro Xaa Glu Met Val Glu Gly Gly Gln Leu Gln
        35                  40                  45
Glu Ala Gln Ala Ile Ser Val Leu His Glu Met Leu Gln Gln Ser Phe
    50                  55                  60
Asn Leu Phe His Thr Glu His Ser Ser Ala Ala Trp Asp Thr Thr Leu
65                  70                  75                  80
Leu Glu Gln Leu Arg Thr Gly Leu His Gln Gln Leu Asp Asn Leu Asp
                85                  90                  95
Ala Cys Leu Gly Gln Val Met Gly Glu Glu Asp Ser Ala Leu Gly Arg
            100                 105                 110
Thr Gly Pro Thr Leu Ala Leu Lys Arg Tyr Phe Gln Gly Ile His Val
        115                 120                 125
Tyr Leu Lys Glu Lys Gly Tyr Ser Asp Cys Ala Trp Glu Thr Val Arg
    130                 135                 140
Val Glu Ile Met Arg Ser Phe Ser Ser Leu Ile Ser Leu Gln Glu Arg
145                 150                 155                 160
Leu Arg Met Met Asp Gly Asp Leu Ser Ser Pro
                165                 170
```

(2) INFORMATION FOR SEQ ID NO:31:

(i) SEQUENCE CHARACTERISTICS:
(A) LENGTH: 588 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: HuIFNtau3

(ix) FEATURE:
(A) NAME/KEY: CDS
(B) LOCATION: 1..588

(xi) SEQUENCE DESCRIPTION: SEQ ID NO:31:

```
ATG GCC TTC GTG CTC TCT CTA CTC ATG GCC CTG GTG CTG GTC AGC TAC    48
Met Ala Phe Val Leu Ser Leu Leu Met Ala Leu Val Leu Val Ser Tyr
 1               5                  10                  15
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| GGC | CCG | GGA | GGA | TCC | CTG | CGG | TGT | GAC | CTG | TCT | CAG | AAC | CAC | GTG | CTG | 96 |
| Gly | Pro | Gly | Gly | Ser | Leu | Arg | Cys | Asp | Leu | Ser | Gln | Asn | His | Val | Leu |    |
|     |     |     | 20  |     |     |     |     | 25  |     |     |     |     | 30  |     |     |    |
| GTT | GGC | AGC | CAG | AAC | CTC | AGG | CTC | CTG | GGC | CAA | ATG | AGG | AGA | CTC | TCC | 144 |
| Val | Gly | Ser | Gln | Asn | Leu | Arg | Leu | Leu | Gly | Gln | Met | Arg | Arg | Leu | Ser |    |
|     |     | 35  |     |     |     |     | 40  |     |     |     |     | 45  |     |     |     |    |
| CTT | CGC | TTC | TGT | CTG | CAG | GAC | AGA | AAA | GAC | TTC | GCT | TTC | CCC | CAG | GAG | 192 |
| Leu | Arg | Phe | Cys | Leu | Gln | Asp | Arg | Lys | Asp | Phe | Ala | Phe | Pro | Gln | Glu |    |
|     | 50  |     |     |     |     | 55  |     |     |     |     | 60  |     |     |     |     |    |
| ATG | GTG | GAG | GGT | GGC | CAG | CTC | CAG | GAG | GCC | CAG | GCC | ATC | TCT | GTG | CTC | 240 |
| Met | Val | Glu | Gly | Gly | Gln | Leu | Gln | Glu | Ala | Gln | Ala | Ile | Ser | Val | Leu |    |
| 65  |     |     |     |     | 70  |     |     |     |     | 75  |     |     |     |     | 80  |    |
| CAC | GAG | ATG | CTC | CAG | CAG | AGC | TTC | AAC | CTC | TTC | CAC | ACA | GAG | CAC | TCC | 288 |
| His | Glu | Met | Leu | Gln | Gln | Ser | Phe | Asn | Leu | Phe | His | Thr | Glu | His | Ser |    |
|     |     |     |     | 85  |     |     |     |     | 90  |     |     |     |     | 95  |     |    |
| TCT | GCT | GCC | TGG | GAC | ACC | ACC | CTC | CTG | GAG | CAG | CTC | CGC | ACT | GGA | CTC | 336 |
| Ser | Ala | Ala | Trp | Asp | Thr | Thr | Leu | Leu | Glu | Gln | Leu | Arg | Thr | Gly | Leu |    |
|     |     |     | 100 |     |     |     |     | 105 |     |     |     |     | 110 |     |     |    |
| CAT | CAG | CAG | CTG | GAT | GAC | CTG | GAT | GCC | TGC | CTG | GGG | CAG | GTG | ACG | GGA | 384 |
| His | Gln | Gln | Leu | Asp | Asp | Leu | Asp | Ala | Cys | Leu | Gly | Gln | Val | Thr | Gly |    |
|     |     | 115 |     |     |     |     | 120 |     |     |     |     | 125 |     |     |     |    |
| GAG | GAA | GAC | TCT | GCC | CTG | GGA | AGA | ACG | GGC | CCC | ACC | CTG | GCC | ATG | AAG | 432 |
| Glu | Glu | Asp | Ser | Ala | Leu | Gly | Arg | Thr | Gly | Pro | Thr | Leu | Ala | Met | Lys |    |
|     | 130 |     |     |     |     | 135 |     |     |     |     | 140 |     |     |     |     |    |
| AGG | TAT | TTC | CAG | GGC | ATC | CAT | GTC | TAC | CTG | AAA | GAG | AAG | GGA | TAT | AGT | 480 |
| Arg | Tyr | Phe | Gln | Gly | Ile | His | Val | Tyr | Leu | Lys | Glu | Lys | Gly | Tyr | Ser |    |
| 145 |     |     |     |     | 150 |     |     |     |     | 155 |     |     |     |     | 160 |    |
| GAC | TGC | GCC | TGG | GAA | ATT | GTC | AGA | CTG | GAA | ATC | ATG | AGA | TCC | TTG | TCT | 528 |
| Asp | Cys | Ala | Trp | Glu | Ile | Val | Arg | Leu | Glu | Ile | Met | Arg | Ser | Leu | Ser |    |
|     |     |     |     | 165 |     |     |     |     | 170 |     |     |     |     | 175 |     |    |
| TCA | TCA | ACC | AGC | TTG | CAC | AAA | AGG | TTA | AGA | ATG | ATG | GAT | GGA | GAC | CTG | 576 |
| Ser | Ser | Thr | Ser | Leu | His | Lys | Arg | Leu | Arg | Met | Met | Asp | Gly | Asp | Leu |    |
|     |     |     | 180 |     |     |     |     | 185 |     |     |     |     | 190 |     |     |    |
| AGC | TCA | CCT | TGA |     |     |     |     |     |     |     |     |     |     |     |     | 588 |
| Ser | Ser | Pro |     |     |     |     |     |     |     |     |     |     |     |     |     |    |
|     |     | 195 |     |     |     |     |     |     |     |     |     |     |     |     |     |    |

( 2 ) INFORMATION FOR SEQ ID NO:32:

( i ) SEQUENCE CHARACTERISTICS:
        ( A ) LENGTH: 195 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: predicted amino acid coding sequence
           of SEQ ID NO:31 (HuIFNtau3)

( x i ) SEQUENCE DESCRIPTION: SEQ ID NO:32:

| Met | Ala | Phe | Val | Leu | Ser | Leu | Leu | Met | Ala | Leu | Val | Leu | Val | Ser | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gly | Pro | Gly | Gly | Ser | Leu | Arg | Cys | Asp | Leu | Ser | Gln | Asn | His | Val | Leu |
|     |     |     | 20  |     |     |     |     | 25  |     |     |     |     | 30  |     |     |
| Val | Gly | Ser | Gln | Asn | Leu | Arg | Leu | Leu | Gly | Gln | Met | Arg | Arg | Leu | Ser |
|     |     | 35  |     |     |     |     | 40  |     |     |     |     | 45  |     |     |     |
| Leu | Arg | Phe | Cys | Leu | Gln | Asp | Arg | Lys | Asp | Phe | Ala | Phe | Pro | Gln | Glu |
|     | 50  |     |     |     |     | 55  |     |     |     |     | 60  |     |     |     |     |
| Met | Val | Glu | Gly | Gly | Gln | Leu | Gln | Glu | Ala | Gln | Ala | Ile | Ser | Val | Leu |
| 65  |     |     |     |     | 70  |     |     |     |     | 75  |     |     |     |     | 80  |
| His | Glu | Met | Leu | Gln | Gln | Ser | Phe | Asn | Leu | Phe | His | Thr | Glu | His | Ser |

|   |   |   |   |   |   |   | 85 |   |   |   |   | 90 |   |   |   |   | 95 |   |   |
|---|---|---|---|---|---|---|---|---|---|---|---|---|---|---|---|---|---|---|---|

Ser Ala Ala Trp Asp Thr Thr Leu Leu Glu Gln Leu Arg Thr Gly Leu
            100                 105                 110

His Gln Gln Leu Asp Asp Leu Asp Ala Cys Leu Gly Gln Val Thr Gly
            115                 120                 125

Glu Glu Asp Ser Ala Leu Gly Arg Thr Gly Pro Thr Leu Ala Met Lys
    130                 135                 140

Arg Tyr Phe Gln Gly Ile His Val Tyr Leu Lys Glu Lys Gly Tyr Ser
145                 150                 155                 160

Asp Cys Ala Trp Glu Ile Val Arg Leu Glu Ile Met Arg Ser Leu Ser
                165                 170                 175

Ser Ser Thr Ser Leu His Lys Arg Leu Arg Met Met Asp Gly Asp Leu
            180                 185                 190

Ser Ser Pro
        195

( 2 ) INFORMATION FOR SEQ ID NO:33:

( i ) SEQUENCE CHARACTERISTICS:
        ( A ) LENGTH: 518 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: HuIFNtau3, mature no leader sequence ( i x ) FEATURE:
        ( A ) NAME/KEY: CDS
        ( B ) LOCATION: 1..518

( x i ) SEQUENCE DESCRIPTION: SEQ ID NO:33:

TGT GAC CTG TCT CAG AAC CAC GTG CTG GTT GGC AGC CAG AAC CTC AGG    48
Cys Asp Leu Ser Gln Asn His Val Leu Val Gly Ser Gln Asn Leu Arg
 1               5                  10                  15

CTC CTG GGC CAA ATG AGG AGA CTC TCC CTT CGC TTC TGT CTG CAG GAC    96
Leu Leu Gly Gln Met Arg Arg Leu Ser Leu Arg Phe Cys Leu Gln Asp
            20                  25                  30

AGA AAA GAC TTC GCT TTC CCC CAG GAG ATG GTG GAG GGT GGC CAG CTC   144
Arg Lys Asp Phe Ala Phe Pro Gln Glu Met Val Glu Gly Gly Gln Leu
        35                  40                  45

CAG GAG GCC CAG GCC ATC TCT GTG CTC CAC GAG ATG CTC CAG CAG AGC   192
Gln Glu Ala Gln Ala Ile Ser Val Leu His Glu Met Leu Gln Gln Ser
    50                  55                  60

TTC AAC CTC TTC CAC ACA GAG CAC TCC TCT GCT GCC TGG GAC ACC ACC   240
Phe Asn Leu Phe His Thr Glu His Ser Ser Ala Ala Trp Asp Thr Thr
 65                  70                  75                  80

CTC CTG GAG CAG CTC CGC ACT GGA CTC CAT CAG CAG CTG GAT GAC CTG   288
Leu Leu Glu Gln Leu Arg Thr Gly Leu His Gln Gln Leu Asp Asp Leu
                85                  90                  95

GAT GCC TGC CTG GGG CAG GTG ACG GGA GAG GAA GAC TCT GCC CTG GGA   336
Asp Ala Cys Leu Gly Gln Val Thr Gly Glu Glu Asp Ser Ala Leu Gly
            100                 105                 110

AGA ACG GGC CCC ACC CTG GCC ATG AAG AGG TAT TTC CAG GGC ATC CAT   384
Arg Thr Gly Pro Thr Leu Ala Met Lys Arg Tyr Phe Gln Gly Ile His
        115                 120                 125

GTC TAC CTG AAA GAG AAG GGA TAT AGT GAC TGC GCC TGG GAA ATT GTC   432

```
Val  Tyr  Leu  Lys  Glu  Lys  Gly  Tyr  Ser  Asp  Cys  Ala  Trp  Glu  Ile  Val
     130                 135                      140

AGA  CTG  GAA  ATC  ATG  AGA  TCC  TTG  TCT  TCA  TCA  ACC  AGC  TTG  CAC  AAA        480
Arg  Leu  Glu  Ile  Met  Arg  Ser  Leu  Ser  Ser  Ser  Thr  Ser  Leu  His  Lys
145                      150                      155                      160

AGG  TTA  AGA  ATG  ATG  GAT  GGA  GAC  CTG  AGC  TCA  CCT  TG                        518
Arg  Leu  Arg  Met  Met  Asp  Gly  Asp  Leu  Ser  Ser  Pro
               165                      170
```

( 2 ) INFORMATION FOR SEQ ID NO:34:

( i ) SEQUENCE CHARACTERISTICS:
        ( A ) LENGTH: 172 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

```
Cys  Asp  Leu  Ser  Gln  Asn  His  Val  Leu  Val  Gly  Ser  Gln  Asn  Leu  Arg
 1                   5                        10                       15

Leu  Leu  Gly  Gln  Met  Arg  Arg  Leu  Ser  Leu  Arg  Phe  Cys  Leu  Gln  Asp
               20                       25                       30

Arg  Lys  Asp  Phe  Ala  Phe  Pro  Gln  Glu  Met  Val  Glu  Gly  Gly  Gln  Leu
          35                        40                       45

Gln  Glu  Ala  Gln  Ala  Ile  Ser  Val  Leu  His  Glu  Met  Leu  Gln  Gln  Ser
     50                       55                       60

Phe  Asn  Leu  Phe  His  Thr  Glu  His  Ser  Ser  Ala  Ala  Trp  Asp  Thr  Thr
 65                      70                       75                       80

Leu  Leu  Glu  Gln  Leu  Arg  Thr  Gly  Leu  His  Gln  Gln  Leu  Asp  Asp  Leu
               85                       90                       95

Asp  Ala  Cys  Leu  Gly  Gln  Val  Thr  Gly  Glu  Glu  Asp  Ser  Ala  Leu  Gly
               100                      105                      110

Arg  Thr  Gly  Pro  Thr  Leu  Ala  Met  Lys  Arg  Tyr  Phe  Gln  Gly  Ile  His
               115                      120                      125

Val  Tyr  Leu  Lys  Glu  Lys  Gly  Tyr  Ser  Asp  Cys  Ala  Trp  Glu  Ile  Val
     130                 135                      140

Arg  Leu  Glu  Ile  Met  Arg  Ser  Leu  Ser  Ser  Ser  Thr  Ser  Leu  His  Lys
145                      150                      155                      160

Arg  Leu  Arg  Met  Met  Asp  Gly  Asp  Leu  Ser  Ser  Pro
               165                      170
```

( 2 ) INFORMATION FOR SEQ ID NO:35:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: Amino acid sequence of fragment
        1-37 of SEQ ID NO:33

( x i ) SEQUENCE DESCRIPTION: SEQ ID NO:35:

```
Cys  Asp  Leu  Ser  Gln  Asn  His  Val  Leu  Val  Gly  Ser  Gln  Asn  Leu  Arg
 1                   5                        10                       15

Leu  Leu  Gly  Gln  Met  Arg  Arg  Leu  Ser  Leu  Arg  Phe  Cys  Leu  Gln  Asp
               20                       25                       30

Arg  Lys  Asp  Phe  Ala
          35
```

( 2 ) INFORMATION FOR SEQ ID NO:36:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: Amino acid sequence of fragment
        34-64 of SEQ ID NO:33

( x i ) SEQUENCE DESCRIPTION: SEQ ID NO:36:

```
Lys  Asp  Phe  Ala  Phe  Pro  Gln  Glu  Met  Val  Glu  Gly  Gly  Gln  Leu  Gln
 1              5                        10                            15

Glu  Ala  Gln  Ala  Ile  Ser  Val  Leu  His  Glu  Met  Leu  Gln  Gln  Ser
           20                       25                       30
```

( 2 ) INFORMATION FOR SEQ ID NO:37:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: Amino acid sequence of fragment
        62-92 of SEQ ID NO:33

( x i ) SEQUENCE DESCRIPTION: SEQ ID NO:37:

```
Gln  Gln  Ser  Phe  Asn  Leu  Phe  His  Thr  Glu  His  Ser  Ser  Ala  Ala  Trp
 1              5                        10                            15

Asp  Thr  Thr  Leu  Leu  Glu  Gln  Leu  Arg  Thr  Gly  Leu  His  Gln  Gln
           20                       25                       30
```

( 2 ) INFORMATION FOR SEQ ID NO:38:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: Amino acid sequence of fragment
        90-122 of SEQ ID NO:33

( x i ) SEQUENCE DESCRIPTION: SEQ ID NO:38:

```
His  Gln  Gln  Leu  Asp  Asp  Leu  Asp  Ala  Cys  Leu  Gly  Gln  Val  Thr  Gly
 1              5                        10                            15

Glu  Glu  Asp  Ser  Ala  Leu  Gly  Arg  Thr  Gly  Pro  Thr  Leu  Ala  Met  Lys
           20                       25                       30

Arg
```

( 2 ) INFORMATION FOR SEQ ID NO:39:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( v i ) ORIGINAL SOURCE:

( C ) INDIVIDUAL ISOLATE: Amino acid sequence of fragment
119-150 of SEQ ID NO:33

( x i ) SEQUENCE DESCRIPTION: SEQ ID NO:39:

```
Ala Met Lys Arg Tyr Phe Gln Gly Ile His Val Tyr Leu Lys Glu Lys
 1               5                  10                  15

Gly Tyr Ser Asp Cys Ala Trp Glu Ile Val Arg Leu Glu Ile Met Arg
            20                  25                  30
```

( 2 ) INFORMATION FOR SEQ ID NO:40:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: Amino acid sequence of fragment
        139-172 of SEQ ID NO:33

( x i ) SEQUENCE DESCRIPTION: SEQ ID NO:40:

```
Cys Ala Trp Glu Ile Val Arg Leu Glu Ile Met Arg Ser Leu Ser Ser
 1               5                  10                  15

Ser Thr Ser Leu His Lys Arg Leu Arg Met Met Asp Gly Asp Leu Ser
            20                  25                  30

Ser Pro
```

( 2 ) INFORMATION FOR SEQ ID NO:41:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: Amino acid sequence of fragment
        1-23 of SEQ ID NO:32

( x i ) SEQUENCE DESCRIPTION: SEQ ID NO:41:

```
Met Ala Phe Val Leu Ser Leu Leu Met Ala Leu Val Leu Val Ser Tyr
 1               5                  10                  15

Gly Pro Gly Gly Ser Leu Arg
            20
```

( 2 ) INFORMATION FOR SEQ ID NO:42:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( v i ) ORIGINAL SOURCE:
        ( C ) INDIVIDUAL ISOLATE: Amino acid sequence of fragment
        1-23 of SEQ ID NO:11

( x i ) SEQUENCE DESCRIPTION: SEQ ID NO:42:

```
Met Ala Phe Val Leu Ser Leu Leu Met Ala Leu Val Leu Val Ser Tyr
 1               5                  10                  15

Gly Pro Gly Gly Ser Leu Gly
            20
```

( 2 ) INFORMATION FOR SEQ ID NO:43:

( i ) SEQUENCE CHARACTERISTICS:
        ( A ) LENGTH: 519 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: HuIFNtau1 genomic-derived
            DNA coding sequence, without leader seq.

( i x ) FEATURE:
        ( A ) NAME/KEY: CDS
        ( B ) LOCATION: 1..519

( x i ) SEQUENCE DESCRIPTION: SEQ ID NO:43:

```
TGT  GAC  CTG  TCT  CAG  AAC  CAC  GTG  CTG  GTT  GGC  AGG  AAG  AAC  CTC  AGG        48
Cys  Asp  Leu  Ser  Gln  Asn  His  Val  Leu  Val  Gly  Arg  Lys  Asn  Leu  Arg
 1              5                      10                      15

CTC  CTG  GAC  GAA  ATG  AGG  AGA  CTC  TCC  CCT  CGC  TTT  TGT  CTG  CAG  GAC        96
Leu  Leu  Asp  Glu  Met  Arg  Arg  Leu  Ser  Pro  Arg  Phe  Cys  Leu  Gln  Asp
                20                      25                      30

AGA  AAA  GAC  TTC  GCT  TTA  CCC  CAG  GAA  ATG  GTG  GAG  GGC  CAG  CTC       144
Arg  Lys  Asp  Phe  Ala  Leu  Pro  Gln  Glu  Met  Val  Glu  Gly  Gln  Leu
           35                      40                      45

CAG  GAG  GCC  CAG  GCC  ATC  TCT  GTG  CTC  CAT  GAG  ATG  CTC  CAG  CAG  AGC       192
Gln  Glu  Ala  Gln  Ala  Ile  Ser  Val  Leu  His  Glu  Met  Leu  Gln  Gln  Ser
      50                      55                      60

TTC  AAC  CTC  TTC  CAC  ACA  GAG  CAC  TCC  TCT  GCT  GCC  TGG  GAC  ACC  ACC       240
Phe  Asn  Leu  Phe  His  Thr  Glu  His  Ser  Ser  Ala  Ala  Trp  Asp  Thr  Thr
 65                      70                      75                      80

CTC  CTG  GAG  CAG  CTC  CGC  ACT  GGA  CTC  CAT  CAG  CAG  CTG  GAC  AAC  CTG       288
Leu  Leu  Glu  Gln  Leu  Arg  Thr  Gly  Leu  His  Gln  Gln  Leu  Asp  Asn  Leu
                85                      90                      95

GAT  GCC  TGC  CTG  GGG  CAG  GTG  ATG  GGA  GAG  GAA  GAC  TCT  GCC  CTG  GGA       336
Asp  Ala  Cys  Leu  Gly  Gln  Val  Met  Gly  Glu  Glu  Asp  Ser  Ala  Leu  Gly
               100                     105                     110

AGG  ACG  GGC  CCC  ACC  CTG  GCT  CTG  AAG  AGG  TAC  TTC  CAG  GGC  ATC  CAT       384
Arg  Thr  Gly  Pro  Thr  Leu  Ala  Leu  Lys  Arg  Tyr  Phe  Gln  Gly  Ile  His
          115                     120                     125

GTC  TAC  CTG  AAA  GAG  AAG  GGA  TAC  AGC  GAC  TGC  GCC  TGG  GAA  ACC  GTC       432
Val  Tyr  Leu  Lys  Glu  Lys  Gly  Tyr  Ser  Asp  Cys  Ala  Trp  Glu  Thr  Val
     130                     135                     140

AGA  CTG  GAA  ATC  ATG  AGA  TCC  TTC  TCT  TCA  TTA  ATC  AGC  TTG  CAA  GAA       480
Arg  Leu  Glu  Ile  Met  Arg  Ser  Phe  Ser  Ser  Leu  Ile  Ser  Leu  Gln  Glu
145                     150                     155                     160

AGG  TTA  AGA  ATG  ATG  GAT  GGA  GAC  CTG  AGC  TCA  CCT  TGA                      519
Arg  Leu  Arg  Met  Met  Asp  Gly  Asp  Leu  Ser  Ser  Pro
                165                     170
```

( 2 ) INFORMATION FOR SEQ ID NO:44:

( i ) SEQUENCE CHARACTERISTICS:
        ( A ) LENGTH: 172 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

| Cys | Asp | Leu | Ser | Gln | Asn | His | Val | Leu | Val | Gly | Arg | Lys | Asn | Leu | Arg |
|---|---|---|---|---|---|---|---|---|---|---|---|---|---|---|---|
| 1 | | | | 5 | | | | | 10 | | | | | 15 | |
| Leu | Leu | Asp | Glu | Met | Arg | Arg | Leu | Ser | Pro | Arg | Phe | Cys | Leu | Gln | Asp |
| | | | 20 | | | | | 25 | | | | | 30 | | |
| Arg | Lys | Asp | Phe | Ala | Leu | Pro | Gln | Glu | Met | Val | Glu | Gly | Gly | Gln | Leu |
| | | 35 | | | | | 40 | | | | | 45 | | | |
| Gln | Glu | Ala | Gln | Ala | Ile | Ser | Val | Leu | His | Glu | Met | Leu | Gln | Gln | Ser |
| | 50 | | | | | 55 | | | | | 60 | | | | |
| Phe | Asn | Leu | Phe | His | Thr | Glu | His | Ser | Ser | Ala | Ala | Trp | Asp | Thr | Thr |
| 65 | | | | | 70 | | | | | 75 | | | | | 80 |
| Leu | Leu | Glu | Gln | Leu | Arg | Thr | Gly | Leu | His | Gln | Gln | Leu | Asp | Asn | Leu |
| | | | | 85 | | | | | 90 | | | | | 95 | |
| Asp | Ala | Cys | Leu | Gly | Gln | Val | Met | Gly | Glu | Glu | Asp | Ser | Ala | Leu | Gly |
| | | | 100 | | | | | 105 | | | | | 110 | | |
| Arg | Thr | Gly | Pro | Thr | Leu | Ala | Leu | Lys | Arg | Tyr | Phe | Gln | Gly | Ile | His |
| | | 115 | | | | | 120 | | | | | 125 | | | |
| Val | Tyr | Leu | Lys | Glu | Lys | Gly | Tyr | Ser | Asp | Cys | Ala | Trp | Glu | Thr | Val |
| | 130 | | | | | 135 | | | | | 140 | | | | |
| Arg | Leu | Glu | Ile | Met | Arg | Ser | Phe | Ser | Ser | Leu | Ile | Ser | Leu | Gln | Glu |
| 145 | | | | | 150 | | | | | 155 | | | | | 160 |
| Arg | Leu | Arg | Met | Met | Asp | Gly | Asp | Leu | Ser | Ser | Pro | | | | |
| | | | | 165 | | | | | 170 | | | | | | |